United States Patent
Lee et al.

[11] Patent Number: 5,776,950
[45] Date of Patent: Jul. 7, 1998

[54] CYCLOANTHELMINTIC INHIBITORS

[75] Inventors: Byung H. Lee; Pil H. Lee, both of Kalamazoo; William W. McWhorter, Jr., Parchment; Fred E. Dutton, Kalamazoo, all of Mich.

[73] Assignee: Pharmacia & Upjohn Company, Kalamazzoo, Mich.

[21] Appl. No.: 708,768

[22] Filed: Sep. 5, 1996

Related U.S. Application Data

[60] Provisional application No. 60/003,323, Sep. 7, 1995.

[51] Int. Cl.$^6$ .............................. A01N 43/40; A61K 38/12
[52] U.S. Cl. .............................. 514/317; 530/317
[58] Field of Search .............................. 530/317; 514/11

[56] References Cited

U.S. PATENT DOCUMENTS

| | | | |
|---|---|---|---|
| 5,116,815 | 5/1992 | Tagaki et al. | 514/11 |
| 5,380,745 | 1/1995 | Uomoto et al. | 514/410 |
| 5,514,773 | 5/1996 | Nishiyama et al. | 530/317 |

FOREIGN PATENT DOCUMENTS

| | | | |
|---|---|---|---|
| 382173 | 2/1990 | European Pat. Off. | |
| 0 382 173 A2 | 8/1990 | European Pat. Off. | C07D 273/00 |
| 0 503 538 A1 | 9/1992 | European Pat. Off. | A61K 37/02 |
| 626376 | 5/1994 | European Pat. Off. | |
| 0 626 375 A1 | 11/1994 | European Pat. Off. | C07D 273/00 |
| 0 626 376 A1 | 11/1994 | European Pat. Off. | C07D 273/00 |
| 0 634 408 A1 | 1/1995 | European Pat. Off. | C07D 273/00 |
| 4 317 458-A1 | 6/1992 | Germany | C07D 273/00 |
| 0 5 117 298-A | 4/1993 | Japan | |
| 0 5 170 749-A | 7/1993 | Japan | C07D 263/00 |
| 0 5 229 997-A | 9/1993 | Japan | |
| WO 94/19334 | 9/1994 | Japan | C07D 273/00 |
| WO 96/08266 | 3/1996 | WIPO | A61K 12/38 |

OTHER PUBLICATIONS

Terada, M., Japan. J. Parasitol., 41, pp. 108–117 (1992).
Sasaki, T., et al., J. Antibiotics, 45, p. 692 (1992).
Dutton, F. E., et al., J. Antibiotics, 47, pp. 1322–1327(1994).

*Primary Examiner*—Mukund J. Shah
*Assistant Examiner*—Bruck Kifle
*Attorney, Agent, or Firm*—Thomas A. Wootton

[57] ABSTRACT

This invention comprises novel compounds that inhibit the growth of helminths. The compounds have the structure of Formula I, below.

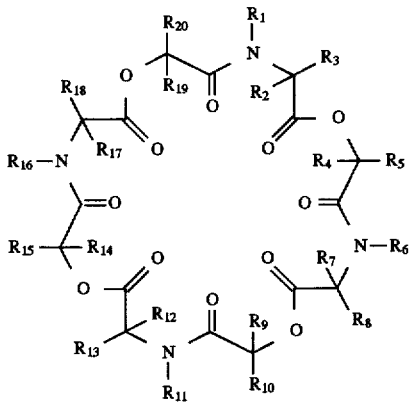

Where the R groups are defined according to the specification and claims.

57 Claims, No Drawings

CYCLOANTHELMINTIC INHIBITORS

CROSS-REFERENCE TO RELATED APPLICATIONS

This application claims the benefit of U.S. provisional application Ser. No. 60/003,323 filed 7 Sep. 1995, under 35 USC §119(e)(i).

FIELD OF THE INVENTION

This invention is comprised of novel compounds related to the compound known as pf1022a. The compounds are useful as antiparasitic and antimicrobial agents.

INFORMATION DISCLOSURE

1. Takagi, M., et. al., Meji Seika Co., Ltd., U.S. Pat. No. 5,116,815 (1992).
2. Uomoto, K. et. al., Meji Seika Co., Ltd., European Patent 0,503,538 A1 (1992).92-309657/38 is EP 503538-A1 assigned to Meii Seika Kaisha. Compounds with enhanced anthelmintic effect—comprising anthelmintic compound PF1022, nonionic surfactants and/or oils and fats and optional aquious solvents.
3. Takagi, M., et. al., Meji Seika Co., Ltd., European Patent 0,382,173 A2 (1990). 90-248114/33 is EP 382-173-A assigned to MeUi Seika Kaisha. New macrocyclic lactam-lactone derived PF 1022—useful as anthelmintic for human and veterinary medicine, prepared by culturing fungus Ferm BP 2671.
4. Nishiyama, H., et. al., Fujisawa Pharmaceutical Co., Ltd., European Patent 0,634,408 A1 (1993).
5. Scherkenbeck, J., et. al., Bayer AG, European Patent 0,626,375 A1 (1994).
6. Scherkenbeck, J., et. al., Bayer AG, European Patent 0,626,376 A1 (1994).
7. Ohyama, M., et. al., Meji Seika Co., Ltd., WO 94/19334 (1994).
8. Nishiyama, H., et. al., Fujisawa Pharmaceutical Co., Ltd., WO 93/19053 (1993). 93-320652/40 is WO 9319053-A1 assigned to Fujisawa Pharm Co. Ltd. New depsipeptide(s) used in treatment of helmintic infections having broad spectrum of activity against various internal parasites. WO 93/19053 is PCT/JP93/00286.
9. Nishiyama, H., et. al., Fujisawa Pharmaceutical Co., Ltd., Tokkai Hei 5-229997 (1993). 93-317424/40 is JP 05229997-A assigned to Fujisawa Pharm Co. Ltd.
10. 93-252718/32 is JP 05170749-A Assigned to MeUi Seika Kaisha. New cyclic depsipeptide having antihelminthic activity is prepared by culturing Asporogenous fungi.
11. 93-191507/24 is JP 05117298-A Assigned to Rikagaku Kenkyusho. Novel depsipeptide A and depsipeptide B useful as antibacterial and antiviral agents—are prepared by culturing Streptomyces or antinomycetes RK-1051.
12. WO 96/08266, published 21 Mar. 1996, assigned to Merck & Co., inventors Balkovec, James et al.
13. DE 4317458-A1 assigned to Bayer AG.
14. Terada, M., Japan. J. Parasitol., vol. 41, pp. 108–17 (1992).
15. Sasaki, T., et. al., J. Antibiotics, vol. 45, pp. 692 (1992).
16. Dutton, F. E., et. al., J. Antibiotics, vol. 47, pp. 1322–7 (1994).

BACKGROUND

Parasitic diseases may be caused by either endoparasites or ectoparasites. Endoparasites are those parasites which live inside the body of the host, either within an organ (such as the stomach, lungs, heart, intestines, etc.) or simply under the skin. Ectoparasites are those parasites which live on the outer surface of the host but still draw nutrients from the host.

The endoparasitic diseases generally referred to as helminthiasis are due to infection of the host with parasitic worms known as helminths. Helminthiasis is a prevalent and serious worldwide economic problem due to infection of domesticated animals such as swine, sheep, horses, cattle, goats, dogs, cats, and poultry. Many of these infections are caused by the group of worms described as nematodes which cause diseases in various species of animals throughout the world. These diseases are frequently serious and can result in the death of the infected animal. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris, and Parascaris. Many parasites are species specific (infect only one host) and most also have a preferred site of infection within the animal. Thus Haemonchus and Ostertagia primarily infect the stomach while Nematodirus and Cooperia mostly attack the intestines. Other parasites prefer to reside in the heart, eyes, lungs, blood vessels, and the like while still others are subcutaneous parasites. Helminthiasis can lead to weakness, weight loss, anemia, intestinal damage, malnutrition, and damage to other organs. If left untreated these diseases can result in the death of the animal.

Infections by ectoparasitic arthropods such as ticks, mites, lice, stable flies, hornflies, blowflies, fleas, and the like are also a serious problem. Infection by these parasites results in loss of blood, skin lesions, and can interfere with normal eating habits thus causing weight loss. These infections can also result in transmission of serious diseases such as encephalitis, anaplasmosis, swine pox, and the like which can be fatal.

Animals may be infected by several species of parasite at the same time since infection by one parasite may weaken the animal and make it more susceptible to infection by a second species of parasite. Thus, a compound with a broad spectrum of activity is particularly advantageous in the treatment of these diseases. The compounds of this invention have unexpectedly high activity against these parasites, and in addition, are also active against Dirofilaria in dogs, Nematospiroides and Syphacia in rodents, biting insects and migrating diperous larvae such as Hypoderma sp. in cattle, and Gastrophilus in horses. The instant compounds are also useful against endo and ecto parasites which cause parasitic diseases in humans.

SUMMARY OF THE INVENTION

This invention is comprised of novel compounds, useful for treating disease caused by or for controling the growth and replication of anthelmitic organisms. The invention comprises 3 groups of compounds. Group 1 compounds are represented by formula I, below,

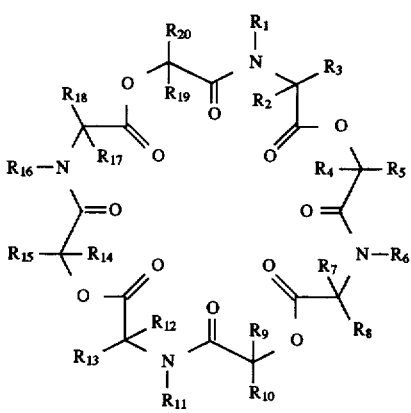

where, $R_1$, $R_6$, $R_{11}$ and $R_{16}$ are independent and selected from, a) H, or b) $C_{1-4}$ optionally substituted alkyl, the alkyl optionally terminally substituted with, hydroxy or $C_{1-2}$alkoxy, where, $R_2$, $R_3$, $R_4$, $R_5$, $R_7$, $R_8$, $R_9$, $R_{10}$, $R_{12}$, $R_{13}$, $R_{14}$, $R_{15}$, $R_{17}$, $R_{18}$, $R_{19}$ and $R_{20}$, are independent and selected from, a) H, b) $C_{1-11}$ alkyl, c) $C_{2-11}$, alkenyl, d) $C_{3-6}$ cycloalkyl, e) $C_{1-11}$ alkoxy, f) $C_{1-11}$ alkyl-$C_{1-11}$ alkoxy, g) $C_{1-11}$, alkyl-O—$C_{1-6}$ alkyl, h) $C_{6-12}$ aryl, i) $C_{1-11}$ alkyl-$C_{6-12}$ aryl, j) heterocyclic group, k) $C_{1-11}$ alkyl-heterocyclic group, where, the heterocyclic group may be morpholino, piperidino, piperazino, imidazolyl, indolyl or guanidino, where, at least one of the following combinations of two R groups, $R_1$ with $R_3$, $R_6$ with $R_8$, $R_{11}$ with $R_{13}$, and $R_{16}$ with $R_{18}$, are taken together, to form a heterocyclic ring structure, to form, 1) an optionally substituted heterocyclic ring of 5 to 9 members, or 2) a heterocyclic ring having the Nitrogen as shown in Formula I plus the additional optionally substituted ring atoms, where the ring atoms other than the N shown in Formula I may be either entirely C, or at least two carbon atoms plus one to three N, O or S substituted with 0–6 groups selected from, i) $C_{1-6}$ alkyl, ii) $C_{2-6}$ alkenyl, iii) $C_{3-6}$ cycloalkyl, iv) phenyl, v) heterocyclic group, where the heterocyclic group is as defined above, or 3) a double ring system where the two R groups ($R_1$ with $R_3$, $R_6$ with $R_8$, $R_{11}$ with $R_{13}$, or $R_{16}$ with $R_{18}$,) may be taken together to form a double ring system where each ring contains 5, 6 or 7 members (allowing double counting of common members), where, i) the first ring is attached to the second ring directly with no covalent bonds (spiral type) or through a single covalent bond, (such as biphenyl type) between the two rings, or ii) the first ring is attached to the second ring with one point of attachment on the first and second ring with either no carbons but one covalent bond (biphenyl type) or one carbon atom and two covalent bonds between the two rings, or iii) the first ring shares a covalent bond with the second ring such that common ring members are counted twice, as with an indole type structures, where either the cyclic carbon ring, the heterocyclic ring or the double ring system may be optionally substituted with, 1) $C_{1-4}$ alkyl, or 2) $C_{2-4}$ alkenyl; and pharmaceutically acceptable salts thereof.

The invention more specifically claims a compound of formula 1 where at least one of one of the following combinations of two R groups, $R_1$ with $R_3$, $R_6$ with $R_8$, $R_{11}$ with $R_{13}$, and $R_{16}$ with $R_{18}$, taken together, form a single or double heterocyclic ring. In addition $R_1$ through $R_{20}$, inclusive, may be independently;

H, $C_{1-6}$ alkyl, optionally substituted $C_{1-6}$ alkyl-$C_{6-12}$aryl or form part of a single or double heterocyclic ring. In more preferred embodiments the combination of said two R groups will form a heterocyclic ring nucleus containing 5, 6 or 7 members comprising one Nitrogen atom. In other preferred embodiments $R_2$, $R_4$, $R_7$, $R_9$, $R_{12}$, $R_{14}$, and $R_{17}$ are hydrogen, $R_3$ with $R_1$ form a 5, 6 or 7 member ring and $R_8$, $R_{13}$, and $R_{18}$, are independently, $C_1$–$C_4$ alkyl. In some cases where $R_3$ with $R_1$ form a 5 member ring then $R_2$ is H or $C_{1-4}$ alkyl and $R_8$, $R_{13}$, and $R_{18}$, are all iso-butyl.

In some preferred embodiments $R_1$ with $R_3$ form a 6 member ring, $R_2$ is H or $C_{1-4}$ alkyl and $R_6$, $R_{11}$, or $R_{16}$ is H or $C_{1-4}$ alkyl. In other preferred embodiments $R_4$, $R_5$, $R_7$, $R_8$, $R_9$, $R_{10}$, $R_{12}$, $R_{13}$, $R_{14}$, $R_{15}$, $R_{17}$, $R_{18}$, $R_{19}$, $R_{20}$, are H, $C_{1-6}$ alkyl, benzyl or substituted benzyl. Often $R_6$, $R_{11}$, or $R_{16}$ are H or methyl. Often where $R_6$, $R_{11}$, or $R_{16}$ are methyl then, $R_4$, $R_5$, $R_7$, $R_8$, $R_9$, $R_{10}$, $R_{12}$, $R_{13}$, $R_{14}$, $R_{15}$, $R_{17}$, $R_{18}$, $R_{19}$, $R_{20}$, are H, methyl, benzyl or iso-butyl and $R_2$, $R_4$, $R_7$, $R_9$, $R_{12}$, $R_{14}$, $R_{17}$, $R_{19}$, are H.

Examples are provided where $R_{20}$, $R_{15}$, $R_{10}$, or $R_5$ are selected from morpholino substituted benzyl and where a six member ring formed by $R_1$ with $R_3$ contains a S atom as one member of that ring.

Other preferred compounds have $R_1$ with $R_3$ form a 7 member ring where $R_2$ is H or $C_{1-4}$ alkyl and $R_6$, $R_{11}$, or $R_{16}$ is H or $C_{1-4}$ alkyl. Other R groups may be as above. In addition, the seven member ring formed from $R_1$ with $R_3$ contains a S atom.

In some preferred examples $R_1$ with $R_3$ may form a double ring system where each ring contains 6 members, where the first ring shares a covalent bond with the second ring such that common members are counted twice, where the double ring system may be substituted. In these embodiments the second ring may be aryl or substituted aryl, where $R_2$ is H or $C_{1-4}$ alkyl, where $R_6$, $R_{11}$, or $R_{16}$ is H or $C_{1-4}$ alkyl, and where, $R_4$, $R_5$, $R_7$, $R_8$, $R_9$, $R_{10}$, $R_{12}$, $R_{13}$, $R_{14}$, $R_{15}$, $R_{17}$, $R_{18}$, $R_{19}$, $R_{20}$, are H, $C_{1-6}$ alkyl, benzyl or substituted benzyl. More preferred is where $R_6$, $R_{11}$, or $R_{16}$ are H or methyl, where $R_6$, $R_{11}$, or $R_{16}$ are methyl, where, $R_4$, $R_5$, $R_7$, $R_8$, $R_9$, $R_{10}$, $R_{12}$, $R_{13}$, $R_{14}$, $R_{15}$, $R_{17}$, $R_{18}$, $R_{19}$, $R_{20}$, are H, methyl, benzyl or iso-butyl, and where $R_2$, $R_4$, $R_7$, $R_9$, $R_{12}$, $R_{14}$, $R_{17}$, $R_{19}$, are H.

Other compounds of this invention are labeled as Group 2 or Group 3 compounds and these are comprised of compounds represented by formula I, below,

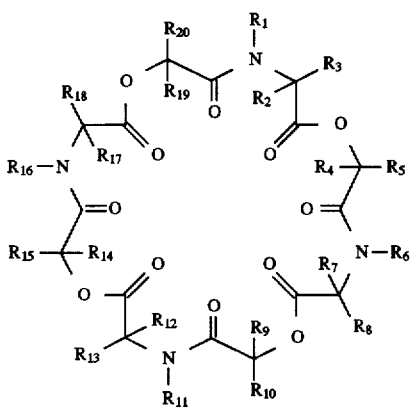

where, $R_1$, $R_6$, $R_{11}$ and $R_{16}$ are defined the same as the Group 1 variables, where, $R_2$, $R_3$, $R_4$, $R_5$, R7, $R_8$, $R_9$, $R_{10}$, $R_{12}$, $R_{14}$, $R_{15}$, $R_{17}$, $R_{18}$, $R_{19}$ and $R_{20}$, are defined the same as the Group 1 variables where, the heterocyclic groups may be morpholino, piperidino, piperazino, imidazolyl, indolyl or guanidino, where, at least one of the following combinations of two R groups, $R_1$ with $R_{20}$, $R_6$ with $R_5$, $R_{11}$ with $R_{10}$, and $R_{16}$ with $R_{15}$, are taken together, to form a heterocyclic ring structure, to form, 1) an optionally substituted heterocyclic ring of 5 to 9 members, or
2) a heterocyclic ring having the Nitrogen as shown in Formula I plus the additional optionally substituted ring atoms, where the ring atoms other than the N shown in Formula I may be either entirely C, or at least two carbon atoms plus one to three N, O or S substituted with 0–6 groups selected from, i) $C_{1-6}$ alkyl, ii) $C_{2-6}$ alkenyl, iii) $C_{3-6}$ cycloalkyl, iv) phenyl, v) heterocyclic group, where the heterocyclic group is as defined above, or 3) a double ring system where the two R groups ($R_1$ with $R_{20}$, $R_6$ with $R_5$, $R_{11}$ with $R_{10}$, or $R_{16}$ with $R_{15}$,) may be taken together to form a double ring system where each ring contains 5, 6 or 7 members (allowing double counting of common members), where i) the first ring is attached to the second ring directly with no covalent bonds (spiral type) or through a single covalent bond, (such as biphenyl type) between the two rings, or ii) the first ring is attached to the second ring with one point of attachment on the first and second ring with either no carbons but one covalent bond (biphenyl type) or one carbon atom and two covalent bonds between the two rings, or iii) the first ring shares a covalent bond with the second ring such that common ring members are counted twice, as with an indole type structures, where either the cyclic carbon ring, the heterocyclic ring or the double ring system may be optionally substituted with, 1) $C_{1-4}$ alkyl, or 2) $C_{2-4}$ alkenyl; and pharmaceutically acceptable salts thereof.

More preferred compounds are where at least one of one of the following combinations of two R groups, $R_1$ with $R_{20}$, $R_6$ with $R_5$, $R_{11}$ with $R_{10}$, and $R_{16}$ with $R_{15}$, taken together, form a heterocyclic ring structures where the heterocyclic ring nucleus contains 5, 6 or 7 members comprising one Nitrogen atom. Of these compounds preferred groups may have a 5 member ring that is a gamma lactam ring. Compounds where $R_2$, $R_4$, $R_7$, $R_9$, $R_{12}$, $R_{14}$, $R_{17}$, and $R_{19}$ are hydrogen and where $R_3$, $R_5$, $R_6$, $R_8$, $R_{10}$, $R_{11}$, $R_{13}$, $R_{15}$, $R_{16}$, $R_{18}$, $R_{20}$ are selected from H, $C_{1-4}$ alkyl ,benzyl, or are part of a lactam ring are also desired. Also preferred are compounds where $R_3$, $R_5$, $R_6$, $R_8$, $R_{10}$, $R_{11}$, $R_{13}$, $R_{15}$, $R_{16}$, $R_{18}$, $R_{20}$ are selected from methyl, isobutyl or benzyl, or are part of a lactam ring. Some preferred compounds contain 1, 2, or 4 lactam rings.

Also preferred are compounds where the heterocyclic ring nucleus is a 6 member delta lactam ring. Preferred groups of these compounds are where $R_2$, $R_4$, $R_7$, $R_9$, $R_{12}$, $R_{17}$, and $R_{19}$ are hydrogen and where $R_3$, $R_5$, $R_6$, $R_8$, $R_{10}$, $R_{11}$, $R_{13}$, $R_{15}$, $R_{16}$, $R_{18}$, $R_{20}$ are selected from H, $C_{1-4}$ alkyl ,benzyl, or are part of a lactam ring. More preferred are where $R_3$, $R_5$, $R_6$, $R_8$, $R_{10}$, $R_{11}$, $R_{13}$, $R_{15}$, $R_{16}$, $R_{18}$, $R_{20}$ mare selected from methyl, isobutyl or benzyl, or are part of a lactam ring. Frequently there is one delta lactam ring where $R_3$, $R_8$, $R_{13}$, and $R_{18}$ are all isobutyl and where $R_6$, $R_{11}$, and $R_{16}$ are methyl.

In this description any of the compounds marked with an * are compounds of this invention. Also included are pharmaceutical compositions comprising the compouds of this invention and medicaments and preparations of a medicament useful for the treatment of animals comprising the compounds of this invention.

ADDITIONAL DESCRIPTION OF THE INVENTION AND

DESCRIPTION OF THE PREFERRED EMBODIMENT(S)

Definitions

The compounds of this invention are identified in two ways: by descriptive names and textual descriptions and by reference to formulas and structures in Charts and reaction schemes having various chemical moieties. In appropriate situations, the proper stereochemistry is also represented in the structures. The following terms may also be used.

OPTIONALLY SUBSTITUTED The term "optionally substituted" shall mean a group or radical that is substituted with halogen, lower alkyl, mono- or di(lower alkyl)-substituted lower alkyl, (lower alkyl)thio, halo-substituted lower alkyl, amino-substituted lower alkyl, mono- or di(lower alkyl)-substituted amino, lower alkenyl, lower alkynyl, halogen, lower alkoxy, aryloxy, aryl(lower alkyl), hydroxy, cyano, amino, mono- and di(lower alkyl) amino, or nitro and the like.

ALKYL The parenthetical term ($C_{n-m}$ alkyl) is inclusive such that a compound of ($C_{1-8}$) would include compounds of 1 to 8 carbons and their isomeric forms. The various carbon moieties are aliphatic hydrocarbon radicals and includes branched or unbranched forms such as methyl, ethyl, n-propyl, isopropyl, n-butyl, isobutyl, sec-butyl, t-butyl, n-pentyl, isopentyl, n-hexyl, isohexyl, n-heptyl, isoheptyl, and n-octyl and isomeric forms thereof.

n-ALKYL The parenthetical term ($C_{n-m}$n-alkyl) is inclusive such that a compound of ($C_{1-8}$) would include compounds of 1 to 8 carbons in their straight chain unbranched form.

LOWER ALKYL The term "lower alkyl" refers to branched or unbranched saturated hydrocarbon radicals having from one to FIVE carbon atoms. Representatives of such groups are methyl, ethyl, n-propyl, isopropyl, n-butyl, isobutyl, sec-butyl, t-butyl, all the isomers of pentane and the like.

ALKOXY Alkoxy as represented by —$OR_1$ when $R_1$ is ($C_{1-8}$) alkyl refers to an alkyl radical which is attached to the remainder of the molecule by oxygen and includes branched or unbranched forms such as methoxy, ethoxy, n-propoxy, isopropoxy, n-butoxy, isobutoxy, sec-butoxy, t-butoxy, n-pentoxy, isopentoxy, n-hexoxy, isohexoxy, n-heptoxy, isoheptoxy, and n-octoxy and the like.

LOWER ALKOXY The term "lower alkoxy" denotes an alkyl group as defined above, attached to the patent molecular moiety through an oxygen atom. Representatives of such groups include methoxy, ethoxy, butyoxy, pentoxy and the like.

ALKENYL Alkenyl refers to a radical of an aliphatic unsaturated hydrocarbon having at least one double bond and includes both branched and unbranched forms such as ethenyl, (—CH=CH$_2$), 1-methyl-1-ethenyl, 1-propenyl, (—CH$_2$—CH=CH$_2$), 2-propenyl, 1-butenyl, 2-butenyl, 3-butenyl, 2-methyl-1-butenyl, 1-pentenyl, allyl, 3-pentenyl, 4-pentenyl, 1-methyl-4-pentenyl, 3-methyl-1-pentenyl, 3-methyl-allyl, 1-hexenyl, 2-hexenyl, 3-hexenyl, 4-hexenyl, 1-methyl-4-hexenyl, 3-methyl-1-hexenyl, 3-methyl-2-hexenyl, 1-heptenyl, 2-heptenyl, 3-heptenyl, 4-heptenyl, 1-methyl-4-heptenyl, 3-methyl-1-heptenyl, 3-methyl-2-heptenyl, 1-octenyl, 2-octenyl, or 3-octenyl and the like.

ALKYNYL Alkynyl refers to a monovalent branched or unbranched hydrocarbon radical containing at least one carbon-carbon triple bond, for example ethynyl, propynyl, and the like.

CYCLOALKYL The parenthetical term (C$_{n-m}$ cycloalkyl) is inclusive such that a compound of (C$_{3-10}$) would include radicals of a saturated cyclic hydrocarbon of 3 to 10 carbons in their cyclic chain. The term may also include alkyl-substituted cycloalkyl, such as cyclopropyl, 2-methylcyclopropyl, 2,2-dimethylcyclopropyl, 2,3 diethylcyclopropyl, 2-butylcyclopropyl, cyclobutyl, 2-methylcyclobutyl, 3-propylcyclobutyl, cyclopentyl, 2,2-dimethylcyclopentyl, cyclohexyl, cycloheptyl, cyclooctyl and cyclodecyl and the like. Each of these moieties may be substituted as appropriate.

HETEROALKYL "Heteroalkyl" refers to a aLkyls as described above, only where one, two or three non-adjacent carbon atoms are replaced by heteroatoms such as nitrogen, sulfur and oxygen.

ARYL (C$_{6-12}$) aryl, refers to a 6 to 12 carbon atom base structure, one or two fused or nonfused aromatic rings, that may be optionally substituted or substituted with one to 3 hydroxy, C$_1$–C$_3$ alkoxy, C$_1$–C$_3$ alkyl, trifluoromethyl, fluoro, chloro, or bromo groups. Examples of "aryl" are: phenyl, m-methylphenyl, p-trifluoromethylphenyl, α-naphthyl, β-naphthyl, (o-, m-, p-)tolyl, (o-, m-, p-)ethylphenyl, 2-ethyl-tolyl, 4-ethyl-o-tolyl, 5-ethyl-m-tolyl, (o-, m-, or p-)propylphenyl, 2-propyl-(o-, m-, or p-)-tolyl, 4-isopropyl-2,6-xylyl, 3-propyl-4-ethylphenyl, (2,3,4-, 2,3,6-, or 2,4,5-)trimethylphenyl, (o-, m-, or p-) fluorophenyl, (o-, m-, or p-trifluoromethyl)phenyl, 4-fluoro-2,5-xylyl, (2,4-, 2,5-, 2,6-, 3,4-, or 3,5-) difluorophenyl, (o-, m-, or p-)chlorophenyl, 2-chloro-p-tolyl, (3-, 4-, 5- or 6-) chloro-o-tolyl, 4-chloro-2-propylphenyl, 2-isopropyl-4-chlorophenyl, 4-chloro-3-f luorophenyl, (3- or 4-chloro-2-fluorophenyl, (o-, m-, or p-,)trifluorophenyl, (o-, m-, p-) ethoxyphenyl, (4- or 5-)chloro-2-methoxy-phenyl, and 2,4-dichloro(5- or 6-) methylphenyl and the like. Each of these moieties may be substituted as appropriate.

ALKYLARYL Alkylaryl refers to alkyl chains of one to 8 carbon atoms and isomeric forms thereof which are substituted with aryl groups of 6 to 12 carbon atoms as described above.

HETEROCYCLICS Examples of heterocyclics include: (2-, 3-, or 4-)pyridyl, imidazolyl, indolyl, N$^{in}$-formyl-indolyl, N$^{in}$—C$_2$–C$_5$alkyl-C(O)-indolyl, [1,2,4]-triazolyl, (2-, 4-, 5-)pyrimidinyl, (2-, 3-)thienyl, piperidinyl, pyrrolyl, pyrrolinyl, pyrrolidinyl, pyrazolyl, pyrazolinyl, pyrazolidinyl, imidazolyl, imidazolinyl, imidazolidinyl, pyrazinyl, piperazinyl, pyridazinyl, oxazolyl, oxazolidinyl, isoxazolyl, isoxazolidinyl, morpholinyl, thiazolyl, thiazolidinyl, isothiazolyl, isothiazolidinyl, quinolinyl, isoquinolinyl, benzimidazolyl, benzothiazolyl, benzoxazolyl, furyl, puryl, phenazyl, carbazolyl, thienyl, and benzothienyl, thienyl, indolyl, iso-quinolyl and the like. Each of these moieties may be substituted as appropriate.

HETEROARYL Heteroaryl refers to a one or two ring structure, of 5–12 ring atoms, where a minimum of one ring is aromatic, only where one, two or three non-adjacent carbon atoms are replaced by heteroatoms such as nitrogen, sulfur and oxygen. Examples can include pyridine, thiophene, furan, pyrimidine, 2-pyridyl, 3-pyridyl, 4-pyridyl, 2-pyrimidinyl, 4-pyrimidinyl, 5-pyrimidinyl, 3-pyridazinyl, 4-pryidazinyl, 3-pyrazinyl, 2-quinolyl, 3-quinolyl, 1-isoquinolyl, 3-isoquinolyl, 4-isoquinolyl, 2-quinazolinyl, 4-quinazolinyl, 2-quinoxaiinyl, 1-phthalazinyl, 2-imidazolyl, 4-imidazolyl, 3-isoxazolyl, 4-isoxazolyl, 5-isoxazolyl, 3-pyrazolyl, 4-pyrazolyl, 5-pyrazolyl, 2-oxazolyl, 4-oxazolyl, 5-oxazolyl,2-thiazolyl, 4-thiazolyl, 5-thiazolyl, 2-indolyl, 3-indolyl, 3-indazolyl, 2-benzoxazolyl, 2-benzothiazolyl, 2-benzimidazolyl, 2-benzofuranyl, 3-benzofuranyl, 2-furanyl, 3-furanyl, 2-thienyl, 3-thienyl, 2-pyrrolyl, 3-pyrrolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,2,4-triazol-5-yl, 1,2,3,4-tetrazol-5-yl, 5-oxazolyl, 1-pyrrolyl, 1-pyrazolyl, 1,2,3-triazol-1-yl, 1,2,4-triazol-1-tetrazolyl, 1-indolyl, 1-indazolyl, 2-isoindolyl, 1-purinyl, 3-isothiazolyl, 4-isothiazolyl and 5-isothiazolyl. Each of these moieties may be substituted as appropriate.

CHIRALITY It will be apparent to those skilled in the art that compounds of this invention may contain one or more chiral centers and may exist in optically active forms including cis-/trans- and/or R- and S- isomeric forms and mixtures thereof The scope of this invention includes all of these forms, the enantiomeric or dia-stereomeric forms of the compounds, including optically active forms, in pure form or as mixtures of enantiomers or diastereomers including cis-/trans-isomeric forms. The therapeutic properties of the compounds may to a greater or lesser degree depend on the stereochemistry of a particular compound. Resolution can be accomplished using resolving agents such as optically active dibenzoyltartaric acid, camphorsulfonic acid, bis-o-toluoyltartaric acid, tartaric acid, and diacetyl tartaric acid.

HALOGEN The term "halo-" and "halogen" refer to substituents selected from fluoro, chloro, bromo, iodo or trifluoromethyl.

Reagents and solvents

D-Malic acid was purchased from Lancaster Synthesis Inc.; N-BOC-N-methyl-L-leucine from Bachem Calif.; L-lactic acid sodium salt and 3-phenyl-D-lactic acid from Aldrich Chemical Company, Inc. The following solvents and reagents are dried over molecular sieves: THF (5A° sieves); methylene chloride (4A° sieves); TEA (4A° sieves).

Chromatography

Except where otherwise noted, chromatography is performed using Merck silica gel (230–400 mesh) contained in either a column or a sintered glass funnel. The product is eluted from the silica gel with varying concentrations of EtOAc in hexane.

Analytical data

NMR spectra are obtained on Bruker 300 MHz and 400 MHz instruments. Proton spectra of many of the intermediates showed the presence of rotamers on the nmr time scale. The isopropyl methyl groups of leucine often appeared as two or three sets of doublets because of rotamers and are designated (2d, 6H) and (3d, 6H), etc. Similar results are sometimes found with the tert-butyl methyl groups. Other protons are less likely to exhibit this effect.

Abbreviations

BOC tert-Butoxycarbonyl
BOP Benzotriazol-1-yloxytris(dimethylamino) phosphonium hexafluorophosphate
DCC N,N'-Dicyclohexylcarbodiimide
DEAD Diethylazodicarboxylate
DMAP 4-Dimethylaminopyridine
DPEA di-isopropylethylamine
LAH lithium aluminum hydride
LDA lithium diisopropylamide
NMM N-Methylmorpholine
PCC Pyridinium chlorochromate
PPTS Pyridinium p-toluene sulfonate
TBDMS tert-Butyldimethylsilyl
TEA Triethylamine
TFA Trifluoroacetic acid
THF is tetrahydrofuran
9-BBN-H or 9-BBN is 9-Borabicyclo[3.3.1]nonane dimer Pharmaceutical Preparations In clinical practice the compounds of the present invention will normally be administered orally, rectally, or by injection, in the form of pharmaceutical preparations comprising the active ingredient in association with a pharmaceutically acceptable carrier. The use and administration to a patient to be treated in the clinic would be readily apparent to a veterinarian or veterinary pharmacist of ordinary skill in the art.

Utility, Compositions and Administrations

Animals may be infected by several species of parasite at the same time since infection by one parasite may weaken the animal and make it more susceptible to infection by a second species of parasite. Thus a compound with a broad spectrum of activity is particularly advantageous in the treatment of these diseases. The compounds of this invention have unexpectedly high activity against these parasites, and in addition, the compounds are also active against Dirofilaria in dogs, Nematospiroides and Syphacia in rodents, biting insects and migrating diperous larvae such as *Hypoderma sp.* in cattle, and Gastrophilus in horses.

The instant compounds are also useful against endo and ecto parasites which cause parasitic diseases in humans. Examples of such endoparasites which infect man include gastrointestinal parasites of the genera Ancylostoma, Necator, Ascaris, Strongyloides, Trichinella, Capillaria, Trichuris, Enterobius, and the like. Other endoparasites which infect man are found in the blood or in other organs. Examples of such parasites are the filarial worms Wucheria, Brugia, Onchocerca, and the like as well as extra intestinal stages of the intestinal worms Strongyloides and Trichinella. Ectoparasites which parasitize man include arthropods such as ticks, fleas, mites, lice, and the like and, as with domestic animals, infections by these parasites can result in transmission of serious and even fatal diseases. The instant compounds are active against these endo and ecto parasites and in addition are also active against biting insects and other dipterous pests which annoy humans. The instant compounds when administered orally or parenterally are administered at a dosage rate of from 1.0 to 150 mg/kg of animal body weight.

The instant compounds are also useful against common household pests such as *Blatella sp.* (cockroach), *Tineola sp.* (clothes moth), *Attagenus sp.* (carpet beetle), *Musca domestica* (housefly) and against *Solenopsis Invicta* (imported fire ant).

The compounds are furthermore useful against agricultural pests such as aphids (*Acyrthiosiphon sp.*), locusts, and boll weevils as well as against insect pests which attack stored grains such as *Tribolium sp.* and against immature stages of insects living on plant tissue. The compounds are also useful as a nematocide for the control of soil nematodes which may be agriculturally important.

For use as an antiparasitic agent in animals the instant compounds may be administered internally either orally or by injection, or topically as a liquid drench or as a shampoo.

For oral administration, the compounds may be administered in capsule, tablet, or drench bolus form or alternatively they can be mixed in the animals feed. The capsules, tablets, and drenches boluses are comprised of the active ingredient in combination with an appropriate carrier vehicle such as starch, talc, magnesium stearate, or dicalcium phosphate. These unit dosage forms are prepared by intimately mixing the active ingredient with suitable finely-powdered inert ingredients including diluents, fillers, disintegrating agents, suspending agents, and/or binders such that a uniform mixture solution or suspension is obtained. An inert ingredient is one that will not react with the instant compounds and which is non toxic to the animal being treated.

Suitable inert ingredients include starch, lactose, talc, magnesium stearate, vegetable gums and oils, and the like. These formulations may contain a widely variable amount of the active and inactive ingredients depending on numerous factors such as the size and type of the animal species to be treated and the type and severity of the infection. The active ingredient may also be administered as an additive to the feed by simply mixing the compound with the feedstuff or by applying the compound to the surface of the feed. Alternatively the active ingredient may be mixed with an inert carrier and the resulting composition may then either be mixed with the feed or fed directly to the animal.

Suitable inert carriers include corn meal, citrus meal, fermentation residues, soya grits, dried grains and the like. The active ingredients are intimately mixed with these inert carriers by grinding, stirring, milling, or tumbling such that the final composition contains from 0.001 to 5.0% by weight of the active ingredient.

The compounds may alternatively be administered parenterally via injection of a formulation consisting of the active ingredient dissolved in an inert liquid carrier. Injection may be either intramuscular, intraruminal, intratracheal, or subcutaneous. The injectable formulation consists of the active ingredient mixed with an appropriate inert liquid carrier. Acceptable liquid carriers include the vegetable oils such as peanut oil, cotton seed oil, sesame oil and the like as well as organic solvents such as solketal, glycerol formal and the like. As an alternative, aqueous parenteral formulations may also be used. The vegetable oils are the preferred liquid carriers. The formulations are prepared by dissolving or suspending the active ingredient in the liquidcarrier such that the final formulation contains from 0.005 to 20% by weight of the active ingredient.

Topical application of the instant compounds is possible through the use of a liquid drench or a shampoo containing the instant compounds as an aqueous solution or suspension. These formulations generally contain a suspending agent such as bentonite and normally will also contain an antifoaming agent. Formulations containing from 0.005 to 20% by weight of the active ingredient are acceptable. Preferred formulations are those containing from 0.5 to 5% by weight of the instant compounds.

The instant compounds are primarily useful as antiparasitic agents for the treatment and/or prevention of helminthiasis in domestic animals such as cattle, sheep, horses, dogs, cats, goats, swine, and poultry. They are also useful in the prevention and treatment of parasitic infections of these animals by ectoparasites such as ticks, mites, lice, fleas and the like. They are also effective in the treatment of parasitic infections of humans. In treating such infections the compounds of this invention may be used individually or in combination with each other or with other unrelated antiparasitic agents. The dosage of the instant compounds required for best results depends on several factors such as the species and size of the animal, the type and severity of the infection, the method of administration and the compound used. Oral administration of the instant compounds at a dose level of from 1.0 to 150 mg per kg of animal body weight either in a single dose or in several doses spaced a few days apart, generally gives good results. A single dose of one of the instant compounds normally gives excellent control however repeat doses may be given to combat re-infection or for parasite species which are unusually persistent. The techniques for administering these compounds to animals are known to those skilled in the veterinary field.

The compounds of this invention may also be used to combat agricultural pests which attack crops either in the field or in storage. The compounds are applied for such uses as sprays, dusts, emulsions and the like either to the growing plants or the harvested crops. The techniques for applying these compounds in this manner are known to those skilled in the agricultural arts.

Activity of the Compounds

*Haemonchus contortus/Trichostrongylus colubriformis*/Jird Assay

This in vivo assay utilizes jirds infected with two important target parasites of ruminants, *H. contortus* and *T. colubriformis*. Activity is assessed against both species of parasites using the techniques outlined in G. A. Conder et al., J. Parsitol. 77, 621–623 (1991).

Minimum effective dose in mg/jird for 95% clearance of *Haemonchus contortus* and *Trichostrongylus colubriformis* from jirds inoculated per os with ~1,000 exsheathed, infective larvae of each parasite, treated per os with formula 10 on day 10 postinoculation (PI) and necropsied on day 13 post inoculation. The compounds of the invention all appear to show activity against *Haemonchus contortus* and *Trichostrongylus colubriformis*.

Compounds of the Invention

The compounds of the instant invention are described by the structure of Formula I, below:

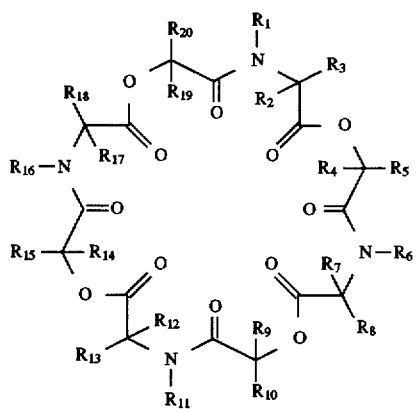

This disclosure comprises several different approaches, methods or procedures to create the compounds of this invention. These different approches, methods or procedures are described under various GROUPS which have various CHARTS. A GROUP is a more general scheme whose components are described by various CHARTS. A CHART refers both to a specific CHART, such as CHART A, where a reaction scheme may be shown and CHART or Chart or chart also refers to a series, a group, or a complex of reactions, such as the reactions of CHART A. The reactions may be described with words and/or with structures. Where structures are used it should be understood that obvious substitutions can be made. Among other compounds, the starting materials described in the next section below, and shown in Chart S as formula "J-21" can be used to create, "any suitable amino acid" which may be used in later charts and procedures to make all the compounds of this invention.

STARTING MATERIALS AND GENERAL PROCEDURES—CHARTS S1 AND S2

This section provides the general procedures for making the compounds described herein. The starting materials are also provided. The starting materials are shown in the "Table of Starting Materials" and in Charts S1 and S2. The general procedures for making all of the compounds are first provided in general form and then specific embodiments are provided in the Group Charts. By starting with the appropriate starting materials and then utilizing appropriate reactions as shown in the charts and discussed herein, all of the compounds described by the generic structures can be made.

The general procedure for removing a BOC protecting group, a general procedure for coupling peptides using dicyclohexylcarbodiimide, DCC, a general procedure for removing a benzyl protecting group and a general cyclization, a general procedure for formation of the macrocyclic ring is provided. These procedures and CHARTS S1 and S2 provide elementary and detailed descriptions of the reactions which are the basis of four general procedures used in the preparation of FORMULA I. These procedures are used multiple times to produce Formula I.

General Procedure for Removing a BOC Protecting Group

To remove the BOC protecting group the substrate is dissolved in $CH_2Cl_2$. Sufficient TFA is then added to give a 10–20% solution and the resulting reaction mixture stirred at room temperature under an atmosphere of dry nitrogen. The reaction progress is monitored by TLC. The reaction is usually done within 60 minutes, especially at the higher TFA concentration. The reaction mixture is slowly poured with vigorous stirring into a saturated solution of NaHCO₃ contained in a beaker. When CO₂ evolution has subsided, the mixture is transferred to a separatory funnel and the layers separated. The aqueous layer is extracted with CH₂Cl₂. The organic phases are combined, washed with water, dried over anhydrous Na₂SO₄, filtered and concentrated. Final drying under high vacuum gives the product which is used without further purification.

General Procedure for Removing a Benzyl Protecting Group

To remove the benzyl protecting group, the substrate is dissolved in absolute EtOH and 10% palladium on carbon added in a 5:1 weight ratio of substrate to catalyst (use of less catalyst dramatically increases reaction times and lowers yields). The reaction mixture is hydrogenolyzed for 3 hours at 45–50 psi, flushed with N₂ and filtered through Celite. The Celite cake is washed thoroughly with EtOH and the filtrates combined and concentrated. Residual EtOH which could interfere with any subsequent coupling reaction is removed by twice dissolving the product in EtOAc and concentrating. Drying under high vacuum at room temperature gives the product which is used without further purification.

When both BOC and benzyl protecting groups are to be removed from a molecule, we found it generally advantageous to remove the BOC group first, followed by removal of the benzyl group. This avoided the problem associated with retrieving the resulting zwitterionic peptide from an acidic medium.

General Procedure for Coupling Peptides Using Dicyclohexylcarbodiimide, DCC

The amine or alcohol is dissolved in THF along with one equivalent of the carboxylic acid under an atmosphere of dry nitrogen. The solution is cooled to 0° and one equivalent of DCC is added, usually in the form of a 1.0M solution of DCC in CH₂Cl₂. This is followed immediately by the addition of solid DMAP (5 mole %). A precipitate of dicyclohexylurea usually appeared within two minutes. The cooling bath is removed and the reaction mixture stirred at room temperature for two to three hours or until the starting alcohol or amine has been consumed as indicated by TLC. The reaction mixture is filtered to remove the urea and then concentrated. Any urea still present is removed by dissolving the crude product in ether and filtering a second time. The filtrate is concentrated and the product further purified by chromatography.

General Procedure for Removing a Benzyl Protecting Group, from Starting Materials Referring to both the Table of Starting Materials and Charts S, Formula J-7, Formula J-9, Formula J-13, Formula J-15 or Formula J-22 is dissolved in absolute EtOH and hydrogenolyzed for 4–16 hours at 15–45 psi over 10% palladium on charcoal. The reaction mixture is flushed with nitrogen, filtered, and concentrated to remove EtOH. The residue is dried under high vacuum to give Formula J-8, Formula J-10, Formula K-1, Formula J-16 or Formula J-23. By combining these four different reactions, Formula J-23 can be obtained and subsequently cyclized to give FORMULA I.

General Procedure for Removing a BOC Protecting Group, from Starting Materials Referring to both the Table of Starting Materials and Charts S, Formula J-7, Formula J-19, Formula J-13, Formula J-21, Formula K-2, is dissolved in CH₂Cl₂. Sufficient TFA is then added to give a 10–20% solution and the resulting reaction mixture stirred at room temperature under an atmosphere of dry nitrogen. The reaction progress is monitored by TLC. The reaction is usually done within 60 minutes, especially at the higher TFA concentration. The reaction mixture is slowly poured with vigorous stirring into a saturated solution of NaHCO₃ contained in a beaker. When CO₂ evolution has subsided, the mixture is transferred to a separatory funnel and the layers separated. The aqueous layer is extracted with CH₂Cl₂. The organic phases are combined, washed with water, dried over anhydrous Na2SO₄, filtered and concentrated. Final drying under high vacuum gives the following products which may be used without further purification, Formula J-8, Formula J-20, Formula J-14, Formula J-22, Formula K-3.

General Procedure for Coupling Peptides Using Dicyclohezylcarbodiimide, DCC from Starting Materials Referring to both the Table of Starting Materials and Charts S, the amine or alcohol of, a) Formula J-2, b) Formula J-6, c) Formula J-14, d) Formula J-18, e) Formula J-12, f) Formula J-20, g) Formula J-20, h) Formula K-3 is dissolved in THF along with one equivalent of the carboxylic acid of a) Formula J-1, b) Formula J-5, c) Formula J-10, d) Formula J-17, e) Formula J-11, f) Formula J-16, g) Formula K-1, h) Formula J-10 under an atmosphere of dry nitrogen. The solution is cooled to 0° and one equivalent of DCC is added, usually in the form of a 1.0M solution of DCC in CH₂Cl₂. This is followed immediately by the addition of solid DMAP (5 mole %). A precipitate of dicyclohexylurea usually appeared within two minutes. The cooling bath is removed and the reaction mixture stirred at room temperature for two to three hours or until the starting alcohol or amine has been consumed as indicated by TLC. The reaction mixture is filtered to remove the urea and then concentrated. Any urea still present is removed by dissolving the crude product in ether and filtering a second time. The filtrate is concentrated and the product for Formula a) J-3, b) Formula J-7, c) Formula J-15, d) Formula J-19, e) Formula J-13, f) Formula J-21, g) Formula K-2, h) Formula J-21 is further purified by chromatography.

General Cyclization Procedure for Formation of the Macrocyclic Ring

The amino acid (Formula J-23) is dissolved in methylene chloride to give a 5 mM solution. Triethyl amine (4 equivalents) and 1-methyl-2-chloropyridinium iodide (1.4 equivalents) are added at room temperature and the reaction mixture stirred for 16 h. The mixture is washed with IN HCl (aqueous solution) and the organic layer is separated, dried (MgSO₄) and concentrated. The residue is purified by silica gel chromatography (30% acetone in hexane) to give FORMULA L

General Procedure for Coupling Peptides Using BOP-Cl

The amine (or alcohol) and carboxylic acid were dissolved in CH₂Cl₂ and cooled to 0° under a nitrogen atmosphere. DPEA (or TEA) was added followed by BOP-Cl. The reaction mixture was stirred at room temperature for 24–48 h. The course of the reaction was monitored by TLC and more DPEA (or TEA) and BOP-CL were added if necessary. The reaction mixture was washed with sat NaHCO₃. The organic layer was filtered through Na₂SO₄ and dried over MgSO$_4$. Filtration through celite, concentration and drying under high vacuum gave the product.

General Procedure for Coupling Peptides such as Macrolactamization

The amine (or alcohol) and carboxylic acid, possibly parts of the same compound, are dissolved in CH$_2$Cl$_2$ to give a concentration of 1 mM and the solution is cooled to 0°. BOP (about 1.05 equivalents) reagent is added and stirred until completely dissolved. N-Methylmorpholine (about 1.05 equivalents) is added and the reaction mixture stirred at 0° for 30 min., and then for 3 days at room temperature. The reaction mixture is concentrated and then washed with saturated NH$_4$Cl. The layers are separated and the organic layer dried over MgSO$_4$, filtered through celite and concentrated. The residue is dissolved in EtOAc, and again concentrated to remove water. Drying under high vacum gives the product which is further purified by silica gel chromatography.

SPECIFIC REACTIONS AND EMBODIMENTS OF THE INVENTION

Without further direction, one skilled in the art should be able to produce the compounds of this invention. The following examples are provided to further illustrate and provide embodiments of this invention but they are not intended to limit the invention in any way. The CHARTS that show the structural description of the compounds, for all of the GROUPS follow the various textual sections.

THE REACTIONS OF GROUP 1

Unless indicated otherwise, everything in this section describes GROUP 1 reactions. The CHARTS show a series of compounds, called Formula, and various reactions that transform the compounds.

One of the compounds of this invention is described by Formula 14, shown in CHART C. In order to prepare Formula 14, two tetrapeptides are first prepared. Deprotection, followed by a coupling reaction will give the octapeptides which can be deprotected and cyclised to give the desired Formula 14.

Preparation of the first tetrapeptide, Formula 5, is shown in CHART A.

Preparation of the second tetrapeptide, Formula 7, is shown in CHART B.

Preparation of final products, are shown in subsequent charts.

The Reactions of Chart A (Group 1)

D-Phenyl lactate is treated with N,N,-diisopropyl-O-benzyl-isourea to give the corresponding benzyl ester, which is coupled with the leucine derivative to give 1. The Boc-group is removed with trifluoroacetic acid (TFA) to give 3.

The leucine derivative is coupled with methyl D-lactate to give the dipeptide (3), which is saponified to give the acid derivative (4). The two depsiptides, 3 and 4, are coupled in the presence of dicyclohexyl carbodiimide (DCC) and 4-methylaminopyridine (DMAP) to give 5.

The Reactions of Chart B (Group 1)

The proline derivative is coupled with methyl D-lactate to give 6, which is saponified to give 7. The dipeptide 7 is coupled with 3 to provide the tetrapeptide 8.

The Reactions of Chart C (Group 1)

Preparation of the final product, 14 or *722, is shown in CHART C. The tetrapeptide, 8 is hydrogenated to give 9. Removal of the Boc-group in 5 is achieved by treatment with TFA to give 10. The two tetradepsipeptides, 9 and 10, are coupled in the presence of diisopropyl carbdiimide (DIC) and 4-methylaminopyridine (DMAP) to give 11. After removal of the boc-group with TFA, 12 is hydrogenated to give 13, which is cyclised using BOP reagent to give 14 or *722.

The Reactions of Charts D (Group 1) & E (Group 1)

Preparation of the final product, 27 or *639, is shown in CHARTS D and E. To prepare 27 or *639, (shown in CHART E), one hexapeptide and one dipeptide are first made, the proper deprotection followed by a coupling reaction will give the octapeptides which can be deprotected and cyclised to give 27 or *6839. Chart D shows the preparation of the hexapeptide (21).

Chart E shows the preparation of the final product, 27 or *639. (L.)-Pipecolic acid is protected with the Boc-group and coupled with benzyl (L)-lactate using triphenyl phosphine (TPP) and diethylazodicarboxylate (DEAD) to give the corresponding didepsipeptide (22) with the correct configuration, which is deprotected to give the free amine (23). This free amine is condensed with 21 with the standard coupling condition (DIC/DMAP) to give the octadepsipeptide (24). Removal of the Boc-group gives 25, which is hydrogenated to give the amino acid 26. The octadepsipeptide 26 is cyclised with 2-chloro-N-methylpyridinium iodide and triethyl amine to give the final product 27 or *639.

The Reactions of Chart F (Group 1)

Preparation of 33 or *351 (and similarly *867) is shown in Chart F. (L)-Pipecolic acid derivative containing an extra benzene ring is coupled with benzyl (L)-lactate using triphenyl phosphine (TPP) and diethylazodicarboxylate (DEAD) to give the corresponding didepsipeptide (28) with the correct configuration, which is deprotected to give the free amine (29). This free amine is condensed with 21 with the standard coupling condition (DIC/DMAP) to give the octadepsipeptide (30). Removal of the Boc-group gives 31, which is hydrogenated to give the amino acid 32. The octadepsipeptide 32 is cyclised with 2-chloro-N-methylpyridinium iodide and triethyl amine to give the final product 33 or *351. Using similar procedures and reactions the final product *867 can also be made.

The Reactions of Charts G (Group 1) and H (Group 1)

CHARTS G and H show the preparation of 42 or *731. To prepare 42, one hexapeptide and one dipeptide are prepared and the proper deprotection and followed by coupling reaction will give the octapeptides which can be deprotected and cyclised, to give the desired. CHART G shows the preparation of the hexapeptide (38) and CHART H shows the preparation of the final product, 42. In CHART H the free amine, 23, is condensed with 38 using a standard coupling condition (DIC/DMAP) to give the octadepsipeptide (39). Removal of the Boc-group gives 40, which is hydrogenated to give the amino acid 41. The octadepsipeptide 41 is cyclised with 2-chloro-N-methylpyridinium iodide and triethyl amine to give the final product 42 or *731.

The Reactions of Chart I (Group 1)

CHART I shows the preparation of 46 or *798. The free amine, 29, is condensed with 38 with the standard coupling condition (DIC/DMAP) to give the octadepsipeptide (43). Removal of the Boc-group gives 44, which is hydrogenated to give the amino acid, 45. The octadepsipeptide, 45, is cyclised with 2-chloro-N-methylpyridinium iodide and triethyl amine to give the final product, 46 or *798.

ADDITIONAL DETAILS, DESCRIPTIONS AND PROCEDURES USED TO

PREPARE THE GROUP 1 COMPOUNDS, WITH EXAMPLES

Preparation of BOC-L-MeLeu-D-PhLac-OBn (1)

D-Phenyl lactic acid (6.82 g, 41.1 mmol) and N,N,-diisopropyl-O-benzyl-isourea (10.4 mL, 45.2 mmol, 1.1 equiv.) are dissolved in carbontetrachloride (120 mL). The mixture is heated to reflux for 1 h. After the mixture is cooled to room temperature, insoluble material is filtered off. The filtrate is mixed with methylene chloride (150 mL) and the resulting solution is treated with DIC (6.6 mL, 42.2 mmol), DMAP (1.22 g, 10 mmol), and Boc-L-MeLeu-OH (10.78 g, 44 mmol) at room temperature for 16 h. The precipitate is removed, the filtrate is concentrated. The residue is subjected to the silica-gel chromatography by elution of 5% ethyl acetate in hexane to give the title compound as an oil (15.35 g, 80% yield). $^1$H NMR (400 MHz, CDCl$_3$) 0.89 (d, 6H, J=6.09), 1.35–1.65 (m, 12H), 2.60 (s, 1.5H), 2.65 (s, 1.5H), 3.15 (m, 2H), 4.71 (m, 0.5H), 4.99 (m, 0.5H), 5.12 (m, 2H), 5.26 (m, 1H), 7.25 (m, 10H). Mass spec (EI) m/e 483 [M]. [a]$_D$=–13° (c 1.0, CHCl$_3$).

Preparation of BOC-L-MeLeu-Dac-OMe (2)

Boc-(L)-MeLecine (12.25 g, 50 mmol) is treated with DIC (8 mL, 50 mmol), DMAP (1.22 g, 10 mmol), and methyl D-lactate (6 g, 57.7 mmol) at room temperature for 1 h. The precipitate is removed, the filtrate is concentrated. The residue is partitioned methylene chloride (150 mL) and 0.3N HCl aqueous solution (100 mL). After the layer is separated, the organic layer is washed with 5% potassium carbonate aqueous solution (100 mL). The organic layer is separated, dried (MgSO$_4$), and concentrated to give the title compound as an oil (15 g, 91% yield). $^1$H NMR (400 MHz, CDCl$_3$) d 0.93–0.96 (m, 6H), 1.0–1.9 (m, 12H), 2.80 & 2.83 (s, 3H), 3.74 (s, 3H), 4.7–5.1 (m, 2H).

Preparation of L-MeLeu-D-PhLac-OBn (3)

BOC-L-MeLeu-D-PhLac-OBn (1, 9.7 g) is dissolved in CH$_2$Cl$_2$ containing 10% (v/v) TFA (300 mL). The reaction mixture is stirred 1.5 h and then slowly poured into saturated NaHCO$_3$ aqueous solution (300 mL) with rapid stirring. The mixture is transferred to a separatory funnel and shaken. The layers are separated, and the aqueous layer extracted with CH$_2$Cl$_2$. The organic layers are combined, washed with water, dried (Na$_2$SO$_4$), filtered, and concentrated to give the title compound as an oil (7.2 g, 94% yield). It is used without further purification.

Preparation of BOC-L-MeLeu-D-Lac-OH (4)

BOC-L-MeLeu-D-Lac-OMe (4, 15 g, 45.3 mmol) is dissolved in methanol (135 mL) and treated with 1N NaOH aqueous solution (50 mL, 50 mmol) at room temperature for 20 min. The mixture is poured into water (150 mL) and extracted with diethyl ether (2×100 mL). The aqueous layer is acidified by addition of 3N HCl aqueous solution (60 mL). The resulting mixture is extracted with methylene chloride (2×100 mL). The organic layer is separated, dried (MgSO$_4$), and concentrated to give the title compound as an oil (5 g, 35% yield). $^1$H NMR (400 MHz, CDCl$_3$) d 0.93–0.96 (m, 6H), 1.3–1.8 (m, 12H), 2.82 & 2.83 (s, 3H), 4.7–5.3 (m, 2H)·mL) and treated with 1N NaOH aqueous solution (50 mL, 50 mmol) at room temperature for 20 min. The mixture is poured into water (150 mL) and extracted with diethyl ether (2×100 mL). The aqueous layer is acidified by addition of 3N HCl aqueous solution (60 mL). The resulting mixture is extracted with methylene chloride (2×100 mL). The organic layer is separated, dried (MgSO$_4$), and concentrated to give the title compound as an oil (5 g, 35% yield). $^1$H NMR (400 MHz, CDCl$_3$) δ 0.93–0.96 (m, 6H), 1.3–1.8 (m, 12H), 2.82 & 2.83 (s, 3H), 4.7–5.3 (m, 2H).

Preparation of BOC-L-MeLeu-D-Lac-L-MeLeu-D-PhLac-OBn (5)

Boc-(L)-MeLeu-D-Lac-OH (4, 3.17 g, 10 mmol) is treated with DCC (1M in methylene chloride, 11 mL), DMAP (244 mg, 2 mmol), and L-MeLeu-D-PhLac-OBn (3, 3.66 g, 9.55 mmol) at room temperature for 1 h. The precipitate is removed, the filtrate is concentrated. The residue is subjected to the silica-gel chromatography by elution of 10% ethyl acetate in hexane to give the title compound as an oil (3.75 g, 58% yield). $^1$H NMR (400MHz, CDCl$_3$) δ 0.8–1.9 (m, 30H), 2.7–2.9 (m, 6H), 3.0–3.3 (m, 2H), 4.3–5.4 (m, 6H), 7.1–7.4 (m, 10H).

Preparation of BOC-L-Pro-D-Lac-OMe (6)

Boc-L)-Me-Proline (2.15 g, 10 mmol) is treated with DIC (1.6 mL, 10 mmol), DMAP (0.6 g, 5 mmol), and methyl D-lactate (1.2 g, 12 mmol) at room temperature for 1 h. The precipitate is removed, the filtrate is concentrated. The residue is partitioned methylene chloride (150 mL) and 0.3N HCl aqueous solution (100 mL). After the layer is separated, the organic layer is washed with 5% potassium carbonate aqueous solution (100 mL). The organic layer is separated, dried (MgSO$_4$), and concentrated to give the title compound as an oil (2.22 g, 74% yield). The structure of the product cab be confirmed by nuclear magnetic resonance spectroscopy and mass spectrometry.

Preparation of BOC-L-Pro-D-Lac-OH (7)

BOC-L-Pro-D-Lac-OMe (6, 2.1 g, 7.0 mmol) is dissolved in methanol (25 mL) and treated with 1N NaOH aqueous solution (8 mL, 8 mmol) at room temperature for 20 min. The mixture is poured into water (20 mL) and extracted with diethyl ether (2×30 mL). The aqueous layer is acidified by addition of 1N HCl aqueous solution (40 mL). The resulting mixture is extracted with methylene chloride (3×30 mL). The organic layer is separated, dried (MgSO$_4$), and concentrated to give the title compound as an oil (1.4 g, 70% yield); slowly solidified. $^1$H NMR (400MHz, CDCl$_3$) δ 1.42 & 1.46 (s, 9H), 1.54 (d, 3H), 1.8–2.5 (m, 4H), 3.4–3.7 (m, 2H), 4.3–4.4 (m, 1H), 5.12 & 5.28 (q, 1H).

Preparation of BOC-L-Pro-D-Lac-L-MeLeu-D-PhLac-OBn (8)

Boc-(L)-Pro-D-Lac-OH (7, 5.47 g, 19 mmol) is treated with DIC (3.27 mL, 20.9 mmol), DMAP (464 mg, 3.8 mmol), and L-MeLeu-D-PhLac-OBn (3, 7.2 g, 19 mmol) at room temperature. The mixture is stirred for 16 h. The precipitate is removed, the filtrate is concentrated. The residue is subjected to the silica-gel chromatography by elution of 10% ethyl acetate in hexane to give the title compound as an oil (10 g, 82% yield). $^1$H NMR (400MHz, CDCl$_3$) δ 0.9–2.3 (m, 23H), 2.7–2.9 (m, 3H), 3.0–3.6 (m, 4H), 4.3–5.4 (m, 6H), 7.1–7.4 (m, 10H).

Preparation of BOC-L-Pro-D-Lac-L-MeLeu-D-PhLac-OH (9)

BOC-L-Pro-D-Lac-L-MeLeu-D-PhLac-OBn (5.0 g, 7.7 mmol) is dissolved in absolute EtOH (100 mL) and hydrogenolyzed for four hours at 3 atm (40 psi) over 10% palladium on charcoal (1.2 g). The reaction mixture is flushed with nitrogen, filtered, and concentrated to remove EtOH. The residue is dried under high vacuum to give the title compound (4.18 g, 98%) as a solid. $^1$H NMR (400MHz, CDCl$_3$) δ 0.8–2.3 (m, 23H), 2.9–3.6 (m, 7H), 4.1–5.7 (m, 4H), 7.2–7.4 (m, 5H).

Preparation of L-MeLeu-D-Lac-L-MeLeu-D-PhLac-OBn (10)

BOC-L-MeLeu-D-Lac-L-MeLeu-D-PhLac-OBn (9, 1.2 g, 1.8 mmol) is dissolved in CH$_2$Cl$_2$ containing 10% (v/v) TFA (30 mL). The reaction mixture is stirred 1.5 h and then slowly poured into saturated NaHCO$_3$ aqueous solution (30 mL) with rapid stirring. The mixture is transferred to a separatory funnel and shaken. The layers are separated, and the aqueous layer extracted with CH$_2$Cl$_2$. The organic layers are combined, washed with water, dried (Na$_2$SO$_4$), filtered, and concentrated to give the title compound as an oil (0.92 g, 90% yield). It is used without further purification.

Preparation of BOC-L-Pro-D-Lac-L-MeLeu-D-PhLac-L-MeLeu-D-Lac-L-MeLeu-D-PhLac-OBn (11)

BOC-L-Pro-D-Lac-L-MeLeu-D-PhLac-OH (9, 0.82 g, 1.46 mmol) is treated with DCC (1M, 1.65 mL, 1.65 mmol), DMAP (40 mg, 0.33 mmol), and L-MeLeu-D-Lac-L-MeLeu-D-PhLac-OBn (10, 0.895 g, 1.54 mmol) at room temperature. The mixture is stirred for 16 h. The precipitate is removed, the filtrate is concentrated. The residue is subjected to the silica-gel chromatography by elution of 10% to 20% acetone in hexane to give the title compound as a solid (1 g, 61% yield). $^1$H NMR (400MHz, CDCl$_3$) δ 0.8–2.3 (m, 42H), 2.7–3.6 (m, 15H), 4.3–5.6 (m, 10H), 7.1–7.5 (m, 15H).

Preparation of L-Pro-D-Lac-L-MeLeu-D-PhLac-L-MeLeu-D-Lac-L-MeLeu-D-PhLac-OBn (12)

BOC-L-Pro-D-Lac-L-MeLeu-D-PhLac-L-MeLeu-D-Lac-L-MeLeu-D-PhLac-OBn (11, 1.0 g) is dissolved in CH$_2$Cl$_2$ containing 10% (v/v) TFA (30 mL). The reaction mixture is stirred 1.5 h and then slowly poured into saturated K$_2$CO$_3$ aqueous solution (30 mL) with rapid stirring. The mixture is transferred to a separatory funnel and shaken. The layers are separated, and the aqueous layer extracted with CH$_2$Cl$_2$. The organic layersare combined, washed with water, dried (Na$_2$SO$_4$), filtered, and concentrated to give the title compound as an oil (0.84 g, 90% yield). It is used without further purification.

Preparation of L-Pro-D-Lac-L-MeLeu-D-PhLac-L-MeLeu-D-Lac-L-MeLeu-D-PhLac-OH (13)

L-Pro-D-Lac-L-MeLeu-D-PhLac-L-MeLeu-D-Lac-L-MeLeu-D-PhLac-OBn (0.80 g,) is dissolved in absolute EtOH (100 mL) and hydrogenolyzed for four hours at 3 atm (40 psi) over 10% palladium on charcoal (0.2 g). The reaction mixture is flushed with nitrogen, filtered, and concentrated to remove EtOH. The residue is dried under high vacuum to give the title compound (0.7 g, 95%) as a solid. It is used without further purification.

Example 1

Preparation of cyclo(D-2-hydroxy-3-phenylpropanoyl-L-prolyl-D-2-hydroxypropanoyl-N-methyl-L-leucyl-D-2-hydroxy-3-phenylpropanoyl-N-methyl-L-leucyl-D-2-hydroxypropanoyl-N-methyl-L-leucyl) (14 or *722)

The amino acid (13, 550 mg, 0.59 mmol) is dissolved in methylene chloride (100 mL) and treated with triethyl amine (0.32 mL, 2.32 mmol, 4 equiv.) and 1-methyl-2-chloropyridinium iodide (162 mg, 0.63 mmol,1.1 equiv.) at room temperature. The mixture is stirred for 16 h. After the volatile components are removed in vacuo, the residue is purified by silica gel chromatography (50% ethyl acetate in hexane) to give the title compound (60 mg, 12%) as a solid. $^1$H NMR (400 MHz, CDCl$_3$) δ 0.8–2.4 (m, 37H), 2.7–3.3 (m, 15H), 3.5–6.0 (m, 8H) 7.2–7.4 FAB HRMS m/z (M$^+$+H, C$_{50}$H$_{70}$N$_4$O$_{12}$+H) calc 941.4888 obsd 941.4905.

Preparation of BOC-L-MeLeu-D-Lac-OBn (15)

Triphenylphosphine (TPP, 28 g, 0.106 mol), N-methyl-Boc-L-leucine (24.5 g, 0.1 mol), and benzyl (L)-lactate (20 g, 0.11 mol) are dissolved in diethyl ether (250 mL). The resulting mixture is treated with DEAD (17.4 mL in 50 mL of diethyl ether) at room temperature over 20 min. The mixture is stirred for an additional 1h and the precipitate is removed by filtration. The filtrate is concentrated and the residue is purified by silica gel chromatography (10% ethyl acetate in hexane) to give the title compound (45 g, 72%) as an oil. $^1$H NMR (400 MHz, CDCl$_3$) δ 0.9–1.8 (m, 21H), 2.74 & 2.77 (s, 3H), 4.7–5.3 (m, 4H), 7.2–7.5 (m, 5H). Mass spec (EI) m/e 407 [M]. Anal. Calcd for C$_{22}$H$_{33}$NO$_6$: C, 64.84; H, 8.16; N, 3.44. Found: C, 64.96, H, 8.39; N, 3.80. [a]$_D$=−22° (c 0.49, CHCl$_3$).

Preparation of BOC-L-MeLeu-D-Lac-OH (16)

BOC-L-MeLeu-D-Lac-OBn (13.9 g, 34 mmol) is dissolved in absolute EtOH (100 mL) and hydrogenolyzed for 24 h at 3 atm (40 psi) over 10% palladium on charcoal (2.5 g). The reaction mixture is flushed with nitrogen, filtered, and concentrated to remove EtOH. The residue is dried under high vacuum to give the title compound (10 g, 93%) as an oil. $^1$H NMR (400MHz, CDCl$_3$) δ 0.9–1.8 (m, 21H), 2.82 (s, 3H), 4.7–5.2 (m, 2H), 8.1 (br s, 1H).

Preparation of L-MeLeu-D-Lac-OBn (17)

BOC-L-MeLeu-D-Lac-OBn (15, 2.55 g, 6.26 mmol) is dissolved in CH$_2$Cl$_2$ containing 10% (v/v) TFA (100 mL). The reaction mixture is stirred 50 minutes and then slowly poured into saturated NaHCO$_3$ with rapid stirring. The mixture is transferred to a separatory funnel and shaken. The layers are separated, and the aqueous layer extracted with CH$_2$Cl$_2$. The organic layers are combined, washed with water, dried (Na$_2$SO$_4$), filtered, and concentrated. Drying under high vacuum gives the title compound (17, 1.70 g, 89%) as a clear, pale-yellow oil. $^1$H NMR (300 MHz, CDCl$_3$) δ 0.90 (d, 3H, J=7.00), 0.92 (d, 3H, J=6.96), 1.47 (td, 2H, J=1.8, 6.94), 1.52 (d, 3H, J=7.09), 1.62 (brd s, 1H), 1.72 (septet, 1H, J=6.73), 2.35 (s, 3H), 3.27 (t, 1H, J=7.30), 5.18 (m, 3H), 7.35 (m, 5H). It is used without further purification.

Preparation of BOC-L-MeLeu-D-Lac-L-MeLeu-D-Lac-OBn (18)

Boc-(L)-MeLeu-D-Lac-OH (16, 28 g, 88 mmol) is dissolved in methylene chloride (250 mL) and treated with DIC (13.6 ml, 96.8 mmol), DMAP (1.2 g, 10 mmol), and L-MeLeu-D-Lac-OBn (17, 27 g, 88 mmol) at 0° C. The mixture is slowly warmed to room temperature and stirred for 16 h. The precipitate is removed, the filtrate is concentrated. The residue is subjected to the silica-gel chromatography by elution of 20% ethyl acetate in hexane to give the title compound as an oil (47.5 g, 88% yield). $^1$H NMR (400MHz, CDCl$_3$) δ 0.8–1.8 (m, 39H), 2.8–3.0 (m, 6H), 4.4–5.4 (m, 6H), 7.2–7.4 (m, 5H).

Preparation of BOC-L-MeLeu-D-Lac-L-MeLeu-D-Lac-OH (19)

BOC-L-MeLeu-D-Lac-L-MeLeu-D-Lac-OBn (22 g, 36.3 mmol) is dissolved in absolute EtOH (130 mL) and hydrogenolyzed for 17 hours at 3 atm (40 psi) over 10% palladium on charcoal (3.8 g). The reaction mixture is flushed with nitrogen, filtered, and concentrated to remove EtOH. The residue is dried under high vacuum to give the title compound (18.3 g, 96%) as a semi-solid. It is used without further purification.

Preparation of BOC-L-MeLeu-D-Lac-L-MeLeu-D-Lac-L-MeMeu-D-Lac-OBn (20)

Boc-(L)-MeLeu-D-Lac-L-MeLeu-Lac-OH (19, 4.4 g, 8.5 mmol) is dissolved in methylene chloride (50 mL) and treated with DIC (1.4 ml, 9.4 mmol), DMAP (0.1 g, 0.8 mmol), and L-MeLeu-D-Lac-OBn (17, 2.6 g, 8.5 mmol) at 0° C. The mixture is slowly warmed to room temperature and stirred for 16 h. The precipitate is removed, the filtrate is concentrated. The residue is subjected to the silica-gel chromatography by elution of 20% acetone in hexane to give the title compound as an oil (4.7 g, 68% yield). $^1$H NMR (400 MHz, CDCl$_3$) δ 0.8–1.9 (m, 45H), 2.8–3.0 (m, 9H), 4.1–5.4 (m, 8H), 7.2–7.4 (m, 5H).

Preparation of BOC-L-MeLeu-D-Lac-L-MeLeu-D-Lac-L-MeMeu-D-Lac-OH (21)

BOC-L-MeLeu-D-Lac-L-MeLeu-D-Lac-L-MeLeu-D-Lac-OBn (20, 3.3 g, 4.1 mmol) is dissolved in absolute EtOH (100 mL) and hydrogenolyzed for 17 hours at 3 atm (40 psi) over 10% palladium on charcoal (0.7 g). The reaction mixture is flushed with nitrogen, filtered, and concentrated to remove EtOH. The residue is dried under high vacuum to give the title compound (2.8 g, 95%) as a solid. $^1$H NMR (400MHz, CDCl$_3$) δ 0.8–1.9 (m, 45H), 2.8–3.1 (m, 9H), 4.5–5.5 (m, 6H). FAB HRMS m/z (M$^+$+Na, C$_{35}$H$_{61}$N$_3$O$_{12}$+Na) calc 738.4153 obsd 738.4135.

Preparation of BOC-L-Pip-D-Lac-OBn (22)

(L)-Pipecolic acid (517 mg, 4 mmol) is suspended in THF (20 mL) and treated with diethyl dicarbonate (960 mg, 4.4 mmol) and triethyl amine (1.1 mL, 8 mmol). The mixture is refluxed for 2 h and cooled to room temperature. The mixture is stirred for 16 h. The precipitate is filtered off and the filtrate is concentrated. The residue is redissolved in methylene chloride (30 mL) and washed with 0.5N HCl (aqueous solution, 20 mL). The organic layer is separated, dried (MgSO$_4$), and concentrated to give Boc-pipecolic acid(640 mg, 70% yield). It was used without further purification.

Triphenylphosphine (TPP, 880 mg, 3.36 mmol), Boc-pipecolic acid(640 mg, 2.8 mmol), and benzyl (L)-lactate (0.5 g, 2.8 mmol) are dissolved in diethyl ether (20 mL). The resulting mixture is treated with DEAD (0.5 mL, 3.17 mmol in 5 mL of diethyl ether) at room temperature over 20 min. The mixture is stirred for an additional 1h and the precipitate is removed by filtration. The filtrate is concentrated and the residue is purified by silica gel chromatography (10% ethyl acetate in hexane) to give the title compound (0.37 g, 24%) as an oil. $^1$H NMR (400 MHz, CDCl$_3$) δ 1.1–2.3 (m, 18H), 2.8–3.0 (m, 1H), 3.8–4.1(m, 1H), 4.7–5.2 (m,4H) 7.2–7.4 (m, 5H). FAB HRMS m/z (M$^+$+H, C$_{21}$H$_{29}$N$_1$O$_6$+H) calc 392.2073 obsd 392.2086.

Preparation of L-Pip-D-Lac-OBn (23)

BOC-L-Pip-D-Lac-OBn (22, 370 mg,, 0.95 mmol) is dissolved in CH$_2$Cl$_2$ containing 10% (v/v) TFA (15 mL). The reaction mixture is stirred 50 minutes and then slowly poured into saturated NaHCO$_3$ with rapid stirring. The mixture is transferred to a separatory funnel and shaken. The layers are separated, and the aqueous layer extracted with CH$_2$Cl$_2$. The organic layers are combined, washed with water, dried (Na2SO$_4$), filtered, and concentrated. Drying under high vacuum gives the title compound (23, 0.204 g, 74%) as a clear, pale-yellow oil. It is used without further purification.

Preparation of BOC-L-MeLeu-D-Lac-L-MeLeu-D-Lac-L-MeLeu-D-Lac-L-Pip-D-Lac-OBn (24)

BOC-L-MeLeu-D-Lac-L-MeLeu-D-Lac-L-MeLeu-D-Lac-OH (21, 480 mg, 0.67 mmol) is dissolved in methylene chloride (20 mL) and treated with DIC (0.125 ml, 1 mmol), DMAP (12 mg, 0.1 mmol), and L-Pip-D-Lac-OBn (23, 0.204 g, 0.7 mmol) at 0° C. The mixture is slowly warmed to room temperature and stirred for 16 h. The precipitate is removed, the filtrate is concentrated. The residue is subjected to the silica-gel chromatography by elution of 20% acetone in hexane to give the title compound as an oil (273 mg, 41% yield). $^1$H NMR (400 MHz, CDCl$_3$) δ 0.8–2.3 (m, 45H), 2.7–3.1 (m, 9H), 3.3–5.4 (m, 8H), 7.2–7.4 (m, 5H).

Preparation of L-MeLeu-D-Lac-L-MeLeu-D-Lac-L-MeLeu-D-Lac-L-Pip-D-Lac-OBn (25)

BOC-L-MeLeu-D-Lac-L-MeLeu-D-Lac-L-MeLeu-D-Lac-L-Pip-D-Lac-OBn (24, 270 mg) is dissolved in CH$_2$Cl$_2$ containing 10% (v/v) TFA (20 mL). The reaction mixture is stirred 1.5 h and then slowly poured into saturated K$_2$CO$_3$ aqueous solution (20 mL) with rapid stirring. The mixture is transferred to a separatory funnel and shaken. The layers are separated, and the aqueous layer extracted with CH$_2$Cl$_2$. The organic layers are combined, washed with water, dried (Na$_2$SO$_4$), filtered, and concentrated to give the title compound as an oil (0.2 g, 83% yield). It is used without further purification.

Preparation of L-MeLeu-D-Lac-L-MeLeu-D-Lac-L-MeLeu-D-Lac-L-Pip-D-Lac-OH (26)

L-MeLeu-D-Lac-L-MeLeu-D-Lac-L-MeLeu-D-Lac-L-Pip-D-Lac-OBn (25, 200 mg) is dissolved in absolute EtOH (50 mL) and hydrogenolyzed for four hours at 3 atm (40 psi) over 10% palladium on charcoal (0.1 g). The reaction mixture is flushed with nitrogen, filtered, and concentrated to remove EtOH. The residue is dried under high vacuum to give the title compound (0.165 g, 89%) as a solid. $^1$H NMR (400 MHz, CDCl$_3$) δ 0.8–1.9 (m, 35H), 2.3–3.1 (m, 10H), 3.5–5.6 (m, 10H). It is used without further purification.

Example 2

Preparation of cvlo(D-2-hydroxypropanoyl-L-pipecolyl-D-2-hydroxypropanoyl-N-methyl-L-leucyl-D-2-hydroxypropanoyl-N-methyl-L-leucyl-D-2-hydroxypropanoyl-N-methyl-L-leucyl) (27 or *639)

The amino acid (26, 150 mg, 0.19 mmol) is dissolved in methylene chloride (40 mL) and treated with triethyl amine (0.12 mL, 0.87 mmol) and 1-methyl-2-chloropyridinium iodide (61 mg, 0.24 mmol, 1.2 equiv.) at room temperature. The mixture is stirred for 16 h. The mixture is washed with 1N HCl (aqueous solution, 30 mL) and the organic layer is separated, dried (MgSO$_4$) and concentrated. The residue is purified by silica gel chromatography (30% acetone in hexane) to give the title compound (50 mg, 34%) as a solid. $^1$H NMR (400 MHz, CDCl$_3$) δ 0.8–1.9 (m, 35H), 2.3–3.1 (m, 10H), 3.5–5.6 (m, 10H). FAB HRMS m/z (M$^+$+H, C$_{39}$H$_{64}$N$_4$O$_{12}$+H) calc 781.4599 obsd 781.4576.

Preparation of BOC-L-Tic-D-Lac-OBn (28)

Triphenylphosphine (TPP, 0.57 g, 2.18 mmol), Boc-L-Tic-OH (N-a-Boc-L-tetrahydroquinoline-3-carboxylic acid from Peninsula Lab. Inc., 554 mg, 2 mmol), and benzyl (L)-lactate (360 mg, 2 mmol) are dissolved in diethyl ether (20 mL). The resulting mixture is treated with DEAD [0.35 mL (2.33 mmol) in 3 mL of diethyl ether] at room temperature over 20 min. The mixture is stirred for an additional 1 h and the precipitate is removed by filtration. The filtrate is concentrated and the residue is purified by silica gel chromatography (10% ethyl acetate in hexane) to give the title compound (0.55 g, 63%) as an oil. $^1$H NMR (400 MHz, CDCl$_3$) δ 1.3–1.7 (m, 12H), 3.1–3.4 (m, 2H), 4.5–5.3 (m, 6H), 7.0–7.4 (m, 9H). FAB HRMS m/z (M$^+$+H, C$_{25}$H$_{29}$N$_1$O$_6$+H) calc 440.2073 obsd 440.2087.

Preparation of L-Tic-D-Lac-OBn (29)

BOC-L-Tic-D-Lac-OBn (28, 241 mg,, 0.55 mmol) is dissolved in CH$_2$Cl$_2$ containing 10% (v/v) TFA (15 mL). The reaction mixture is stirred 50 minutes and then slowly poured into saturated NaHCO$_3$ with rapid stirring. The mixture is transferred to a separatory funnel and shaken. The layers are separated, and the aqueous layer extracted with CH$_2$Cl$_2$. The organic layers are combined, washed with water, dried (Na$_2$SO$_4$), filtered, and concentrated. Drying under high vacuum gives the title compound (29, 0.154 g, 82%) as a clear, pale-yellow oil. It is used without further purification.

Preparation of BOC-L-MeLeu-D-Lac-L-MeLeu-D-Lac-L-MeLeu-D-Lac-L-Tic-D-Lac-OBn (30)

BOC-L-MeLeu-D-Lac-L-MeLeu-D-Lac-L-MeLeu-D-Lac-OH (21, 341 mg, 0.48 mmol) is dissolved in methylene chloride (20 mL) and treated with DIC (0.1 ml, 0.8 mmol), DMAP (4 mg, 0.03 mmol), and L-Tic-D-Lac-OBn (29, 0.154 g, 0.45 mmol) at 0° C. The mixture is slowly warmed to room temperature and stirred for 16 h. The precipitate is removed, the filtrate is concentrated. The residue is subjected to the silica-gel chromatography by elution of 20% acetone in hexane to give the title compound as a semi-solid (350 mg, 75% yield). $^1$H NMR (400 MHz, CDCl$_3$) δ 0.8–1.9 (m, 48H), 2.7–3.4 (m, 11H), 3.7–5.5 (m, 12H), 7.0–7.4 (m, 9H).

Preparation of L-MeLeu-D-Lac-L-MeLeu-D-Lac-L-MeLeu-D-Lac-L-Tic-D-Lac-OBn (31)

BOC-L-MeLeu-D-Lac-L-MeLeu-D-Lac-L-MeLeu-D-Lac-L-Tic-D-Lac-OBn (30, 350 mg) is dissolved in CH$_2$Cl$_2$ containing 10% (v/v) TFA (30 mL). The reaction mixture is stirred 1.5 h and then slowly poured into saturated K$_2$CO$_3$ aqueous solution (30 mL) with rapid stirring. The mixture is transferred to a separatory funnel and shaken. The layers are separated, and the aqueous layer extracted with CH$_2$Cl$_2$. The organic layers are combined, washed with water, dried (Na$_2$SO$_4$), filtered, and concentrated to give the title compound as a semi-solid (0.28 g, 89% yield). It is used without further purification.

Preparation of L-MeLeu -D-Lac-L-MeLeu-D-Lac-L-MeLeu-D-Lac-L-Tic-D-Lac-OH (32)]

L-MeLeu-D-Lac-L-MeLeu-D-Lac-L-MeLeu-D-Lac-L-Tic-D-Lac-OBn (31, 280 mg) is dissolved in absolute EtOH (50 mL) and hydrogenolyzed for four hours at 3 atm (40 psi) over 10% palladium on charcoal (0.1 g). The reaction mixture is flushed with nitrogen, filtered, and concentrated to remove EtOH. The residue is dried under high vacuum to give the title compound (0.2 g, 80%) as a solid. It is used without further purification.

Example 3 and 3b

Preparation of cylo(D-2-hydroxypropanoyl-L-N-α-tetrahydroquinoline-3-carboxyl-D-2-hydroxypropanoyl-N-methyl-L-leucyl-D-2-hydroxypropanoyl-N-methyl-L-leucyl-D-2-hydroxypropanoyl-N-methyl-L-leucyl) (33 or *351)

The amino acid (32, 200 mg, 0.24 mmol) is dissolved in methylene chloride (40 mL) and treated with triethyl amine (0.12 mL, 0.87 mmol) and 1-methyl-2-chloropyridinium iodide (74 mg, 0.29 mmol, 1.2 equiv.) at room temperature. The mixture is stirred for 16 h. The mixture is washed with 1N HCl (aqueous solution, 30 mL) and the organic layer is separated, dried (MgSO$_4$) and concentrated. The residue is purified by silica gel chromatography (30% acetone in hexane) to give the title compound (100 mg, 50%) as a solid. $^1$H NMR (400MHz, CDCl$_3$) δ 0.8–1.9 (m, 39H), 2.7–4.0 (m, 11H), 4.5–5.8 (m, 10H), 7.0–7.3 (m, 4H). FAB HRMS m/z (M$^+$+H, C$_{43}$H$_{64}$N$_4$O$_{12}$+H) calc 829.4599 obsd 829.4587.

Using procedures similar to the procedures provided in Example 3 above, the compound shown as *867 can also be constructed.

Preparation of BOC-L-MeLeu-D-PhLac-OH (34)

BOC-L-MeLeu-D-Lac-L-MeLeu-D-Lac-OBn (6.02 g, 12.4 mmol) is dissolved in absolute EtOH (100 mL) and hydrogenolyzed for seven hours at 3 atm over 10% palladium on charcoal (667 mg). The reaction mixture was flushed with nitrogen, filtered through celite and concentrated to remove EtOH. The residue was taken up in Et$_2$O, washed with water (4×), dried (MgSO$_4$), and filtered. The filtrate was concentrated and dried under high vacuum to 34 (4.70 g, 96%) as a clear, colorless, viscous oil. $^1$H NMR (300 MHz, CDCl$_3$) δ 0.91 (m, 6H), 1.3–1.9 (m, 12H), 2.5–3.0 (m, 3H), 3.0–3.3 (m, 2H), 4.65 (m, 1H), 4.90 (m, 1H), 5.30 (m, 1H), 7.25 (m, 5H). This material was used without further purification.

Preparation of BOC-L-MeLeu-D-PhLac-L-MeLeu-D-Lac-OBn (35)

Formula 34 (2.18 g, 5.53 mmol) and 17 (1.70 g, 5.53 mmol) are dissolved in dry CH$_2$Cl$_2$ (40 mL). DMAP (34 mg, 0.28 mmol) is added at room temperature followed by DCC (1.26 g, 6.08 mmol). A precipitate of dicyclohexylurea forms very quickly following addition of DCC. The reaction mixture is stirred 60 minutes and then concentrated. The residue is taken up in Et$_2$O, filtered, and concentrated. This was repeated to remove all insoluble material giving a clear, light yellow oil. This is further purified by silica gel chromatography (10% EtOAc in hexane) to give 35 (2.15 g, 57%) as a clear, colorless oil. $^1$H NMR (300 MHz, CDCl$_3$) δ 0.93 (m, 12H), 1.3–1.8 (m, 18H), 2.5–3.0 (m, 6H), 3.0–3.2 (m, 2H), 4.69 (m, 0.5H), 4.96 (m, 0.5), 5.0–5.2 (m, 3H), 5.28 (m, 1H), 5.45 (m, 1H), 7.30 (m, 10H). Mass spec (EI) m/e 682 [M].

Preparation of BOC-L-MeLeu-D-PhLac-L-MeLeu-D-Lac-OH (36)

35 (6.83 g, 10 mmol) is dissolved in absolute EtOH (100 mL) and hydrogenolyzed for 17 hours at 3 atm (40 psi) over 10% palladium on charcoal (2.1 g). The reaction mixture is flushed with nitrogen, filtered, and concentrated to remove EtOH. The residue is dried under high vacuum to give 36 (5.67 g, 96%) as a semi-solid. It is used without further purification.

Preparation of BOC-L-MeLeu-D-PhLac-L-MeLeu-D-Lac-L-MeMeu-D-PhLac-OBn (37) Boc-(L)-MeLeu-D-PhLac-L-MeLeu-Lac-OH (36, 4.0 g, 6.8 mmol) is dissolved in methylene chloride (50 mL) and treated with DIC (1.17 ml, 7.5 mmol), DMAP (0.1 g, 0.8 mmol), and L-MeLeu-D-Lac-OBn (3, 2.6 g, 6.8 mmol) at 0° C. The mixture is slowly warmed to room temperature and stirred for 16 h. The precipitate is removed, the filtrate is concentrated. The residue is subjected to the silica-gel chromatography by elution of 20% acetone in hexane to give the title compound as an oil (3.4 g, 52% yield). $^1$H NMR (400 MHz, CDCl3) δ 0.8–1.9 (m, 45H), 2.6–3.3 (m, 13H), 4.1–5.5 (m, 8H), 7.1–7.4 (m,15H).

Preparation of BOC-L-MeLeu-D-PhLac-L-MeLeu-D-Lac-L-MeMeu-D-PhLac-OH (38)

37 (3.4 g, 3.55 mmol) is dissolved in absolute EtOH (100 mL) and hydrogenolyzed for 17 hours at 3 atm (40 psi) over 10% palladium on charcoal (1.1 g). The reaction mixture is flushed with nitrogen, filtered, and concentrated to remove EtOH. The residue is dried under high vacuum to give 38 (2.5 g, 81%) as a semi-solid. It is used without further purification. $^1$H NMR (400 MHz, CDCl$_3$) δ 0.7–1.8 (m, 45H), 2.6–3.3 (m, 13H), 4.6–5.5 (m, 6H), 7.2–7.4 (m,10H). FAB HRMS m/z (M$^+$+H, C$_{21}$H$_{29}$N$_1$O$_6$+H) calc 392.2073 obsd 392.2086.

Preparation of BOC-L-MeLeu-D-PhLac-L-MeLeu-D-Lac-L-MeLeu-D-PhLac-L-Pip-D-Lac-OBn (39)

BOC-L-MeLeu-D-PhLac-L-MeLeu-D-Lac-L-MeLeu-D-PhLac-OH (38,417 mg, 0.48 mmol) is dissolved in methylene chloride (20 mL) and treated with DIC (0.09 ml, 0.51 mmol), DMAP (10 mg, 0.08 mmol), and L-Pip-D-Lac-OBn (23, 0.141 g, 0.48 mmol) at $_0$° C. The mixture is slowly warmed to room temperature and stirred for 16 h. The precipitate is removed, the filtrate is concentrated. The residue is subjected to the silica-gel chromatography by elution of 20% acetone in hexane to give the title compound as semi-solid (130 mg, 24% yield). FAB HRMS m/z (M$^+$+H, C$_{63}$H$_{88}$N$_4$O$_{15}$+H) calc 1141.6324 obsd 1141.6293.

Preparation of L-MeLeu-D-PhLac-L-MeLeu-D-Lac-L-MeLeu-D-PhLac-L-Pip-D-Lac-OBn (40)

BOC-L-MeLeu-D-PhLac-L-MeLeu-D-Lac-L-MeLeu-D-PhLac-L-Pip-D-Lac-OBn (39, 130 mg, 0.11 mmol) is dissolved in CH$_2$Cl$_2$ containing 10% (v/v) TFA (20 mL). The reaction mixture is stirred 1.5 h and then slowly poured into saturated K$_2$CO$_3$ aqueous solution (20 mL) with rapid stirring. The mixture is transferred to a separatory funnel and shaken. The layers are separated, and the aqueous layer extracted with CH$_2$Cl$_2$. The organic layers are combined, washed with water, dried (Na$_2$SO$_4$), filtered, and concentrated to give the title compound as an oil (0.1 g, 84% yield). It is used without further purification.

Preparation of L-MeLeu-D-PhLac-L-MeLeu-D-Lac-L-MeLeu-D-PhLac-L-Pip-D-Lac-OH (41)

L-MeLeu-D-PhLac-L-MeLeu-D-Lac-L-MeLeu-D-PhLac-L-Pip-D-Lac-OBn (40, 100 mg) is dissolved in absolute EtOH (50 mL) and hydrogenolyzed for four hours at 3 atm (40 psi) over 10% palladium on charcoal (0.1 g). The reaction mixture is flushed with nitrogen, filtered, and concentrated to remove EtOH. The residue is dried under high vacuum to give the title compound (0.08 g, 88%) as a solid. It is used without further purification.

Example 4

Preparation of cyclo(D-2-hydroxy-3-phenylpropanoyl-L-pipecolyl-D-2-hydroxypropanoyl-N-methyl-L-leucyl-D-2-hydroxy-3-phenylpropanoyl-N-methyl-L-leucyl-D-2-hydroxypropanoyl-N-methyl-L-leucyl) (42 or *731)

The amino acid (41, 80 mg, 0.084 mmol) is dissolved in methylene chloride (20 mL) and treated with triethyl amine (0.05 mL, 0.36 mmol) and 1-methyl-2-chloropyridinium iodide (30 mg, 0.12 mmol, 1.4 equiv.) at room temperature. The mixture is stirred for 16 h. The mixture is washed with 1N HCl (aqueous solution, 30 mL) and the organic layer is separated, dried (MgSO$_4$) and concentrated. The residue is purified by silica gel chromatography (30% acetone in hexane) to give the title compound (40 mg, 50%) as a solid. FAB HRMS m/z (M$^+$+Na, C$_{51}$H$_{72}$N$_4$O$_{12}$ +Na) calc 950.5044 obsd 955.5039.

Preparation of BOC-L-MeLeu-D-PhLac-L-MeLeu-D-Lac-L-MeLeu-D-PhLac-L-Tic-D-Lac-OBn (43)

BOC-L-MeLeu-D-PhLac-L-MeLeu-D-Lac-L-MeLeu-D-PhLac-OH (38, 348 mg, 0.40 mmol) is dissolved in methylene chloride (20 mL) and treated with DIC (0.077 ml, 0.44 mmol), DMAP (5 mg, 0.04 mmol), and L-Tic-D-Lac-OBn (29, 0.136 g, 0.40 mmol) at 0° C. The mixture is slowly warmed to room temperature and stirred for 16 h. The precipitate is removed, the filtrate is concentrated. The residue is subjected to the silica-gel chromatography by elution of 20% acetone in hexane to give the title compound as semi-solid (130 mg, 24% yield). FAB HRMS m/z (M$^+$+H, C$_{67}$H$_{88}$N$_4$O$_{15}$+H) calc 1211.6144 obsd 1211.6177.

Preparation of L-MeLeu-D-PhLac-L-MeLeu-D-Lac-L-MeLeu-D-PhLac-L-Tic-D-Lac-OBn (44)

BOC-L-MeLeu-D-PhLac-L-MeLeu-D-Lac-L-MeLeu-D-PhLac-L-Tic-D-Lac-OBn (39, 120 mg, 0.11 mmol) is dissolved in CH$_2$Cl$_2$ containing 10% (v/v) TFA (20 mL). The reaction mixture is stirred 1.5 h and then slowly poured into saturated K$_2$CO$_3$ aqueous solution (20 mL) with rapid stirring. The mixture is transferred to a separatory funnel and shaken. The layers are separated, and the aqueous layer extracted with CH$_2$Cl$_2$. The organic layers are combined, washed with water, dried (Na$_2$SO$_4$), filtered, and concentrated to give the title compound as an oil (0.1 g, 90% yield). It is used without further purification.

Preparation of L-MeLeu-D-PhLac-L-MeLeu-D-Lac-L-MeLeu-D-PhLac-L-Tic-D-Lac-OH (45)

L-MeLeu-D-PhLac-L-MeLeu-D-Lac-L-MeLeu-D-PhLac-L-Tic-D-Lac-OBn (40, 100 mg) is dissolved in absolute EtOH (50 mL) and hydrogenolyzed for four hours at 3 atm (40 psi) over 10% palladium on charcoal (0.1 g). The reaction mixture is flushed with nitrogen, filtered, and concentrated to remove EtOH. The residue is dried under high vacuum to give the title compound (77 mg, 85%) as a solid. It is used without further purification.

Example 5

Preparation of cyclo(D-2-hydroxypropanoyl-L-N-δ-tetrahydroquinoline-3-carboxyl-D-2-hydroxy-3-phenylpropanoyl-N-methyl-L-leucyl-D-2-hydroxypropanoyl-N-methyl-L-leucyl-D-2-hydroxy-3-phenylpropanoyl-N-methyl-L-leucyl) (46 or *798)

The amino acid (45, 77 mg, 0.084 mmol) is dissolved in methylene chloride (20 mL) and treated with triethyl amine (0.05 mL, 0.36 mmol) and 1-methyl-2-chloropyridinium iodide (30 mg, 0.12 mmol, 1.4 equiv.) at room temperature. The mixture is stirred for 16 h. The mixture is washed with 1N HCl (aqueous solution, 30 mL) and the organic layer is separated, dried (MgSO$_4$) and concentrated. The residue is purified by silica gel chromatography (30% acetone in hexane) to give the title compound (35 mg, 42%) as a solid. FAB HRMS m/z (M$^+$+Na, C$_{55}$H$_{72}$N$_4$O$_{12}$+Na) calc 1003.5044 obsd 1003.5059.

Numerous other examples of this invention may be created. Any amino acid within the generic description of the compounds of this invention can be selected. This is then the "desired amino acid." The desired amino acid should then be obtain either through purchase, from independent creation using skills available to one ordinarily skilled in the art and or as described in Chart S, see, in particular the compound shown as J-21 in Chart S-2. The following examples are provided.

Example 6

Preparation of 47 or *062

The desired amino acid is cyclized by using the general cyclization procedure. The desired final product, 47, is isolated as a solid in 50% yield. FAB HRMS m/z (M$^+$+Na, C$_{55}$H$_{79}$N$_5$O$_{13}$+Na) calc 1040.5572 obsd 1040.5550.

Example 7

Preparation of 48 or *560

The desired amino acid is cyclized by using the general cyclization procedure. The desired final product, 48, is isolated as a solid in 15% yield. $^1$H NMR (400 MHz, CDCl$_3$) δ 0.8–3.2 (m, 53H), 4.3–6.0 (m, 10H), 7.0–7.3 (m, 5H).

Example 8

Preparation of 49 or *561

The desired amino acid is cyclized by using the general cyclization procedure. The desired final product, 49, is isolated as a solid in 45% yield. FAB HRMS m/z (M$^+$+H, C$_{45}$H$_{68}$N$_4$O$_{12}$+H) calc 857.4912 obsd 857.4907

Example 9

Preparation of 50 or *625

The desired amino acid is cyclized by using the general cyclization procedure. The desired final product, 50, is isolated as a solid in 57% yield. FAB HRMS m/z (M$^+$+H, C$_{51}$H$_{72}$N$_4$O$_{12}$+H) calc 933.5225 obsd 933.5210

Example 10
Preparation of 51 or *626

The desired amino acid is cyclized by using the general cyclization procedure. The desired final product, 51, is isolated as a solid in 50% yield. FAB HRMS m/z (M$^+$+H, $C_{45}H_{68}N_4O_{12}$+H) calc 857.4912 obsd 857.4907

Example 11
Preparation of 52 or *755

The desired amino acid is cyclized by using the general cyclization procedure. The desired final product, 52, is isolated as a solid in 20% yield. FAB HRMS m/z (M$^+$+Na, $C_{51}H_{72}N_4O_{12}$+Na) calc 955.5044 obsd 955.5059

Example 12
Preparation of 53 or *776

The desired amino acid is cyclized by using the general cyclization procedure. The desired final product, 53, is isolated as a solid in 34% yield. FAB HRMS m/z (M$^+$+Na, $C_{45}H_{68}N_4O_{12}$+Na) calc 879.4731 obsd 879.4741

Example 13
Preparation of 54 or *777

The desired amino acid is cyclized by using the general cyclization procedure. The desired final product, 54, is isolated as a solid in 48% yield. FAB HRMSm/z (M$^+$+Na, $C_{51}H_{72}N_4O_{12}$+Na) calc 955.5044 obsd 955.5048

Example 14
Preparation of 55 or *819

The desired amino acid is cyclized by using the general cyclization procedure. The desired final product, 55, is isolated as a solid in 48% yield. FAB HRMS m/z (M$^+$+Na, $C_{51}H_{72}N_4O_{12}$+Na) calc 955.5044 obsd 955.5058

Example 15
Preparation of 56 or *857

The desired amino acid is cyclized by using the general cyclization procedure. The desired final product, 56, is isolated as a solid in 34% yield. FAB HRMS m/z (M$^+$+Na, $C_{50}H_{70}N_4O_{12}S$+Na) calc 973.4608 obsd 973.4626

Example 16
Preparation of 57 or *897

The desired amino acid is cyclized by using the general cyclization procedure. The desired final product, 57, is isolated as a solid in 20% yield. FAB HRMS m/z (M$^+$+Na, $C_{44}H_{66}N_4O_{12}S$+Na) calc 897.4295 obsd 892.4283

Example 17
Preparation of 58 or *421

The corresponding amino acid (135 mg) is cyclized by using the general cyclization procedure (shown in Example 5). The mixture is chromatographed on a silicagel coulmn by elution with 33% aceton in hexane. The desired final product, 58 or *421, is isolated as a solid in 34% yield (45 mg). FAB HRMS m/z (M$^+$+H, $C_{52}H_{74}N_4O_{12}$+H) calc 947.5381 obsd 947.5401.

Example 18
Preparation of 59

The desired amino acid is cyclized by using the general cyclization procedure. The desired final product, 59, is isolated and characterized by mass spectra.

Example 19
Preparation of *867

The corresponding amino acid (230 mg) is cyclized by using the general cyclization procedure. The mixture is chromatographed on a silicagel coulmn by elution with 33% aceton in hexane. The desired final product *867 is isolated as a solid in 30% yield (65 mg). FAB HRMS m/z (M$^+$+Na, $C_{49}H_{68}N_4O_{12}$+Na) calc 927.4731 obsd 927.4742.

THE REACTIONS OF GROUP 2

Unless indicated otherwise, everything in this section describes GROUP 2 reactions. The CHARTS shows a series of compounds, called Formula, and various reactions that transform the compounds. The CHARTS that show the structural description of the compounds, for all of the GROUPS follow the various textual sections. When various reaction schemes are referred to, they will also be found in the CHARTS. GROUP 2 CHARTS follow GROUP 1 CHARTS.

The ring nucleus may be comprised of eight residues (four of N-methyl-L-leucine, two of D-lactic acid, and two of 3-phenyl-D-lactic acid) in a floppy, 24-membered ring with alternating amide and ester bonds. We introduced a sigma bond between the N-methyl group of a leucine residue and the methyl group of its adjacent lactic acid to produce compounds containing one or more gamma-lactam rings. Retrosynthetic analysis of the gamma-lactam intermediate required for analog preparation suggested D-malic acid as a reasonable starting material (Scheme I—see CHART A, GROUP 2). Conversion of this to a secondary amine incorporating L-leucine and subsequent cyclization leads to the gamma-lactam itself with both chiral centers fixed.

There is at least one possible method for connection of the leucine residue to the terminal carbon atom of the malic acid, which is more remote from the hydroxyl group (Scheme II—see CHART A, GROUP 2). This requires that the carboxylic acid moiety adjacent to the hydroxyl group be protected. This is accomplished by treating L-malic acid with 2,2-dimethoxypropane and PPTS to give the dioxolanone carboxylic acid in 69–80% yield. For studies L-malic acid may be used in lieu of the much more expensive D-malic acid. Treating this with borane in THF gives the alcohol 1; the dioxolanone ring itself is not affected by this reagent. The resulting alcohol is unstable with respect to loss of acetone through intra- and intermolecular transesterification and could not be purified by silica gel chromatography. The reduction required a trade-off between complete reduction of the acid and minimization of decomposition of the product. By carefully monitoring the progress of the reaction by TLC and avoiding heating during workup the alcohol is obtained in nearly quantitative yields. Although unstable, the alcohol can be stored at 0° for several days.

Alcohol 1 is initially converted to its mesylate 2 by treating it with methanesulfonyl chloride and TEA (76%). Nucleophflic displacement of the mesylate by the amino group of L-leucine t-butyl ester hydrochloride (DMSO, TEA, KI) is largely ineffective but did result in a very poor conversion to the secondary amine 3, a highly reactive and unisolable intermediate, which spontaneously cyclized onto the dioxolanone ring with concomitant loss of acetone to give gamma-lactam in 10% yield. The major product of this reaction is crude chlorodioxolanone 4 which arose from attack on the mesylate by chloride ion and which is obtained in 45% yield. This reaction is repeated using the free base of the leucine to avoid formation of the chlorodioxolanone, but the yield of gamma-lactam is no better.

The reactions above are not preferred, more preferred are the reactions described below (Schemes III—X shown in CHARTS A to J of GROUP 2). An alternative strategy is to convert the carboxylic acid moiety to its aldehyde upon which a reductive amination can be performed. See, GROUP 2, CHART B, Scheme m. This conversion can be accomplished in two steps, first reducing dioxolanone carboxylic acid (obtained from D-malic acid) to its alcohol 5, and then oxidizing it to aldehyde 6 with PCC (65%); note the aldehyde is sometimes contaminated with a small amount of acid present in the starting material. Reductive amination of aldehyde 6 and L-leucine benzyl ester with sodium cyanoborohydride in methanol produces gamma-lactam in 55% yield, possibly by way of the elusive secondary amine, 7. The gamma-lactam serves as a D-lactyl-N-methyl-L-leucyl surrogate and is used to prepare three analogs. Synthesis of these analogs is accomplished using coupling reactions and protection groups common to peptide synthesis as elaborated below. See, GROUP 2, CHART B, Scheme m.

Tetra-γ-lactam analog *101

Preparation of the intermediate tetradepsipeptide by joining two gamma-lactam units required that in one unit the secondary alcohol be protected and the carboxyl group be deprotected. See, GROUP 2, CHART B, Scheme I. This is accomplished by silylating the hydroxyl function of with TBDMS-Cl (imidazole/DMF, 90%) to give the doubly protected gamma-lactam, 920, with subsequent hydrogenolysis (10% Pd/C, EtOH, 93%) of the benzyl protecting group to give the free acid, *922. Coupling of this with the gamma-lactam itself using DCC (DMAP, $CH_2Cl_2$) gives the tetradepsipeptide, *059, in 69% yield.

Throughout the course of this analog work we never found any NMR evidence for the formation of diastereomers caused by use of DCC in the coupling reactions. We conclude from this that diastereomers are formed in amounts of five percent or less. The small amounts of diastereomers such as they existed are removed from the final cyclodepsipeptide products by chromatography. The multiple peaks occasionally seen in the nmr spectra appear to be mostly due to the presence of rotamers.

The tetradepsipeptide, is divided into two portions. See, GROUP 2, CHART D, Scheme V. Hydrogenolysis (10% Pd/C, EtOH, 97%) of one portion gives the free acid, *930. The silyl group is removed from the remaining portion by treating it with 0.1N HCl (MeOH, 94%) to give the alcohol, *931. Coupling of the acid and alcohol with DCC (DMAP, $CH_2Cl_2$) produces the doubly-protected octadepsipeptide, *056, in 65% yield.

The silyl group is removed as described above to give the alcohol, *933, in 98% yield. See, GROUP 2, CHART F, Scheme VI. The benzyl protecting group is then removed ($H_2$, 10% Pd/C, EtOH, 94%) to give the acid-alcohol, *934. Cyclization of this compound with N-methyl-2-chloropyridinium iodide ($CH_2Cl_2$, TEA) at 5 mM concentration gives the tetra-lactam analog, *101, in 6% yield. We attribute the poor yield obtained in this cyclization to difficulty in conveniently folding the four gamma-lactam rings into a macro-size ring of 24 members (cf., di-γ-and mono-γ-lactam analogs).

Elaborated gamma-lactam

The was elaborated to a tetradepsipeptide having a particular residue sequence. This is accomplished in part by attaching a BOC protected N-methyl-L-leucine residue to the O-terminus of the gamma-lactam (DCC, DMAP, $CH_2Cl_2$, 86%) See, GROUP 2, CHART G, Scheme VII. The benzyl protecting group is removed by hydrogenolysis (10% Pd/C, EtOH, 98%) from the C-terminus and 3-phenyl-D-lactic acid benzyl ester[3] attached (DCC, DMAP, $CH_2Cl_2$, 87%). The resulting elaborated gamma-lactam, *925, is a useful intermediate.

Di-γ-lactam analog

A portion of the elaborated gamma-lactam, *925, is C-deprotected ($H_2$, 10% Pd/C, 95%) to give the acid form, *932. See, GROUP 2, CHART H, Scheme VIII. Another portion is N-deprotected (10% TFA in $CH_2Cl_2$, 97%) to give the amine form, *926. The resulting amine and acid are coupled (DCC, DMAP, $CH_2Cl_2$, 80%) to give the octadepsipeptide, *022. Removal of the BOC group (10% TFA in $CH_2Cl_2$, 95%) gives *927 from which the benzyl group is removed ($H_2$, 10% Pd/C, 89%) to give *067. Subsequent cyclization with BOP reagent and N-methylmorpholine in $CH_2Cl_2$ at high dilution (1 mM) gives the di-γ-lactam analog, *210, in 19% yield in the form of its sodium hexafluorophosphate dihydrate chelate.

Mono-γ-lactam analog

The doubly protected didepsipeptides, benzyl ester 8 and BOC amine 10, are prepared using published procedures, such as those in U.S. Pat. No. 3,520,973, incorporated by reference. See, GROUP 2, CHART I, Scheme IX.

The benzyl group is removed from LeuLac 8 and the BOC group from LeuPhLac 10 using the methods described earlier in this report to give the free acid 9 (98%) and free amine 11 (90%). These are coupled with DCC (DMAP, $CH_2Cl_2$) to give the tetradepsipeptide, *420, in 80% yield. The BOC group is removed from *420 to give the free amine, *421 (20% TFA, $CH_2Cl_2$, 92%) See, GROUP 2, CHART J, Scheme X.

The acid form of the elaborated gamma-lactam, *932, is coupled (DCC, DMAP, $CH_2Cl_2$) with *421 to give the octadepsi-peptide, *946, in 55% yield. The BOC group is removed to give *238 (20% TFA, $CH_2Cl_2$, 100%) from which the benzyl group is hydrogenolyzed (10% Pd/C, EtOH, 97%) to give the amino acid, *239. Macrolactamization is effected using BOP reagent and N-methylmorpholine in $CH_2Cl_2$ at high dilution (1 mM) to give the mono-γ-lactam analog, *919, in 27% yield. With only one gamma-lactam unit to be folded into the 24-membered ring, this cyclization gives the best yield among the three described above.

ADDITIONAL DETAILS, DESCRIPTIONS AND PROCEDURES USED TO

PREPARE THE GROUP 2 COMPOUNDS, WITH EXAMPLES

Preparation of compound 40A

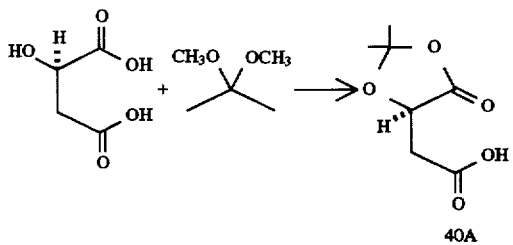

40A

D-Malic acid (13.94 g, 104 mmol) is combined with 2,2-dimethoxypropane (50 mL), PPTS (2.23 g, 8.91 mmol) added and the two-phase mixture stirred at room temperature under nitrogen. The powdery malic acid and PPTS slowly form a gum which is broken up with a spatula after five hours; the gum slowly gives way to a clear solution while stirring overnight. The reaction mixture is stirred for 53 hours and then concentrated. The residue is taken up in EtOAc and filtered through silica gel to remove the PPTS. The effluent is concentrated and the crude product recrystallized from $CH_2Cl_2$ and hexane to give 40A (13.80 g, 76%) as a white, crystalline solid. $^1H$ NMR (400 MHz, $CDCl_3$) δ 1.56 (s, 3H), 1.61 (s, 3H), 2.85 (dd, J=6.48, 17.28, 1H), 2.99 (dd, J=3.86, 17.27, 1H), 4.71 (dd, J=3.86, 6.46), 10.64 (bs, 1H). Mass spec (EI) m/z 159 [M-$CH_3$]. Anal Calcd for $C_7H_{10}O_5$: C, 48.28; H, 5.79. Found: C, 48.13; H, 5.77.

Preparation of the alcohol 5 of GROUP 2, CHART B, Scheme III (13.6 g, 78.1 mmol) is dissolved in THF (40 mL) and cooled to 0° under an atmosphere of nitrogen. A solution of Borane/THF (100 mL, 1.0M, 100 mmol) is added dropwise over a period of 47 minutes. The reaction mixture is stirred 60 minutes at 0° and then for 120 minutes at 24°. The mixture is cooled to 0°, methanol (50 mL) added dropwise and the mixture stirred five minutes to destroy the remaining borane. The mixture is concentrated at or below 35°, MeOH (100 mL) added and the resulting solution concentrated. A final concentration from EtOAc (100 mL) gives alcohol 5 (12.5 g, ~100%) as a clear, colorless oil. It is stored under nitrogen at 0° for several days without deterioration. $^1H$ NMR (400 MHz, $CDCl_3$) δ1.55 (s, 3H), 1.61 (s, 3H), 1.97 (m, 1H), 2.14 (m, 1H), 3.82 (m, 2H), 4.56 (dd, J=4.92, 7.08, 1H). Good yields.

Preparation of the methanesulfonate 2 of GROUP 2, CHART A, Scheme II

Alcohol 1 (1.31 g, 8.18 mmol) is dissolved in $CH_2Cl_2$ (15 mL) and TEA (2.3 mL, 16.4 mmol) added. The reaction mixture is cooled to 0° and a solution of methanesulfonyl chloride (1.22 g, 10.6 mmol) in $CH_2Cl_2$ (5 mL) added in a rapid dropwise fashion. The cooling bath is removed and the reaction mixture heated under reflux for 30 minutes. It is then concentrated and the residue taken up in water and twice extracted with ether. The extracts areε combined and washed in turn with 2N HCl, saturated $NaHCO_3$, and NaCl. Drying over anhydrous $Na_2SO_4$, filtration and concentration gave mesylate 2 (1.28 g, 66%) as a clear, orange-colored oil. $^1H$ NMR (400 MHz, $CDCl_3$) δ 1.56 (s, 3H), 1.63 (s, 3H), 2.18 (m, 1H), 2.32 (m, 1H), 3.03 (s, 3H), 4.37 (m, 1H), 4.42 (m, 1H), 4.51 (m, 1H).

Preparation of compound *242 of GROUP 2, CHART A, Scheme II

Mesylate 2 (500 mg, 2.10 mmol) is dissolved in DMSO (2.0 mL). TEA (0.32 mL, 2.31 mmol) and potassium iodide (5 mg, 0.03 mmol) are added followed by the addition of L-leucine, tert-butyl ester hydrochloride (470 mg, 2.10 mmol). The reaction mixture is heated at 60°-63° for 17 hours during which time all solids dissolved; a small amount of gum is observed adhering to the stir bar. The reaction mixture is diluted with ether (65 mL) and washed with water (2×35 mL) followed by a wash with saturated NaCl (35 mL). The organic phase is dried ($Na_2SO_4$), filtered and concentrated to a clear, orange-brown oil. This is chromatographed on a 2 mm plate of silica gel contained in a Chromatotron. The plate is eluted with 30% EtOAc in hexane. From an early eluting fractions there is obtained gamma-lactam *242 (57.6 mg, 10%) as a white, crystalline solid. $^1H$ NMR (400 MHz, $CDCl_3$) δ 0.88 (s, 1.5H), 0.897 (s, 1.5H), 0.904 (s, 1.5H), 0.92 (s, 1.5H), 1.44 (s, 10H), 1.62 (m, 2H), 1.99 (m, 1H), 2.41 (m, 1H), 3.18 (m, 1H), 4.34 (m, 1H), 4.64 (m, 1H). Mass spec (EI) m/z 271 [M]. Further elution gives the chlorodioxolanone 4 (170 mg, 45%) as a clear, dark-yellow oil containing some impurities. $^1H$ NMR (400 MHz, $CDCl_3$) δ 1.55 (s, 3H), 1.61 (s, 3H), 2.16 (m, 1H), 2.33 (m, 1H), 3.69 (m, 2H), 4.58 (m,1H). Mass spec (EI) m/z 163, 165 [M-$CH_3$].

Preparation of aldehyde 6 of GROUP 2, CHART B, Scheme III

Alcohol 5 (17.8 g, 111 mmol) is dissolved in $CH_2Cl_2$ (700 mL) and cooled to 0°. Solid pyridinium chlorochromate (120 g, 555 mmol) is added all at once and the cooling bath removed. The reaction mixture is stirred at room temperature for four hours and then poured into ether (1000 mL). The residual solid in the reaction flask is triturated several times with ether bringing the total volume of ether to 2000 mL. The combined ether solutions are filtered through Celite giving a clear, dark orange-colored filtrate. This is treated with activated carbon (Darco G-60) and stirred intermittently for 20 minutes after which it is filtered through Celite giving a clear, pale-yellow filtrate. This is concentrated at less than 42°. The residue is dissolved in EtOAc and again concentrated followed by drying under high vacuum to give aldehyde 6 (12.90 g, 73%) as a clear, brown-green oil. NMR spectroscopy shows the product to contain 90 mole % aldehyde and 10 mole % acid (present in the starting material) giving an adjusted yield of 65%. This material is stored under nitrogen at 0°. $^1H$ NMR (400 MHz, $CDCl_3$) δ 1.57 (s, 3H), 1.62 (s, 3H), 2.91 (dd, J=7.20, 18.37, 1H), 3.09 (dd, J=3.52, 18.33, 1H), 4.78 (dd, J=3.54, 6.98, 1H), 9.74 (s, 1H). About 50% yield.

Alternate preparation of compound *242

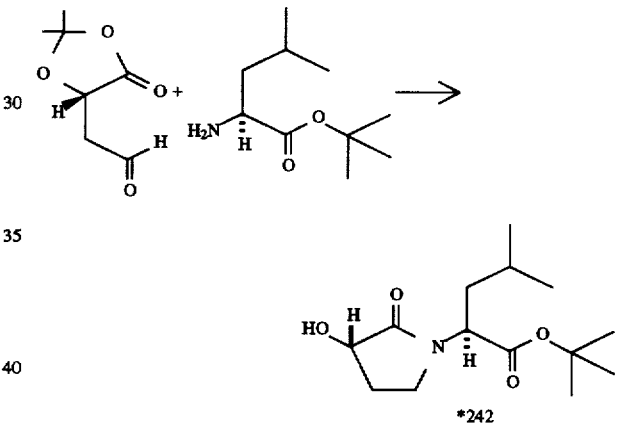

*242

L-Leucine tert-butyl ester (390 mg, 2.08 mmol) is dissolved in MeOH (5.0 mL) and the solution cooled in an ice-water bath under a nitrogen atmosphere. The enantiomer of aldehyde 6 (303 mg, 1.92 mmol) is added followed by glacial acetic acid (0.25 mL). The reaction mixture is stirred at 0° for 26 minutes and then treated with powdered NaC-$NBH_3$ (59 mg, 0.945 mmol). The reaction mixture is stirred at 25° for three hours and then poured into saturated $NaHCO_3$. When $CO_2$ evolution has ceased, the mixture is transferred to a separatory funnel and extracted with ether (2×). The organic phases are combined, dried ($Na_2SO_4$), filtered and concentrated. The residue is dissolved in EtOAc and concentrated to give a clear, light-yellow oil (569 mg) which mostly crystallizes on standing. An analytical sample is obtained by triturating this material with 30% EtOAc/ hexane which gives on filtration white needles (87 mg), mp 123.3°-124.5°. The filtrate is concentrated and the residue purified by silica gel chromatography (2 mm plate in a Chromatotron) using 30% EtOAc in hexane as the eluant. From the appropriate fractions there are obtained *242 (245 mg, 47%) as a white, crystalline solid for a total yield of 332 mg (64%). $^1H$ NMR (400 MHz, $CDCl_3$) δ 0.88-0.98 (3d, 6H), 1.41 (m, 1H), 1.44 (s, 9H), 1.65 (m, 2H), 2.01 (m, 1H), 2.43 (m, 1H), 3.20 (m, 1H), 3.54 (m, 1H), 4.36 (m, 1H), 4.67

(m, 1H). Anal Calcd for $C_{14}H_{25}NO_4$:C, 61.97; H, 9.29; N, 5.15. Found: C, 61.78; H, 9.14; N, 5.01.

L-Leucine benzyl ester (8.86 g, 40.0 mmol), MeOH (100 mL), aldehyde 6 (8.33 g, 40.0 mmol), glacial acetic acid (5.5 mL) and NaCNBH$_3$ (1.26 g, 20.0 mmol) are combined following the procedure used in the preparation of *242. The reaction mixture is processed and the resulting crude material purified by chromatography to give *058 (6.68 g, 55%) as a yellow oil. $^1$H NMR (400 MHz, CDCl$_3$) δ 0.92 (d, J=6.75, 3H), 0.94 (d, J=6.88, 3H), 1.47 (m, J=6.81, 1H), 1.73 (dd, J=7.37, 7.82, 2H), 1.92 (m, 1H), 2.42 (m, 1H), 3.33 (m, 2H), 4.15 (bs, 1H), 4.37 (dd, J=8.37, 8.72, 1H), 4.91 (dd, J=7.72, 8.39, 1H), 5.11 (d, J=12.31, 1H), 5.15 (d, J=12.30, 1H), 7.34 (m, 5H). Mass spec (EI). Calcd m/z for $C_{17}H_{23}NO_4$:305.1627. Found: 305.1615.

Preparation of compound *920, GROUP 2, CHART C, Scheme IV

Imidazole (0.36 g, 5.24 mmol) is added to a solution of *058 (1.60 g, 5.24 mmol) in DMF (5.0 mL) under an atmosphere of nitrogen and the mixture stirred until a complete solution is achieved. The solution is cooled to 0° and solid TBDMS-Cl (0.79 g, 5.24 mmol) added all at once. The reaction mixture is stirred five minutes at 0° and then at 25° for three hours. The reaction mixture is poured into water and extracted with hexane three times. The extracts are combined, dried (Na$_2$SO$_4$) and filtered. The filtrate is filtered through silica gel (11 g) which is washed with 5% EtOAc in hexane. The filtrate is concentrated to give *920 (1.98 g, 90%) as a clear, colorless oil which solidified on standing. $^1$H NMR (400 MHz, CDCl$_3$) δ 0.14 (s, 3H), 0.15 (s, 3H), 0.92 (s, 9H), 0.94 (d, J=6.19, 6H), 1.50 (m, J=5.02, 1H), 1.71 (m,2H), 1.87 (m, 1H), 1.87 (m, 2H), 2.26 (m, 1H), 3.30 (m, 2H), 4.28 (t, J=7.39, 1H), 4.90 (m, 1H), 5.12 (m, 2H), 7.34 (m, 5H). $^{13}$C NMR (400 MHz, CDCl$_3$) δ 18.7, 21.6, 23.5, 25.1, 26.1, 29.9, 37.3, 40.1, 52.5, 67.2, 71.6, 128.5, 128.7, 129.0, 135.9, 171.7, 174.6. Anal Calcd for $C_{23}H_{37}NO_4$Si:C, 65.83; H, 8.89; N, 3.24. Found: C, 65.81; H, 8.83; N, 3.28.

Preparation of compound *922, GROUP 2, CHART C, Scheme IV

*920 (1.95 g, 4.65 mmol), 10% Pd on carbon (380 mg) and absolute EtOH (100 mL) are combined according to the general hydrogenolysis procedure described earlier to give *922 (1.51 g, 99%) as a clear, colorless oil which solidifies on standing. Proton NMR spectroscopy shows this material to consist of 94 wt % product and 6 wt % EtOAc for an adjusted yield of 93%. $^1$H NMR (400 MHz, CDCl$_3$) δ 0.14 (s, 6H), 0.90 (s, 9H), 0.91–0.98 (2d, J=7.06, 6H), 1.26 (m, 1H), 1.74 (m, 2H), 1.88 (m, 1H), 2.31 (m, 1H), 3.35 (m, 2H), 4.35 (t, J=7.32, 1H), 4.82 (dd, J=5.94, 9.98, 1H). Mass spec (EI) m/z 314 [M-CH$_3$].

Preparation of compound *059, GROUP 2, CHART C, Scheme IV

*922 (1.47 g, 4.46 mmol), and *058 (1.36 g, 4.46 mmol), a solution of DCC (4.5 mL, 1.0M, 4.5 mmol) in CH$_2$Cl$_2$, DMAP (27 mg, 0.22 mmol) and CH$_2$Cl$_2$ (25 mL) are combined according to the DCC general coupling procedure described earlier. Chroma-tography (20% EtOAc in hexane) performed on the crude reaction products gives *059 (1.91 g, 69%) as a white solid. $^1$H NMR (400 MHz, CDCl$_3$) δ 0.13 (s, 3H), 0.14 (s, 3H), 0.90 (s, 9H), 0.91–0.99 (~3d, 12H), 1.50 (m, 2H), 1.73 (m, 4H), 1.90 (m, 2H), 2.29 (m, 1H), 2.48 (m, 1H), 3.53 (m, 4H), 4.27 (t, J=7.24, 1H), 4.91 (m, 2H), 5.10 (d, J=12.2, 1H), 5.15 (d, J=12.2, 1H), 5.33 (t, J=8.30, 1H), 7.34 (m, 5H). Mass spec (FAB) m/z 617 [M+H]. Anal Calcd for $C_{33}H_{52}N_2O_7$Si:C, 64.25; H, 8.50; N, 4.54. Found: C, 64.05; H, 8.42; N, 4.50.

Preparation of compound *930, GROUP 2, CHART D, Scheme V

*059 (941 mg, 1.53 mmol), 10% Pd on carbon (128 mg) and absolute EtOH (100 mL) are combined according to the general hydrogenolysis procedure described earlier to give *930 (800 mg, 97%) as a white solid. $^1$H NMR (400 MHz, CDCl$_3$) δ 0.13 (s, 3H), 0.14 (s, 3H), 0.90 (s, 9H), 0.91–1.00 (~3d, 12H), 1.51 (m, 2H), 1.75 (m, 4H), 1.96 (m, 2H), 2.29 (m, 1H), 2.52 (m, 1H), 3.34 (m, 3H), 3.48 (m, 1H), 4.29 (t, J=7.12, 1H), 4.82 (dd, J=6.12, 9.76, 1H), 4.93 (dd, J=6.28, 9.72, 1H), 5.37 (t, J=8.26, 1H), 7.27 (bs, 1H). Mass spec (FAB) m/z 527 [M+H] and 549 [M+Na].

Preparation of compound *931, GROUP 2, CHART D, Scheme V

*059 (918 mg, 1.49 mmol) is dissolved in THF (3 mL) and methanolic HCl (17 mL, 0.1N) added. The reaction mixture is stirred at room temperature for 2.5 hours and then treated with saturated NaHCO$_3$ (0.5 mL). The mixture is concentrated at 50° to about 1 mL and the residue taken up in EtOAc and washed with water. The aqueous layer is extracted with EtOAc. The organic phases are combined, dried (MgSO$_4$), filtered and concentrated. Final drying under high vacuum gives *931 (745 mg, 94%) as a clear oil. $^1$H NMR (400 MHz, CDCl$_3$) δ 0.89–1.00 (~3d, 12H), 1.49 (m, 2H), 1.74 (m, 4H), 1.91 (m, 2H), 2.47 (m, 2H), 3.33 (m, 2H), 3.42 (m, 2H), 4.32 (t, J=8.42, 1H), 4.90 (m, 2H), 5.10 (d, J=12.2, 1H), 5.14 (d, J=12.2, 1H), 5.33 (t, J=8.28, 1H), 7.34 (m, 5H). Mass spec (EI) m/z 502 [M].

Preparation of compound *956, GROUP 2, CHART D, Scheme V

*930 (738 mg, 1.40 mmol), *931 (704 mg, 1.40 mmol), a solution of DCC (1.4 mL, 1.0M, 1.40 mmol) in CH$_2$Cl$_2$, DMAP (8.6 mg, 0.070 mmol) and CH$_2$Cl$_2$ (20 mL) are combined according to the DCC general coupling procedure described earlier. Chromatography (20% and 35% EtOAc in hexane) performed on the crude reaction products gives 056 (912 mg, 65%) as a white solid. $^1$H NMR (400 MHz, CDCl$_3$) δ 0.14 (s, 3H), 0.15 (s, 3H), 0.90 (s, 9H), 0.92–1.00 (~3d, 24H), 1.50 (m, 4H), 1.75 (m, 8H), 1.93 (m, 4H), 2.28 (m, 1H), 2.49 (m, 3H), 3.35 (m, 6H), 3.49 (m, 2H), 4.27 (t, J=7.18, 1H), 4.90 (m, 4H), 5.10 (dd, J=~13, 1H), 5.15 (dd, J=~13, 1H), 5.33 (m, 3H), 7.33 (m, 5H). Mass spec (FAB) m/z 1011[M+H]. Anal Calcd for $C_{53}H_{82}N_4O_{13}$Si: C, 62.95; H, 8.17; N, 5.54. Found: C, 62.95 (sic); H, 7.99; N, 5.51.

Preparation of compound *933, GROUP 2, CHART F, Scheme VI

*056 (846 mg, 0.837 mmol) is dissolved in THF (2 mL) and treated with methanolic HCl (10 mL, 0.1N) for 2.5 hours at room temperature. The reaction mixture is processed as described earlier (see preparation of *931) to give *933 (738 mg, 98%) as a white, powdery solid. $^1$H NMR (400 MHz, CDCl$_3$) δ 0.90–1.03 (~3d, 24H), 1.49 (m, 4H), 1.78 (m, 8H), 1.95 (m, 4H), 2.49 (m, 4H), 3.13 (m, 6H), 3.44 (m, 1H), 3.50 (m, 1H), 4.30 (m, 1H), 4.90 (m, 4H), 5.12 (m, 2H), 5.33 (m, 3H), 7.34 (m, 5H). Mass spec (FAB) m/z 897 [M+H] and 919 [M+Na].

Preparation of compound *934, GROUP 2, CHART F, Scheme VI

*933 (738 mg, 0.823 mmol) is dissolved in THF (75 mL). The resulting solution is combined with absolute EtOH (75 mL) and 10% Pd on carbon (92 mg). With the exception that THF is used in place of EtOH to wash the product from the Celite the general hydrogenolysis procedure described earlier is followed to give *934 (687 mg, 94%) as an off-white solid. $^1$H NMR (400 MHz, CDCl$_3$) δ 0.89–1.00 (~3d, 24H), 1.48 (m, 4H), 1.76 (m, 8H), 1.93 (m, 4H), 2.51 (m, 4H), 3.34 (m, 4H), 3.50 (m, 4H), 4.36 (t, J=8.34, 1H), 4.79 (m, 1H), 4.89 (m, 3H), 5.33 (m, 2H), 5.39 (m, 1H). Mass spec (FAB) m/z 807 [M+H] and 829 [M+Na].

Preparation of compound *101, GROUP 2, CHART F, Scheme VI

*934 (619 mg, 0.768 mmol) is dissolved in $CH_2Cl_2$ (190 mL) to give a 5 mM solution. TEA (0.53 mL, 3.79 mmol) is added followed by N-methyl-2-chloropyridinium iodide (266 mg, 1.04 mmol) and the reaction mixture stirred at room temperature for four days. The reaction mixture is concentrated and the residue dissolved in chloroform. The resulting solution is filtered through silica gel (40 g) by washing with chloroform (350 mL). Concentration of the filtrate followed by drying under high vacuum gives crude product (147 mg) as a tan-colored solid. Additional washing using EtOAc (300 mL) gives more crude product (52 mg) as a white solid. The two batches of crude product are combined and further purified by dissolving them in a minimum amount of $CH_2Cl_2$ and injecting them into a Chromatotron (2 mm silica gel plate) and eluting with 30% to 100% EtOAc in hexane. From the appropriate fractions there is obtained *101 (36 mg, 6%) as a white powder which nmr shows to be quite pure. $^1$H NMR (400 MHz, $CDCl_3$) δ 0.91 (bs, 24H), 1.4–2.1 (bm, 14H), 2.33 (bm, 2H), 2.56 (bm, 4H), 3.1–3.6 (bm, 8H), 3.92 (bm, 2H), 4.94 (bm, 2H), 5.31 (bm, 2H), 6.07 (bm, 2H). $^{13}$C NMR (100 MHz, $CDCl_3$) δ 21.4, 23.6, 26.6, 170.0 171.9. High resolution mass spec (FAB). Calcd m/z for $C_{40}H_{60}N_4O_{12}+H_1$:789.4286. Found: 789.4262.

Preparation of compound *923, GROUP 2, CHART G, Scheme VII

N-BOC-N-Methyl-L-leucine (2.42 g, 9.86 mmol), *058 (3.01 g, 9.86 mmol), a solution of DCC (9.9 mL, 1.0M, 9.9 mmol) in $CH_2Cl_2$, DMAP (60 mg, 0.49 mmol) and $CH_2Cl_2$ (50 mL) are combined according to the general DCC coupling procedure described earlier to give crude product which upon chromatography affords *923 (4.50 g, 86%) as a clear, colorless, viscous oil. Mass spec (FAB) m/z 533 [M+H]

Preparation of compound *875, GROUP 2, CHART G, Scheme VII

*923 (4.46 g, 8.37 mmol), 10% Pd on carbon (700 mg) and absolute EtOH (100 mL) are combined according to the general hydrogenolysis procedure described earlier to give *875 (3.63 g, 98%) as a white solid. $^1$H NMR (400 MHz, $CDCl_3$) δ 0.89–1.00 (~3d, 12H), 1.43 (s, 9H), 1.52 (m, 2H), 1.75 (m, 4H), 1.96 (m, 1H), 2.53 (m, 1H), 2.76 (s, 1.5H), 2.78 (s, 1.5H), 3.37 (m 1H), 3.50 (m, 1H), 4.70 (m, 0.5H), 4.86 (m, 1.5H), 5.38 (dd, J=8.10, 17.5, 1H), 8.03 (bs, 1H). Mass spec (FAB) m/z 443 [M+H] and 465 [M+Na]. Anal Calcd for $C_{22}H_{38}N_2O_7$:C, 59.71; H, 8.66; N, 6.33. Found: C, 59.72; H, 8.68; N, 6.34.

Preparation of compound *925, GROUP 2, CHART G, Scheme VII

*875 (3.50 g, 7.91 mmol), 3-phenyl-D-lactic acid benzyl ester[3] (2.03 g, 7.91 mmol), a solution of DCC (7.9 mL, 1.0M, 7.9 mmol) in $CH_2Cl_2$, DMAP (48 mg, 0.40 mmol) and $CH_2Cl_2$ (75 mL) are combined according to the DCC general coupling procedure described earlier to give crude product which upon chromatography produces *925 (4.93 g, 87%) as a clear, pale-yellow oil. $^1$H NMR (400 MHz, $CDCl_3$) δ 1.87–1.99 (~3d, 12H), 1.40 (m, 1H), 1.46 (s, 9H), 1.59 (m, 3H), 1.73 (m, 3H), 2.18 (m, 1H), 2.77 (s, 1.5H), 2.80 (s, 1.5H), 3.10 (m, 2H), 3.15 (m, 2H), 4.73 (m 0.5H), 4.92 (m, 1.5H), 5.09 (d, J=12.1, 1H), 5.15 (d, J=12.0, 1H), 5.22 (m, 1H), 5.31 (m, 1H), 7.05–7.40 (m, 10H). Mass spec (FAB) m/z 681 [M+H].

Preparation of compound *932, GROUP 2, CHART H, Scheme VIII

*925 (2.48 g, 3.64 mmol), 10% Pd on carbon (300 mg) and absolute EtOH (100 mL) are combined according to the general hydrogenolysis procedure described earlier to give *932 (2.05 g, 95%) as a glass. $^1$H NMR (400 MHz, $CDCl_3$) δ 0.85–1.00 (~4d, 12H), 1.35–1.49 (m, 1H), 1.46 (s, 9H), 1.60 (m, 3H), 1.72 (m, 2H), 187 (m, 1H), 2.32 (m, 1H), 2.78 (s, 1.5H), 2.80 (s, 1.5H), 3.14 (m, 1H), 3.19–3.38 (m, 3H), 4.78–4.98 (m, 2H), 5.30 (m, 2H), 7.16–7.37 (m, 6H). Mass spec (EI) m/z 590 [M].

Preparation of compound *926, GROUP 2, CHART H, Scheme VIII

*925 (2.40 g, 3.53 mmol), $CH_2Cl_2$ (90 mL) and TFA (10 mL) are combined according to the general procedure for removing a BOC protecting group described earlier to give *926 (1.98 g, 97%) as a nearly colorless oil. $^1$H NMR (400 MHz, $CDCl_3$) δ 0.87–0.98 (~3d, 12H), 1.42 (m, 1H), 1.50 (m, 2H), 1.58 (m, 1H), 1.64 (m, 2H), 1.77 (m, 2H), 2.22 (m, 1H), 2.42 (s, 3H), 3.03–3.21 (m, 4H), 3.30 (t, J=7.27, 1H), 4.93 (dd, J=5.11, 10.9, 1H), 5.10 (d, J=12.1, 1H), 5.15 (d, J=12.1, 1H), 5.22–5.36 (m, 2H), 7.10 (m, 2H), 7.29 (m, 5H), 7.38 (m, 3H). Mass spec (EI) m/z 580 [M]. Anal Calcd for $C_{33}H_{44}N_2O_7$:C, 68.25; H, 7.64; N, 4.82. Found: C, 67.86; H, 7.56; N, 4.76.

Preparation of compound *022, GROUP 2, CHART H, Scheme VIII

*932 (1.95 g, 3.31 mmol), and *926 (1.92 g, 3.31 mmol), a solution of DCC (3.3 mL, 1.0M, 3.3 mmol) in $CH_2Cl_2$, DMAP (20 mg, 0.17 mmol) and $CH_2Cl_2$ (50 mL) are combined according to the DCC general coupling procedure described earlier. Chromatography of the crude reaction product gives *022 (3.04 g, 80%) as a white, solid foam. $^1$H NMR (400 MHz, $CDCl_3$) 8 0.80–1.00 (~5d, 24H), 1.46 (s, 9H), 1.40–1.99 (m, 14H), 2.12 (m, 1H), 2.45 (m, 1H), 2.77 (bs, 1.5H), 2.80 (bs, 1.5H), 2.88 (s, 2.5H), 2.93 (s, 0.5H), 3.00–3.20 (m, 6H), 3.24 (m, 1H), 3.48 (m, 1H), 4.60–4.76 (m, 1H), 4.89 (m, 2H), 5.09 (d, J=12.1, 1H), 5.15 (d, J=12.1, 1H), 5.19 (m, 1H), 5.30 (m, 3H), 5.38 (m, 1H), 7.09 (m, 2H), 7.19 (m, 2H), 7.28 (m, 8H), 7.33 (m, 3H). Mass spec (FAB) m/z 1153 [M+H] and 1175 [M+Na]. Anal Calcd for $C_{64}H_{88}N_4O_{15}$:C, 66.65; H, 7.69; N, 4.86. Found: C, 66.37; H, 7.73; N, 4.96.

Preparation of compound *927A, GROUP 2, CHART H, p.2, Scheme VIII

*022 (2.95 g, 2.56 mmol), $CH_2Cl_2$ (90 mL) and TFA (10 mL) are combined according to the general procedure for removing a BOC protecting group described earlier to give *927 (2.61 g, 95%) as a white, solid foam and glass. $^1$H NMR (400 MHz, $CDCl_3$) δ 0.80–1.03 (~4d, 24H), 1.03–1.98 (m, 16H), 2.12 (m, 1H), 2.41 (s, 3H), 2.50 (m, 1H), 2.89 (s, 2.5H), 2.93 (s, 0.5H), 3.00–3.21 (m, 6H), 3.30 (m, 2H), 3.50 (m, 1H), 4.89 (m, 2H), 5.09 (d, J=12.1, 1H), 5.15 (d, J=12.1, 1H), 5.20 (m, 1H), 5.25–5.46 (m, 4H), 7.10 (m, 2H), 7.0 (m, 2H), 7.28 (m, 8H), 7.35 (m, 3H). Mass spec (FAB m/z 1053 [M+H].

Preparation of compound *067, GROUP 2, CHART H, p.2, Scheme VIII

*927 (2.70 g, 2.56 mmol), 10% Pd on carbon (290 mg) and absolute EtOH (100 mL) are combined according to the general hydrogenolysis procedure described earlier to give *067 (2.20 g, 89%) as a cream-colored solid. $^1$H NMR (400 MHz, $CDCl_3$) δ 0.80–1.00 (~4d, 24H), 1.02–2.00 (m, 15H), 2.48 (s, 3H), 2.49 (m, 1H), 2.85 (s, 3H), 3.00–3.50 (m, 8H), 3.56 (m, 1H), 4.79 (m, 1H), 4.88 (m, 1H), 5.09 (m, 1H), 5.20 (m, 1H), 5.34 (m, 1H), 5.47 (m, 2H), 7.10–7.40 (m, 11H). $^{13}$C NMR (100 MHz, $CDCl_3$) δ 8 14.6, 21.6, 21.6, 21.7, 22.4, 23.0, 23.4, 23.5, 23.6, 24.9, 25.1, 25.1, 25.2, 25.7, 26.0, 31.9, 33.2, 34.2, 36.3, 36.8, 37.5, 37.8, 40.6, 52.5, 56.1, 60.6, 60.7, 72.2, 72.4, 127.1, 127.6, 128.612, 129.0, 129.8, 130.0, 135.6, 170.1, 170.2, 170.6, 170.7, 170.8, 173.9. Mass spec (FAB) m/z 963 [M+H].

Preparation of compound *210, GROUP 2, CHART H, p.2, Scheme VIII

*067 (2.18 g, 2.26 mmol) is dissolved in $CH_2Cl_2$ (2260 mL) to give a concentration of 1 mM and the solution cooled to 0°. BOP reagent (1.05 g, 2.38 mmol) is added and stirred until completely dissolved. NMM (0.26 mL, 2.38 mmol) is added and the reaction mixture stirred at 0° for 30 minutes and then for 3 days at room temperature. The reaction mixture is concentrated to about 100 mL and washed with saturated $NH_4Cl$ (250 mL). The layers are separated and the organic layer dried ($MgSO_4$), filtered through Celite and concentrated. The residue is dissolved in EtOAc and again concentrated. Drying under high vacuum gives a light yellow solid foam. This is further purified by chromatography to give *210 (501 mg, 19%) as a white, solid foam. $^1H$ NMR (400 MHz, $CDCl_3$) δ 0.77–1.02 (~3d, 24H), 1.14 (m, 2H), 1.46 (m, 2H), 1.50–1.80 (m, 8H), 2.08 (m, 2H), 2.59 (m, 2H), 2.69 (bs, 2H), 2.87 (s, 6H), 3.15 (m, 4H), 3.48 (m, 4H), 4.49 (m, 2H), 4.94 (m, 2H), 5.47 (t, J=9.11, 2H), 5.54 (t, J=7.38, 2H), 7.27 (m, 10H). $^{13}C$ NMR (100 MHz, $CDCl_3$) δ 21.8, 23.2, 23.3, 25.2, 25.3, 25.9, 31.2, 36.5, 37.0, 37.9, 54.6, 55.6, 72.1, 72.3, 127.7, 129.0, 129.8, 135.2, 170.5, 171.4, 172.2, 172.5. $[α]_D$=–80° (c 1.0, $CH_3OH$). Mass spec (FAB). Calcd m/z for $C_{52}H_{72}N_4O_{12}+Na_1$:976.5044. Found: 976.5053. Anal Calcd for $C_{52}H_{72}N_4O_{12}+2H_2O+NaPF_6$:C, 54.35; H, 6.67; N, 4.88; P, 2.70; F, 9.92. Found: C, 54.51; H, 6.64; N, 4.89; P, 2.81; F, 8.63.

Preparation of compound 9, GROUP 2, CHART I, Scheme IX

Benzyl ester $8^{3,4}$ (7.62 g, 18.7 mmol), 10% Pd on carbon (1.50 g) and absolute EtOH (150 mL) are combined according to the general hydrogenolysis procedure described earlier to give free acid 9 (5.82 g, 98%) as a slightly turbid, pale-yellow oil. $^1H$ NMR (400 MHz, $CDCl_3$) δ 0.89–1.00 (2d, 6H), 1.45 (s, 4.5H), 1.46 (s, 4.5H), 1.50–1.80 (m, 6H), 2.81 (s, 3H), 4.74 (m, 0.5H), 4.84 (m, 0.5H), 5.12 (m, 1H), 8.91 (bs, 1H).

Preparation of compound 11, GROUP 2, CHART I, Scheme IX

BOC Amine 10, See, F. E. Dutton and S. J. Nelson, *J. Antibiotics* (1994) Vol. 47 (11), 1322–1327, incorporated by reference, (8.57 g, 17.7 mmol), $CH_2Cl_2$ (50 mL) and TFA (6 mL) are combined according to the general procedure for removing a BOC protecting group described earlier to give free amine 11 (6.09 g, 90%) as a clear, pale-yellow oil. $^1H$ NMR (400 MHz, $CDCl_3$) δ 0.75–0.82 (2d, 6H), 1.29 (t, J=7.22, 2H), 1.42 (bs, 1H), 1.49 (m, 1H), 2.20 (s, 3H), 3.08 (dd, J=9.84, 14.2, 1H), 3.18 (t, J=7.18, 1H), 3.28 (dd, J=4.02, 14.3, 1H), 5.15 (d, J=12.2, 1H), 5.20 (d, J=12.2, 1H), 5.32 (dd, J=4.02, 9.88, 1H), 7.17–7.40 (m, 10H). Mass spec (FAB). Calcd m/z for $C_{23}H_{29}NO_4+H_1$:384.2175. Found: 384.2183.

Preparation of compound 420, GROUP 2, CHART I, Scheme IX

Free acid 9 (5.02 g, 15.8 mmol), free amine 11, (6.06 g, 15.8 mmol), a solution of DCC (16 mL, 1.0M, 16 mmol) in $CH_2Cl_2$, DMAP (97 mg, 0.8 mmol) and $CH_2Cl_2$ (150 mL) are combined according to the DCC general coupling procedure described earlier. Chromatography of the crude reaction product gives *420 (8.68 g, 80%) as a clear, nearly colorless oil. $^1H$ NMR (400 MHz, $CDCl_3$) δ 0.80–1.00 (~4d, 12H), 1.30–1.90 (m, 9H), 1.43 (s, 4.5H), 1.46 (s, 4.5 H), 2.75 (s, 0.5H), 2.84 (3s, 5H), 2.92 (s, 0.5H), 3.18 (bs, 2H), 4.68–5.42 (m, 4H), 5.09 (d, J=12.1, 1H), 5.16 (d, J=11.9, 1H), 7.10–7.40 (m, 10H). Mass spec (FAB). Calcd m/z for $C_{38}H_{54}N_2O_9+H_1$:683.3907. Found: 683.3911.

Preparation of compound 421, GROUP 2, CHART J, Scheme X

*420 (1.58 g, 2.31 mmol), $CH_2Cl_2$ (108 mL) and TFA (27 mL) are combined according to the general procedure for removing a BOC protecting group described earlier to give *421 (1.24 g, 92%) as a clear, pale-yellow oil. $^1H$ NMR (400 MHz, $CDCl_3$) δ 0.80–0.98 (~5d, 12H), 1.28–1.90 (m, 7H), 1.46 (d, J=6.85, 3H), 2.38 (s, 3H), 2.77 (s, 0.5H), 2.80 (s, 2H), 2.84 (s, 0.5H), 3.16 (m, 2H), 3.30 (t, J=7.25, 1H), 5.08 (d, J=12.1, 1H), 5.14(d, J=13.0, 1H), 5.25 (dd, J=5.20, 7.24, 1H), 5.34 (dd, J=5.01, 10.9, 1H), 5.48 (dd, J=6.80, 13.5, 1H), 7.10–7.41 (m, 10H). Mass spec (FAB). Calcd m/z for $C_{33}H_{46}N_2O_7+H_1$:583.3383. Found: 583.3375.

Preparation of compound 946, GROUP 2, CHART J, Scheme X

*932 (1.27 g, 2.15 mmol), and *421 (1.29 g, 2.21 mmol), DCC (2.6 mL, 1.0M, 2.6 mmol), DMAP (16 mg, 0.13 mmol) and $CH_2Cl_2$ (75 mL) are combined according to the DCC general coupling procedure described earlier. Chromatography of the crude reaction product gives *946 (1.48 g) as a clear, colorless oil. Proton nmr shows 92 wt % product and 8 wt % EtOAc for a yield of 55%. $^1H$ NMR (400 MHz, $CDCl_3$) δ 0.79–1.00 (~6d, 24H), 1.43 (s, 9h), 1.38–1.50 (m, 4H), 1.50–1.99 (m, 13H), 2.70–3.30 (15H), 4.60–5.50 (m, 10H), 7.08–7.40 (m, 15H). Mass spec (FAB). Calcd m/z for $C_{64}H_{90}N_4O_{15}+Na_1$:1177.6300. Found: 1177.6275.

Preparation of compound 238, GROUP 2, CHART J, p. 2, Scheme X

*946 (1.45 g, 1.25 mmol), $CH_2Cl_2$ (100 mL) and TFA (25 mL) are combined according to the general procedure for removing a BOC protecting group described earlier to give *238 (1.32 g, ~100%) as a clear, colorless, viscous oil. $^1H$ NMR (400 MHz, $CDCl_3$) δ 0.78–1.02 (~6d, 24H), 1.15–1.96 (m, 18H), 2.40 (s, 3H), 2.43–3.33 (m, 12H), 3.48 (m, 1H), 4.91 (dd, J=5.17, 10.6, 1H), 5.00–5.39 (m, 7H), 5.49 (m, 1H), 7.10–7.40 (m, 15H). Mass spec (FAB). Calcd m/z for $C_{59}H_{82}N_4O_{13}+H_1$:1055.5956. Found: 1055.5920.

Preparation of compound 239, GROUP 2, CHART J, p. 2, Scheme X

*238 (1.29 g, 1.22 mmol), 10% Pd on carbon (225 mg) and absolute EtOH (150 mL) are combined according to the general hydrogenolysis procedure described earlier to give *239 (1.14 g, 97%) as a tan-colored powder. $^1H$ NMR (400 MHz, $CDCl_3$) δ 0.75–1.20 (m, 24H), 1.20–2.02 (m, 14H), 1.28 (d, J=7.06, ~2.5H), 1.41 (d, J=6.82, ~0.5H), 2.30–3.52 (m, ~9H), 2.51 (s, ~1H), 2.56 (s, ~1H), 2.72 (s, ~1H, 2.80 (s, ~1H), 2.88 (s, ~1H), 3.00 (s, ~1H), 3.60 (m, 1H), 4.76–4.90 (m, 1H), 5.06–5.51 (m, 5H), 5.57 (dd, J=7.09, 13.8, 1H), 6.88 (bs, 2H), 7.11–7.32 (m, 10H). Mass spec (FAB). Calcd m/z for $C_{52}H_{76}N_4O_{13}+H_1$:965.5487. Found: 965.5464.

Preparation of compound 919, GROUP 2, CHART J, p. 2, Scheme X

*239 (1.11 g, 1.15 mmol) is dissolved in $CH_2Cl_2$ (1150 mL) to give a concentration of 1 mM and the solution cooled to 0°. BOP reagent (534 mg, 1.21 mmol) is added and stirred until completely dissolved. NMM (0.13 mL, 1.21 mmol) is added and the reaction mixture stirred at 0° for 30 minutes and then for 3 days at room temperature. The reaction mixture is concentrated to about 100 mL and washed with saturated $NH_4Cl$ (250 mL). The layers are separated and the organic layer dried ($MgSO_4$), filtered through Celite and concentrated. The residue is dissolved in EtOAc and again concentrated. Drying under high vacuum gives a light, tan-colored foam. This is further purified by chromatography to give *919 (289 mg, 27%) as a white solid. $^1$H NMR (400 MHz, CDCl$_3$) δ 0.75–1.00 (m, 24H), 1.00–1.80 (m, 14H), 1.05 (d, J=6.33, ~0.7H), 1.12 (d, J=6.89, ~0.8H), 1.47 (d, J=6.82, 1.5H), 2.80 (s, 2.2H), 2.81 (s, 1.4H), 2.82 (s, 1.3H), 2.86 (s, 1.4H), 2.88 (s, 1.7H), 3.01 (s, 1H), 3.01–3.50 (m, 6H), 4.44 (m, 1H), 4.73–5.71 (m, 7H), 7.17–7.34 (m, 10H). Mass spec (FAB) m/z 947 [M+H], 1079 [M+Cs]. Calcd m/z for $C_{52}H_{74}N_4O_{12}+Na_1$:969.5201. Found: 969.5228.

THE REACTIONS OF GROUP 3

This section describes Group 3 reactions. Many times the product of Group 3 reactions will be the same as, similar to, or related to, the product of Group 2 reactions; however, the precise steps or the order of Group 3 reactions may be different from Group 2 reactions. Actual Charts showing chemical formula and reaction steps are consolidated with all the other tables, charts and reactions steps and are located in the section titled, "TABLES OF COMPOUNDS AND REACTION CHARTS." Group 3 Tables and Charts follow Group 2 which follows Group 1.

The ring nucleus may be comprised of eight residues (four of N-methyl-L-leucine, two of D-lactic acid, and two of 3-phenyl-D-lactic acid) in a floppy, 24-membered ring with alternating amide and ester bonds. We introduced a methylene group between the N-methyl group of a leucine residue and the methyl group of its adjacent lactic acid to produce compounds containing one or more delta-lactam rings thereby reducing the number of conformations the macrocyclic ring can adopt. Retrosynthetic analysis of the delta-lactam intermediate required for analog preparation suggested methyl 5-bromovalerate as a reasonable starting material. Conversion of this to a secondary amine incorporating L-leucine and subsequent cyclization produces a lactam. A two step hydroxylation procedure leads to a delta-lactam intermediate in which only one of the two chiral centers is controlled. Oxidation at the uncontrolled chiral center followed by a stereoselective reduction gives the final delta-lactam intermediate in which the required diastereomer is predominant.

Methyl 5-bromovalerate 1 and the benzyl ester of L-leucine, 2, were heated in DMF to 130° in the presence of powdered sodium bicarbonate for 90 minutes to give secondary amine 3 (91%) (Scheme 1). This, in turn, was heated under reflux in xylene for 18 hours to give lactamized intermediate 4 (66%). Attempts to directly oxidize the alpha position of this material using a Davis reagent failed. Instead, the alpha position was brominated using trimethylchlorosilane, triethylamine, iodine and bromine in methylene chloride to give 5 (77–94%). Hydrolysis of 5 was accomplished by heating it in DMF containing 1 equivalent of water at 150° for 65 minutes which produced delta-lactam intermediate 6 (75–86%) as a 1:1 mixture of R,S and S,S diastereomers. In one instance in which the reaction time was prolonged the formate ester of 6 (21%) was produced to the detriment of 6 itself (53%). Since our analog work required a single diastereomer, we performed a Swern oxidation on 6 which gave the alpha-keto delta-lactam 7 (70%); a subsequent reduction with Baker's yeast and D-glucose produced the S,S diastereomer, 8 (59–68%), in 70–95% de. The stereochemistry was unambiguously established by comparison of this material with that from an earlier, low-yield synthesis in which both chiral centers were introduced using optically pure starting materials; the yields from this earlier synthesis were such that it was unsuitable as a source of large amounts of delta-lactam 8.

Elaborated delta-lactam

Delta-lactam 8 is elaborated to a tetradepsipeptide having a particular residue sequence. This is accomplished in part by attaching a BOC protected N-methyl-L-leucine residue to the O-terminus of delta-lactam 8 with concomitant inversion of configuration at the alpha position (DEAD, Ph$_3$P, THF, 84%) to give 9. The benzyl protecting group is removed by hydrogenolysis (10% Pd/C, EtOH, 99%) from the C-terminus giving 10 after which 3-phenyl-D-lactic acid benzyl ester is attached (DCC, DMAP, CH$_2$Cl$_2$, 48%) to give the elaborated delta-lactam, 11, which is a useful intermediate.

Mono-delta-lactam Analog (Scheme 2)

The benzyl protecting group is removed from the C-terminus of 420 by hydrogenolysis (10% Pd/C, EtOH, 97%) to give carboxylic acid 13. The BOC protecting group is removed from the elaborated delta-lactam, 11, to give the corresponding free amine, 12, (20% TFA, CH$_2$Cl$_2$, 94%). The free amine and the carboxylic acid are combined (DCC, DMAP, CH$_2$Cl$_2$, 63%) to give octadepsipeptide 14. Both protecting groups are removed using the above methods starting with removal of the BOC group to give 15 (99%) and subsequent removal of the benzyl group to give 16 (97%). Compound 16 is then lactamized (BOPCl, DPEA, CH$_2$Cl$_2$, 65%) to give the mono-delta-lactam analog, 17.

ADDITIONAL DETAILS, DESCRIPTIONS AND PROCEDURES USED TO PREPARE THE GROUP 3 COMPOUNDS, WITH EXAMPLES

Preparation of the Secondary Amine (3)

Methyl 5-bromovalerate (5.47 g, 28 mmols), L-leucine benzyl ester (6.21 g, 28 mmols) and sodium bicarbonate (4.71 g, 56 mmols) were combined in dry DMF (25 mL) and the resulting mixture heated at 130° for 90 minutes. The reaction mixture was cooled to room temperature, diluted with water and extracted three times with ether. The extracts were combined and washed, in turn, with water and sat. sodium chloride. After drying over anhydrous sodium sulfate, the mixture was filtered and the filtrate concentrated to give the secondary amine (8.53 g, 91% yield) as a clear, pale-yellow oil.

Preparation of the Deltalactam (4)

The secondary amine (8.53 g, 25) was combined with dry xylene (25 mL) and heated under reflux for 18 hours. The reaction mixture was concentrated and subjected to silica gel chromatography (20–30% ethyl acetate in hexane) to give the deltalactam (5.10 g, 66% yield) as a clear, light-yellow oil.

Preparation of the α-bromodeltalactam (5).

To a solution of the deltalactam (8.66 g, 28.5 mmols) in dry methylene chloride (220 mL) was added triethylamine (19.9 mL, 143 mmols) and the solution cooled to −15°. Chlorotrimethylsilane (7.2 mL, 57.0 mmols) was added dropwise during five minutes and the reaction mixture stirred five minutes. Solid iodine (10.9 g, 42.8 mmols) in the form of small crystals was added all at once and the mixture stirred 15 minutes at −15°. Bromine (11.0 mL, 214 mmols) was added and the reaction mixture stirred at 0° for 100 min. The reaction mixture was washed with a 10% solution of sodium sulfite (2×300 mL). The aqueous layers were combined and extracted with methylene chloride. The combined organic layers were washed with sat. sodium chloride, dried over anhydrous sodium sulfate and concentrated. Silica gel chromatography (20% ethyl acetate in hexane) gave the α-bromodeltalactam (4.20 g, 85% yield) as a clear, very pale-yellow oil.

Preparation of the α-hydroxydeltalactam (6)

The α-bromodeltalactam (3.82 g, 10.0 mmols) was dissolved in dry formamide (75 mL) and water (0.18 mL, 10.0 mmols) added. The reaction mixture was heated at 150° for 65 minutes. (The reaction was monitored by TLC; prolonged heating produces the formate ester of the product.) The reaction mixture was cooled to room temperature, diluted with water and extracted with ether three times. The extracts were combined, washed with water twice and then with sat. sodium chloride and finally dried over anhydrous sodium sulfate. Silica gel chromatography (40% ethyl acetate in hexane) gave the α-hydroxydeltalactam (2.76 g, 87% yield) as a clear, light-yellow oil.

Preparation of the α-ketodeltalactam (7)

A solution of dry dimethylsulfoxide (0.93 mL, 13.1 mmols) in methylene chloride (3 mL) was slowly added to a solution of oxalyl chloride (0.56 mL, 6.54 mmols) in methylene chloride (12 mL) at −78°. After stirring ten minutes, a solution of the α-ketodeltalactam (1.90 g, 5.95 mmols) in methylene chloride (4 mL) was added dropwise and the reaction mixture stirred at −78° for 60 minutes. Triethylamine (3.6 mL, 26.2 mmols) was slowly added and the mixture stirred at ambient temperature for 45 minutes. The mixture was poured into water and extracted twice with methylene chloride. The extracts were combined and washed in turn with 1N sulfuric acid and sat. sodium bicarbonate. The extracts were dried over anhydrous sodium sulfate and the solvent removed leaving a light brown oil which solidified on standing. The oil was triturated with hexane containing a small amount of ethyl acetate while warming on a steam bath. After chilling at 0° for several hours, the solid was removed by filtration and air dried to give the α-ketodeltalactam (1.33 g, 70% yield) as a white crystalline solid.

Preparation of the α-(R)-hydroxydeltalactam (8)

Baker's yeast (60 g) and D-glucose (6 g) were combined in a 1 L Erlenmeyer flask. Water (160 mL) was added and the mixture swirled until the yeast was completely wetted (about one minute). The α-ketodeltalactam (3.03 g, 9.55 mmols) was added as a solid and mixed thoroughly with the yeast. The mixture was divided between two flasks when the fermentation threatened to overflow its container. The reaction mixtures were stirred overnight at room temperature. The mixtures were vacuum filtered through a celite pad. When the water had been mostly removed, the solids were mixed with a large amount of sand to increase the surface area of the solids. The resulting granular solid was stirred several times with ethyl acetate and filtered. The filtrates were combined and partially dried over anhydrous sodium sulfate. Residual water was removed azeotropically with ethyl acetate giving a brown oil which partially solidified on standing at room temperature. Silica gel chromatography (20–40% ethyl acetate in hexane) produced an amber colored oil. The oil was triturated with warm hexane giving a fine powder. Chilling at 0°, filtration and drying at 60° under vacuum gave predominantly the α-R)-hydroxydeltalactam (1.52 g, 50% yield) as a tan-colored powder. The stereoselectivity varied from reaction to reaction and ranged from 70% de to >95% de based on $^{13}$C NMR.

Preparation of the MeLeu-Deltalactam (9)

Triphenylphosphine (1.22 g, 4.66 mmols) was added to a solution of N-BOC-N-methyl-L-leucine (1.14 g, 4.66 mmols) and α-(R)-hydroxydeltalactam (1.49 g, 4.66 mmols) in THF (25 mL). The mixture was cooled to 0° and diethylazodicarboxylate (0.88 mL, 5.60 mmols) added. The reaction mixture was stirred at room temperature for two hours and then concentrated to a mixture of oil and solid. This was chromatographed on silica gel (20% ethyl acetate in hexane) to give the MeLeu-Deltalactam (2.14 g, 84% yield) as a clear, colorless oil. $^1$H NMR (400 MHz, CDCl$_3$) δ 0.93 (3d, 12 H), 1.45 (s, 9 H), 1.48–2.19 (m, 10 H), 2.79 (m, 3 H), 3.22 (m, 2 H), 4.69–5.27 (m, 2 H), 5.08 (d, J=12.3 Hz, 1 H), 5.17 (d, J=12.3 Hz, 1 H), 5.30 (m, 1 H), 7.32 (m, 5 H).

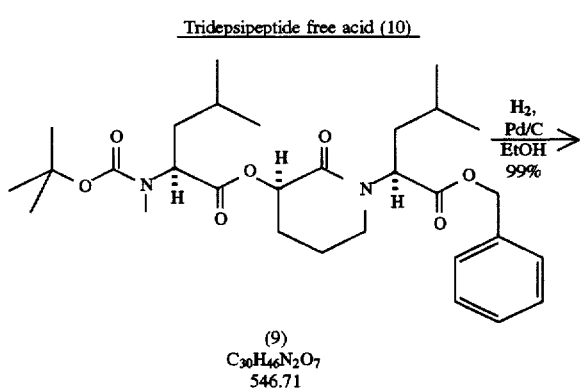

(9)
C$_{30}$H$_{46}$N$_2$O$_7$
546.71

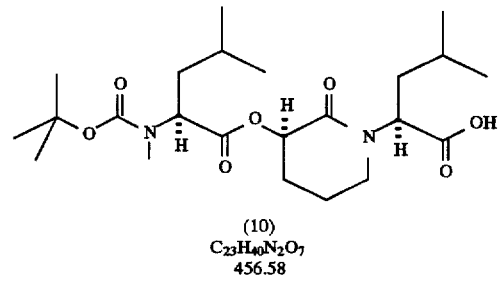

(10)
C$_{23}$H$_{40}$N$_2$O$_7$
456.58

Tridepsipeptide (10) (2.11 g 3.86 mmol), EtOH (100 mL) and 10% Pd on carbon (300 mg) were combined and processed according to the general procedure for removing a benzyl protecting group described earlier. This produced 1.83 g of white foam and glass which $^1$H NMR showed to contain 95 wt % product and 5 wt % EtOAc. This amounts to 1.74 g (99%) of free acid (10). $^1$H NMR (400 MHz, CDCl$_3$) δ 0.93 (3d, 12 H), 1.38–2.24 (m, 10 H), 1.45 (s, 9 H), 2.76 (2s, 3 H), 3.30 (bs, 2 H), 4.73 (m, 0.5 H), 4.93 (m, 0.5 H), 5.22 (m, 2 H), 9.40 (bs, 1 H).

Tetradepsipeptide (11)

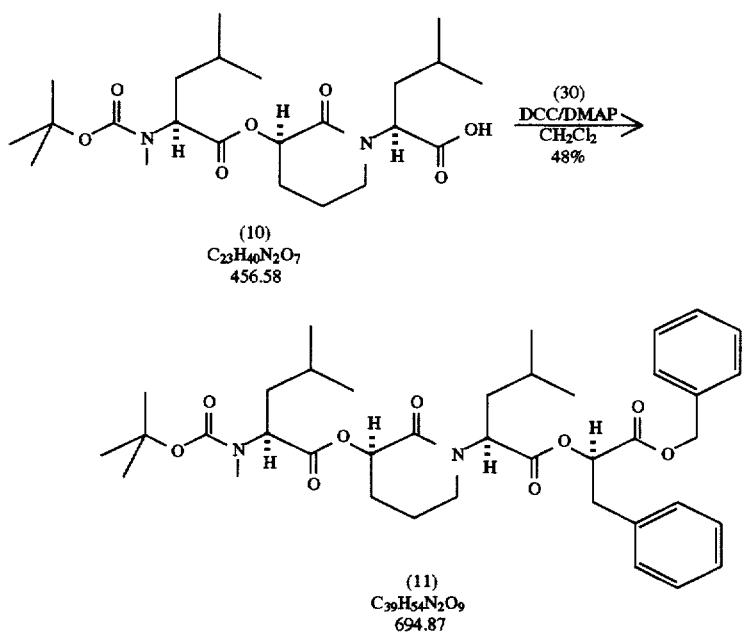

Tridepsipeptide free acid (10) (1.71 g, 3.75 mmol), phenyllactic acid benzyl ester (0.96 g, 3.75 mmol), a solution of DCC (1M, 4.1 mL, 4.1 mmol), DMAP (23 mg, 0.19 mmol) and dry $CH_2Cl_2$ (50 mL) were combined and processed according to the general procedure for coupling peptides using DCC described earlier. The crude reaction product was subjected to silica gel chromatography (15–20% EtOAc in hexane) which produced from the appropriate fraction 1.28 g of clear, colorless oil. $^1$H NMR showed this to contain 98 wt % product and 2 wt % EtOAc. This amounts to 1.25 g (48%) of tetradepsipeptide (11). HPLC analysis showed this material to consist of a 11:1 mixture of diastereomers. $^1$H NMR (400 MHz, $CDCl_3$ δ 0.93 (3d, 12 H), 1.46 (s, 9 H), 1.35–2.03 (m, 10 H), 2.80 (2s, 3 H), 3.01 (m, 2 H), 3.16 (m, 2 H), 4.70–5.55 (m, 6 H), 7.12 (m, 2 H), 7.27 (m, 5 H), 7.36 (m, 3 H). A second fraction (0.82 g) contained a different mix of diastereomers.

Tetradepsipeptide free amine (12)

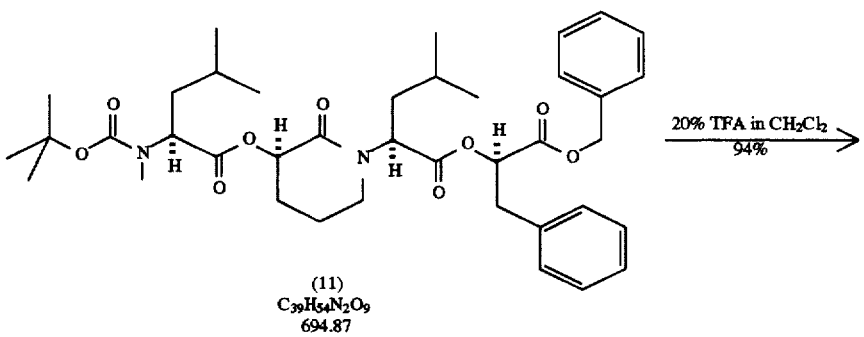

-continued
Tetradepsipeptide free amine (12)

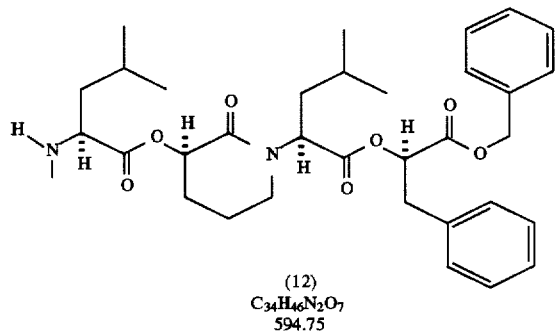

(12)
C$_{34}$H$_{46}$N$_2$O$_7$
594.75

Tetradepsipeptide (11) (600 mg, 0.863 mmol) and 20% TFA in CH$_2$Cl$_2$ (20 mL) were combined and processed according to the general procdure for removing a BOC protecting group as described earlier. This produced free amine (12) (483 mg, 94%). $^1$H NMR (400 MHz, CDCl$_3$) δ 0.93 (4d, 12 H), 1.37–2.37 (m, 11 H), 2.47 (s, 3 H), 2.96–3.02 (m, 2 H), 3.15 (m, 2 H), 3.33 (t, J=7.25 Hz, 1 H), 5.10 (d, J=12.1 Hz, 1), 5.15 (d, J=12.0 Hz, 1 H), 5.21–5.33 (m, 2 H), 5.43 (dd, J=5.20, 10.4 Hz, 1 H), 7.11 (m, 2 H), 7.27 (m, 5 H), 7.37 (m, 3 H).

Tetradepsipeptide free acid (13)

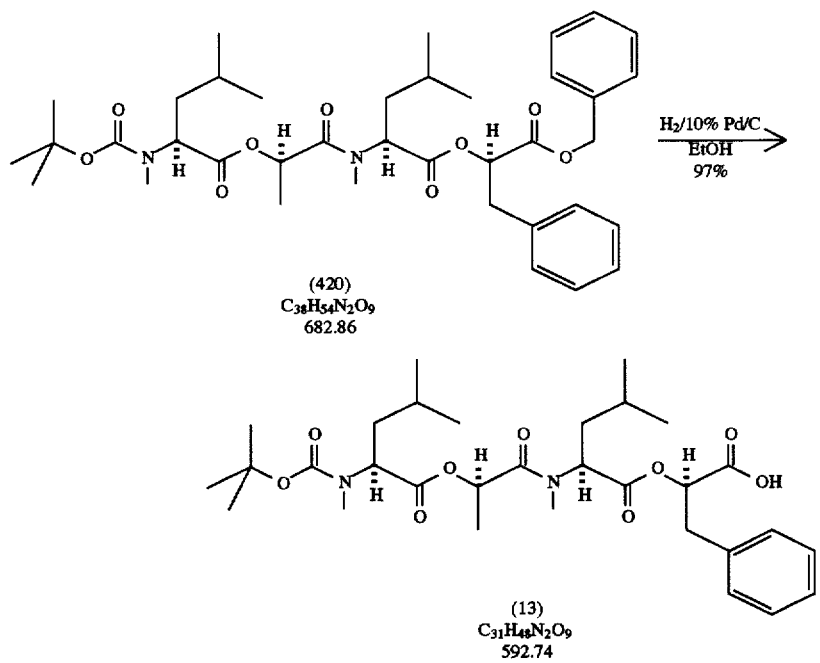

(420)
C$_{38}$H$_{54}$N$_2$O$_9$
682.86

(13)
C$_{31}$H$_{48}$N$_2$O$_9$
592.74

Tetradepsipeptide (*420) (600 mg, 0.879 mmol), EtOH (100 mL) and 10% Pd on carbon (80 mg) were combined and processed according to the general procedure for removing a benzyl protecting group described earlier. This gave 523 mg of white solid foam. $^1$H NMR showed this to contain 97 wt % product and 3 wt % EtOAc which amounts to 507 mg (97%) of free acid (13). $^1$H NMR (400 MHz, CDCl$_3$) δ 0.89 (4d, 12 H), 1.31–1.85 (m, 9 H), 1.42 (4s, 9 H), 2.77–3.00 (5s, 6 H), 3.00–3.40 (m, 2 H), 4.40–5.55 (m, 4 H), 7.24 (m, 5 H), 7.55 (bs, $^1$H).

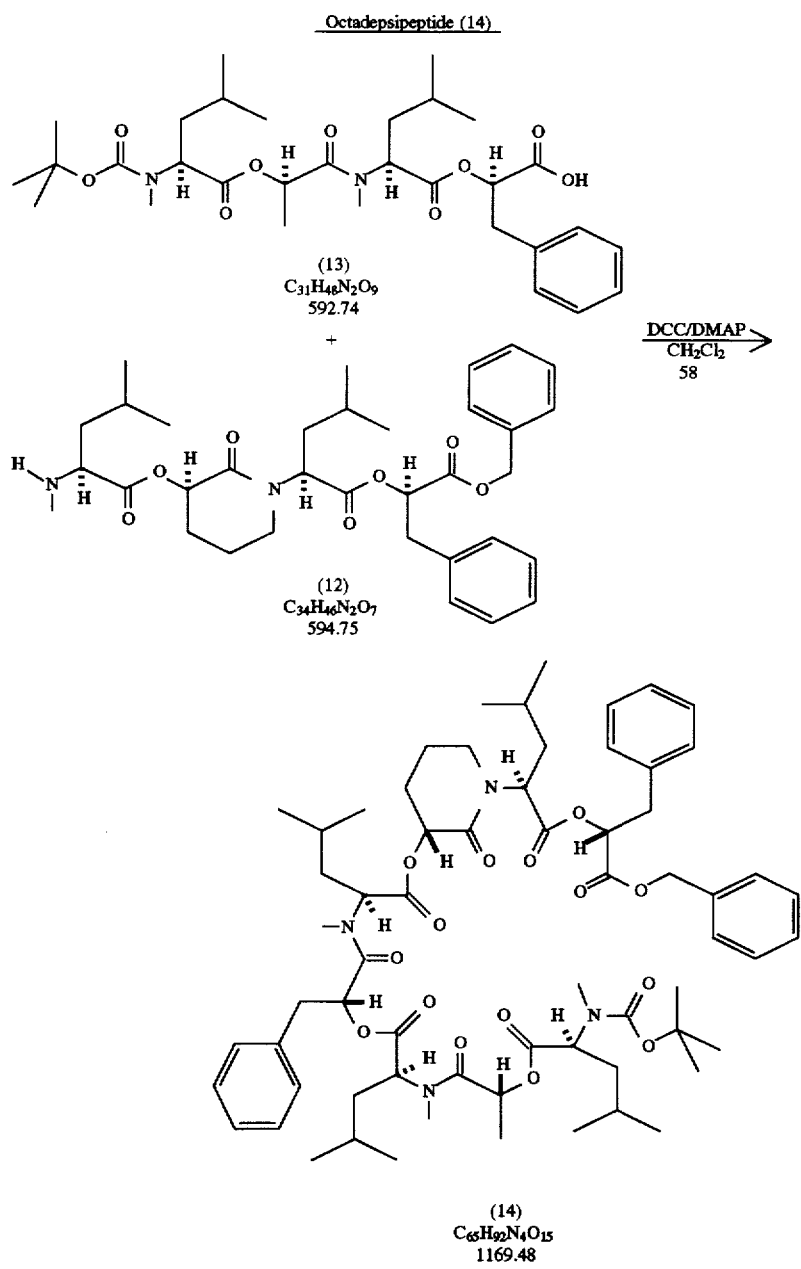

Tetradepsipeptide free acid (13) (461 mg, 0.778 mmol), tetradepsipeptide free amine (12) (463 mg, 0.778 mmol), a solution of DCC (1.0M, 0.8 mL, 0.8 mmol) in $CH_2Cl_2$ and DMAP (4.8 mg, 0.039 mmol), and dry $CH_2Cl_2$ (20 mL) were combined and processed according to the general procedure for coupling peptides using DCC as described earlier. This produced a solid foam and glass (940 mg) which was purified by silica gel chromatography (25–30% EtOAc in hexane). From the appropriate fraction there was obtained 576 mg of clear, yellow oil which $^1H$ NMR showed to contain 92 wt % product and 8 wt % EtOAc. This amounts to 530 mg (58%) of octadepsipeptide (14). $^1H$ NMR (400 MHz, $CDCl_3$) δ 0.87 (5s, 24 H), 1.30–2.01 (m, 19 H), 1.45 (m, 9 H), 2.75–3.28 (2s+m, 15 H), 4.41–5.50 (m, 8 H), 5.09 (d, J=12.0 Hz, 1 H), 5.14 (d, J=12.0 Hz, 1 H), 7.05–7.44 (m, 15 H).

Octadepsipeptide free amine (15)
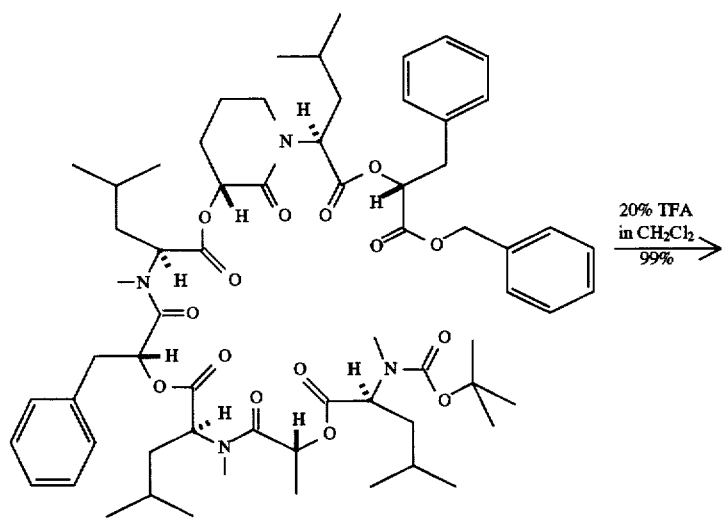
20% TFA
in CH₂Cl₂
99%
(14)
C₆₅H₉₂N₄O₁₅
1169.48
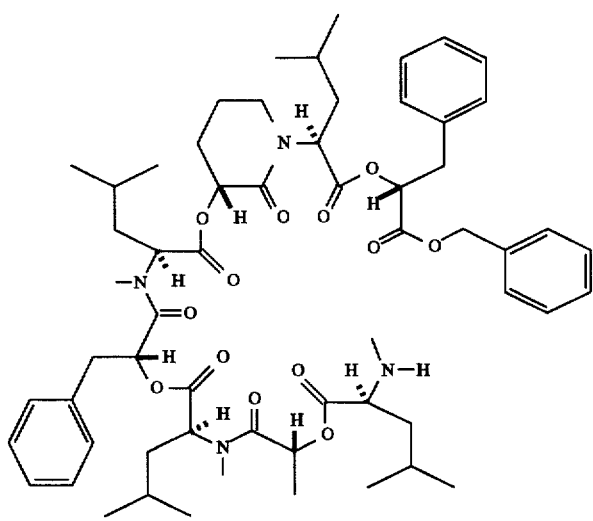
(15)
C₆₀H₈₄N₄O₁₃
1069.36
Octadepsipeptide (14) (512 mg, 0.437 mmol) and 20% TFA solution (20 mL) were combined and processed according to the general procedure for removing a BOC protecting group described earlier. This gave free amine (15) (462 mg, 99%). $^1$H NMR (400 MHz, CDCl₃) δ 0.78–1.05 (5d, 24 H), 1.17–2.12 (m, 20 H), 2.40–3.30 (3s+m, 15 H), 3.47 (m, 1 H), 5.09 (d, J=12.1 Hz, 1 H), 5.14 (d, J=12.0 Hz, 1 H), 5.19–5.57 (m, 7 H), 7.03–7.41 (m, 15 H).

Octadepsipeptide amino acid (16)

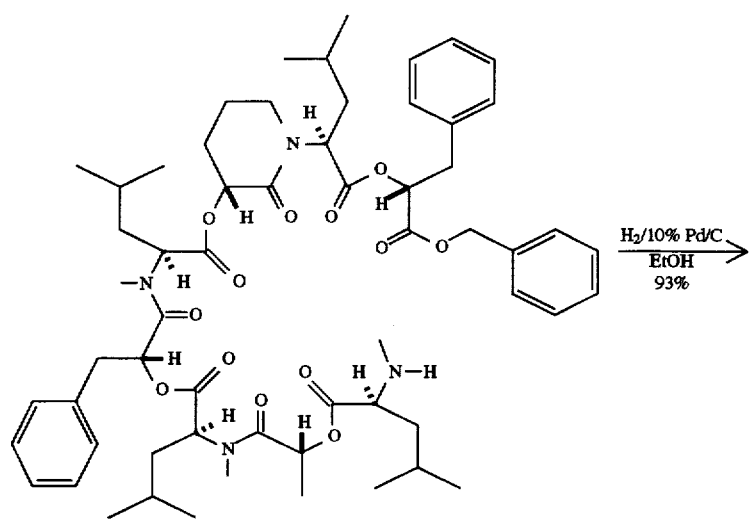

(15)
$C_{60}H_{84}N_4O_{13}$
1069.36

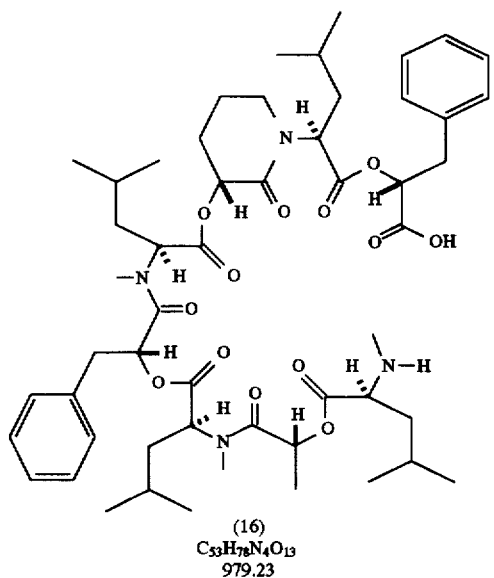

(16)
$C_{53}H_{78}N_4O_{13}$
979.23

Octadepsipeptide free amine (15) (452 mg, 0.423 mmol), EtOH (100 mL) and 10% Pd on carbon (80 mg) were combined and processed according to the general procedure for removing a benzyl protecting group as described earlier. This produced 403 mg of cream-colored solid which $^1$H NMR showed to consist of 96 wt % product and 4 wt % EtOAc. This amounts to 387 mg (93%) of amino acid (16). $^1$H NMR (400 MHz, CDCl$_3$) δ 0.78–1.08 (4d, 24 H), 1.28 (m, 4 H), 1.40–2.02 (m, 16 H), 2.43–2.70 (s+m, 3 H), 2.70–3.38 (2s+m, 12 H), 3.74 (m, 1 H), 5.00–5.60 (m, 7 H), 6.69 (bs, 1 H), 7.25 (m, 10 H).

17 or *312 via macrolactamization

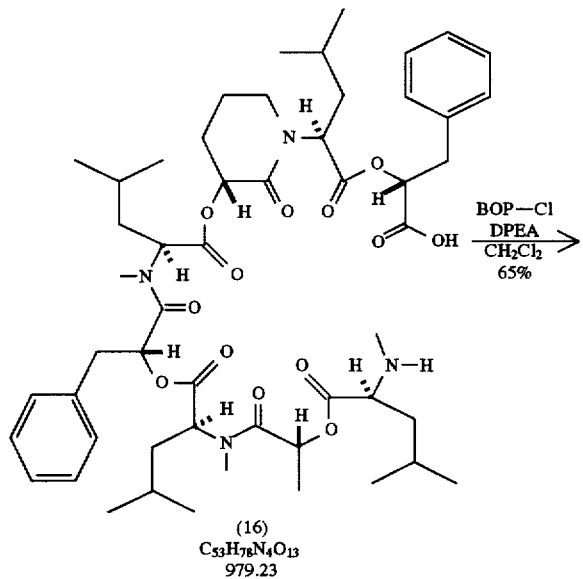

(16)
C53H78N4O13
979.23

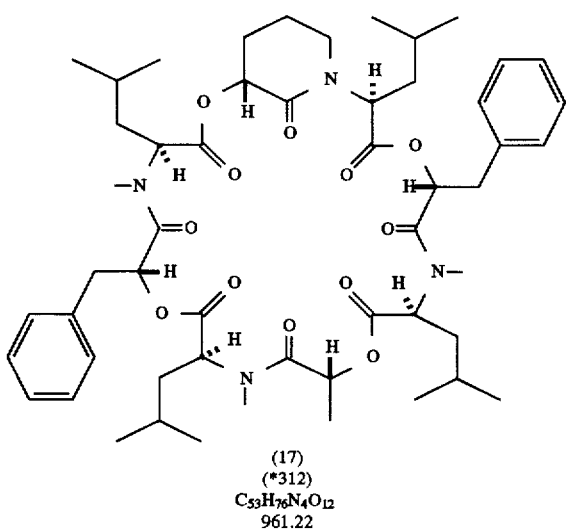

(17)
(*312)
C53H76N4O12
961.22

Octadepsipeptide amino acid (17 or *312) (388 mg, .0396 mmol), DPEA (172 μL, 0.998 mmol), BOP-Cl (121 mg, 0.475) and $CH_2Cl_2$ (400 mL) were combined and processed according to the general procedure for coupling peptides using BOP-Cl as described earlier. This produced a solid foam which was dissolved in EtOAc and filtered to remove the insoluble material. The filtrate was concentrated to an off-white foam which was further purified by silica gel chromatography (40–50% EtOAc in hexane). From the appropriate fraction there was obtained an oil which was twice dissolved in a 4:1 mixture of hexane to $CH_2Cl_2$ and concentrated and finally dried under high vacuum to give (17 or *312) (249 mg, 65%) as a nearly colorless foam and glass (cf. 28983-FED-122). HPLC analysis showed this material to be 99.8% pure and free of any diastereomers. $^1$H NMR showed the product to consist of a mixture of conformers. $[\alpha]_D$ –87° (c 1.0, MeOH). $^1$H NMR (400 MHz, CDCl3) δ 0.70–1.20 (m, 27 H), 1.20–2.30 (m, 19 H), 2.67–3.00 (5s, 9 H), 3.00–3.37 (m, 6 H), 4.44 (m, 1 H), 4.78 (m, 0.5 H), 5.05 (m, 0.5 H), 5.18–5.45 (m, 4 H), 5.55–5.68 (m, 1 H), 5.80–5.90 (m, 1 H), 7.25 (m, 10 H); Mass spec (FAB) m/z 961 [M+H], 983 [M+Na], 1093 [M+Cs].

ALTERNATE LAST STEP

Preparation of Compound 17 or *312 of Group 3

16 (388 mg, 0.396 mmol) was dissolved in $CH_2Cl_2$ (400 mL) and diisopropylethylamine (0.17 mL, 0.99 mmol) added. The solution was cooled to 0° and treated with BOPCl (121 mg, 0.475 mmol). The reaction mixture was stirred at room temperature overnight. When TLC showed the reaction to be incomplete, another portion of diisopropylethylamine and BOPCl were added and the reaction mixture stirred for 24 hours longer for a total reaction time of 48 hours. The reaction mixture was washed with sat. sodium bicarbonate. The organic layer was filtered through a cone of sodium sulfate and further dried over magnesium sulfate. Filtration through celite followed by concentration gave a solid foam and glass. Silica gel chromatography (40–50% ethyl acetate in hexane) gave 17 or *312 (249 mg, 65%) as a white solid foam. $^1$ H NMR (400 MHz, CDCl$_3$) δ 0.65–1.20 (m, 24H), 1.20–2.30 (m, 19H), 2.71 (s, ~1H), 2.77 (s, ~1.5H), 2.78 (s, ~1.5H), 2.83 (s, ~3H), 2.98 (s, ~2H), 3.00–3.26 (m, 5), 3.30 (m, 1H), 4.43 (m, ~0.5H), 5.07 (m, ~0.5H), 5.19–5.44 (m, 5H), 5.55–5.70 (m, 1H), 5.80–5.92 (m, 1H), 7.13–7.33 (10H). Mass spec (FAB) m/z 961 [M+H], 983 [M+Na], 1093 [M+Cs]. Calcd m/z for $C_{53}H_{76}N_4O_{12}+H_1$:961.5538. Found: 961.5538.

ANOTHER DETAILED SYNTHESIS OF A GROUP 3 COMPOUND

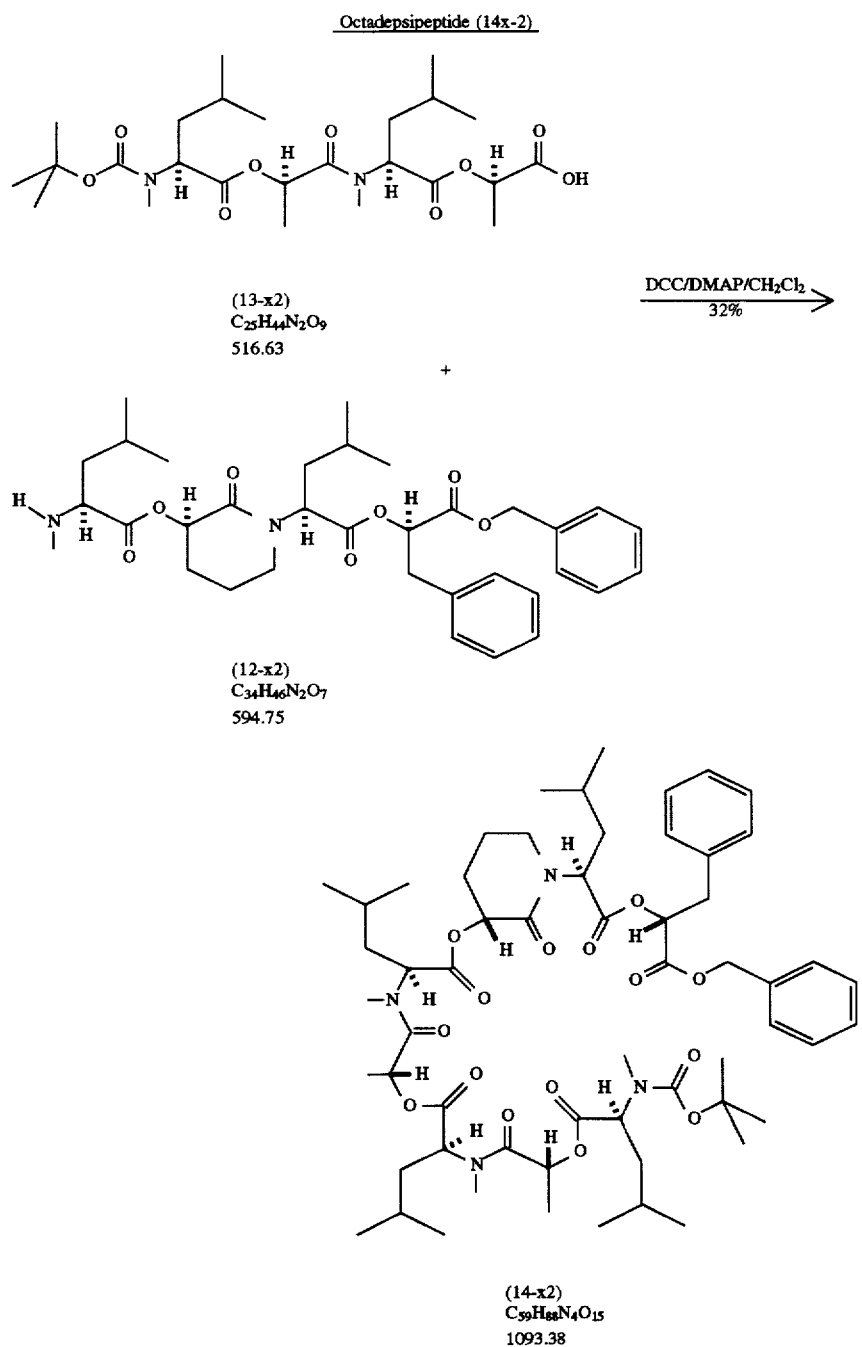

Tetradepsipeptide free acid (13-x2) (238 mg, 0.461 mmol), tetradepsidpetide free amine (12-x2) (274 mg, 0.461 mmol), DMAP (3.1 mg, 0.025 mmol), a solution of DCC in $CH_2Cl_2$ (1M, 0.51 mL, 0.51 mmol) and dry $CH_2Cl_2$ (10 mL) were combined and processed according to the general procedure for coupling peptides using DCC as described earlier. This produced a clear, yellow oil which was further purified by silica gel chromatography (25–40% EtOAc in hexane). The appropriate fraction was concentrated and dried under high vacuum to give 163 mg of viscous oil and solid. $^1$H NMR showed this material to consist of 98 wt % product and 2 wt % EtOAc which amounts to 160 mg (32%) of octadepsipeptide (14-x2). $^1$H NMR (400 MHz, $CDCl_3$) δ 0.81–1.05 (m, 24 H), 1.05–2.08 (2s+m, 31 H), 2.75–3.20 (2s+m, 13 H), 4.41–5.50 (m, 8 H), 5.09 (d, J=12.1 Hz, 1 H), 5.14 (d, J=12.0 Hz, 1 H), 7.04–7.40 (m, 10 H).

Octadepsipeptide free amine (15-x2)

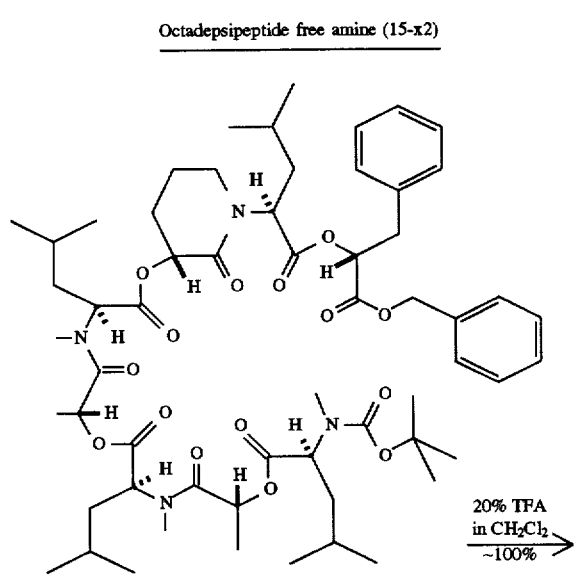

(14-x2)
C₅₉H₈₈N₄O₁₅
1093.38

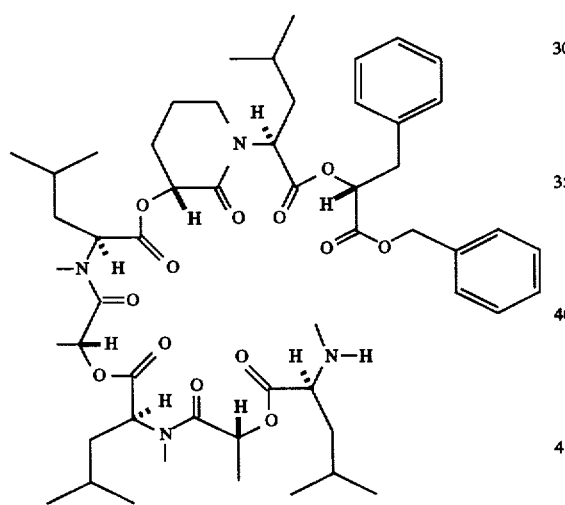

(15-x2)
C₅₄H₈₀N₄O₁₃
993.26

Octadepsipeptide amino acid (16-x2)

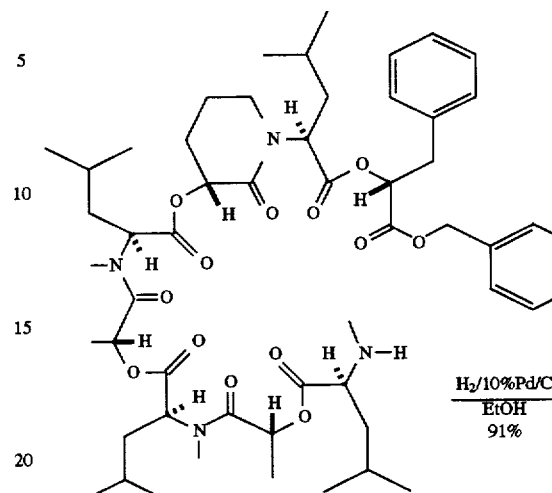

(15-x2)
C₅₄H₈₀N₄O₁₃
993.26

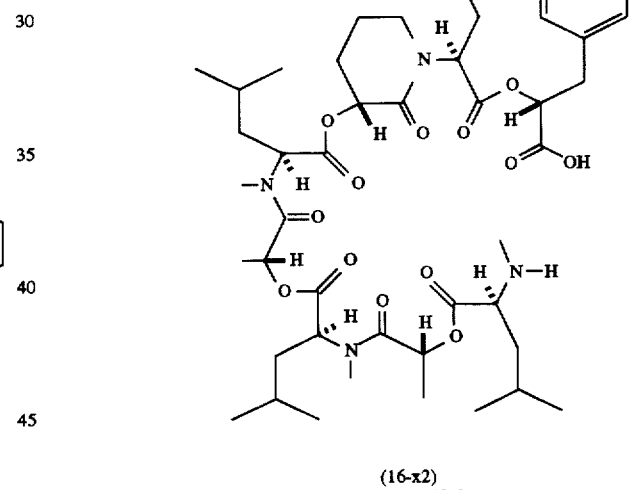

(16-x2)
C₄₇H₇₄N₄O₁₃
903.13

Octadepsipeptide (14-x2) (163 mg, 0.149 mmol) and a solution of 20% TFA in CH₂Cl₂ (10 mL) were combined and processed according to the general procedure for removing a BOC protecting group as described earlier. This gave free amine (15-x2) (156 mg, ~100%) which was used without further purification.

Octadepsipeptide (15-x2) (156 mg, 0.149 mmol), EtOH (100 mL) and 10% Pd on carbon (37 mg) were combined and processed according to the general procedure for removing a benzyl protecting group. The crude product was dissolved in EtOAc, concentrated and then dried under high vacuum. This removed all traces of EtOH to give 130 mg of material which ¹H NMR showed to consist of 95 wt % product and 5 wt % EtOAc. This amounts to 124 mg (91% yield over two reactions) of amino acid (16-x2). ¹H NMR (400 MHz, CDCl₃) δ 0.70–1.07 (m, 24 H), 1.07–2.10 (m, 22

H), 2.41–2.62 (s+m, 3 H), 2.81–3.52 (2s+m, 10 H), 3.68 (m, 1 H), 5.05–5.56 (m, 7 H), 6.46 (bs, 2 H), 7.24 (m, 5 H).

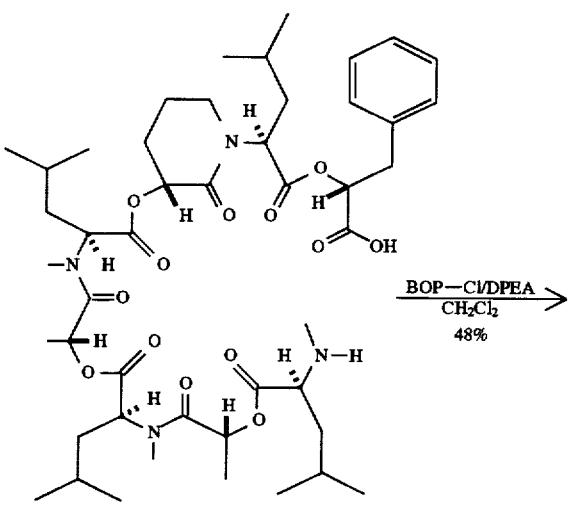

(16-x2)
$C_{47}H_{74}N_4O_{13}$
903.13

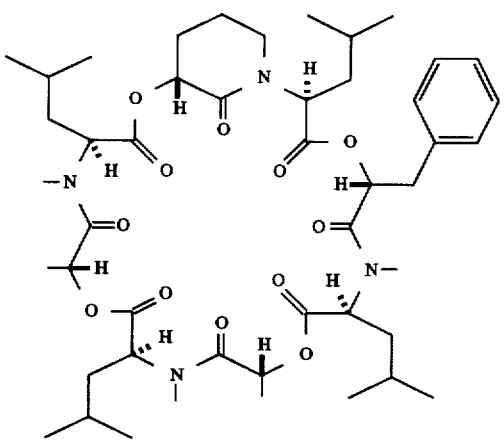

(17-x2 or *353)
$C_{47}H_{72}N_4O_{12}$
885.12

Octadepsipeptide amino acid (16-x2) (124 mg, 0.137 mmol), DPEA (60 µL, 0.343 mmol), BOP-Cl (42 mg, 0.164 mmol) and $CH_2Cl_2$ (140 mL) were combined and processed according to the general procedure for coupling peptides using BOP-Cl as described earlier. This produced 157 mg of cream-colored solid foam which was further purified by silica gel chromatography (50% EtOAc in hexane). From the appropriate fraction there was obtained CDP (17-x2 or *353) (58.8 mg (48%) as a white solid. $^1$H NMR showed the product to consist of a mixture of conformers. HPLC analysis showed the product to be 99.8% pure and free of any diastereomers. $[α]_D$ –57° (c 0.97, MeOH). $^1$H NMR (400 MHz, $CDCl_3$) δ 0.70–1.15 (m, 24 H), 1.15–2.25 (m, 22 H), 2.70–3.40 (6s+m, 13 H), 4.44 (m, 0.7 H), 4.71 (m, 0.6 H), 5.00–5.13 (m, 1 H), 5.26–5.46 (m, 3.4 H), 5.50 (m, 0.6 H), 5.65 (m, 1 H), 5.84 (m, .7 H), 7.24 (m, 5 H). Mass spec (FAB) m/z 885 [M+H], 907 [M+Na], 1017 [M+Cs]. Calc m/z for $C_{47}H_{72}N_4O_{12}$+$H_1$: 885.5225. Found: 885.5208.

TABLES OF COMPOUNDS AND REACTION CHARTS

The following Tables and Charts are provided. The Tables and Charts are intended to further illustrate the invention. Starting Materials are provided. The first Tables shows the formula of the starting materials and the first Chart shows the Starting Materials being combined in initial reactions. The Starting materials would all be commonly available to those skilled in the art, either through direct purchase from a chemical supplier, or after chemical synthesis using commonly available materials. Any synthesis required to make the starting materials would be a synthesis previously described and one that should be known or obvious to a skilled chemist. A Chart of Starting Reactions is then provided that shows the basic compounds and how they are combined to create more complex compounds needed to create the desired active compounds.

The starting materials are shown in generic form. These generic formula have various optionally substituted variables, usually "R" groups. The definition of these variables, the possible substituents for each variable, are provided in the Summary of the Invention.

---

TABLE OF STARTING MATERIALS
The following compounds, formula, tables, and reactions identify the starting materials for this invention. Formula are given a letter - number designations, such as "J-1" and basic combinations are shown, then the chemical formula is provided for appropriate letter - numbers, finally the full reactions are provided.

---

1) J-1 + J-2 → J-3 → J-4.
2) J-5 + J-6 → J-7 → J-8.
3) J-4 + J-8 → J-9 → J-10.
4) J-11 + J-12 → J-13 → J-14.
5) J-10 + J-14 → J-15 → J-16.
6) J-17 + J-18 → J-19 → J-20.
7) J-16 + J-20 → J-21 → J-22 → J-23 → FORMULA I
8) J-13 → K-1.
9) K-1 + J-20 → K-2 → K-3.
10) J-10 + K-3 → J-21 → J-22 → J-23 → FORMULA I
Chemical formula for J-1, J-2, J-5, J-6, J-11, J-12, J-17, J-18 are now provided. The variable definitions may be found in the summary of invention

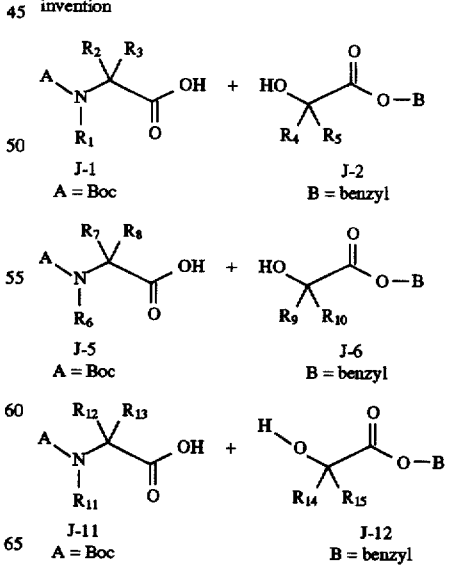

J-1
A = Boc

J-2
B = benzyl

J-5
A = Boc

J-6
B = benzyl

J-11
A = Boc

J-12
B = benzyl

-continued

TABLE OF STARTING MATERIALS

The following compounds, formula, tables, and reactions identify the starting materials for this invention. Formula are given a letter - number designations, such as "J-1" and basic combinations are shown, then the chemical formula is provided for appropriate letter - numbers, finally the full reactions are provided.

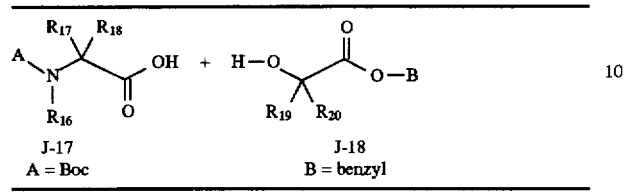

J-17  J-18
A = Boc  B = benzyl

The reactions of the starting materials are provided below, followed by the general reactions of this invention.

CHART S-1

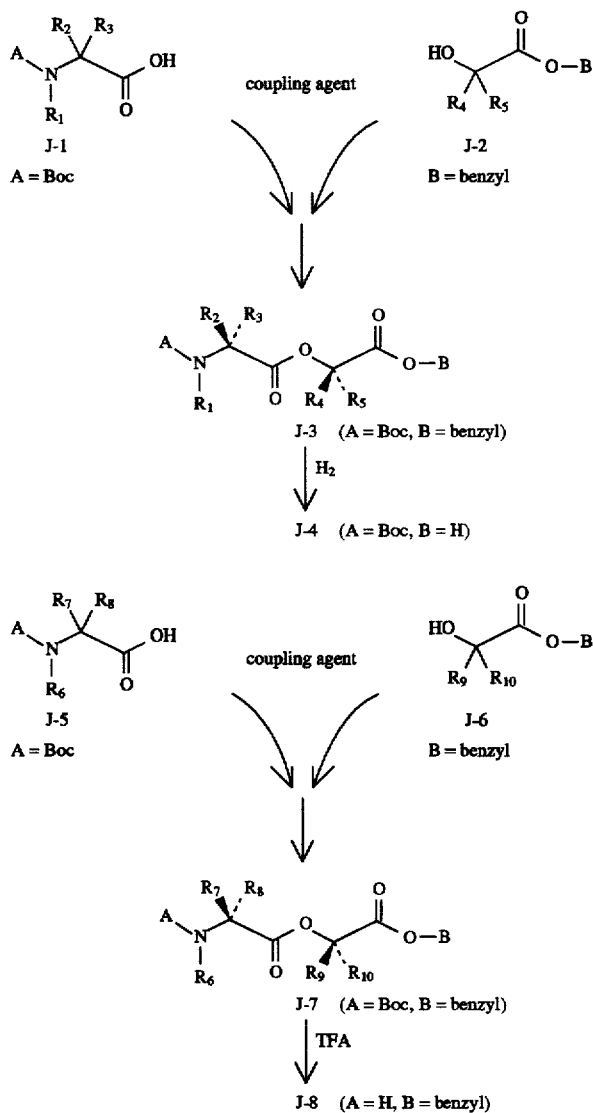

-continued
CHART S-1
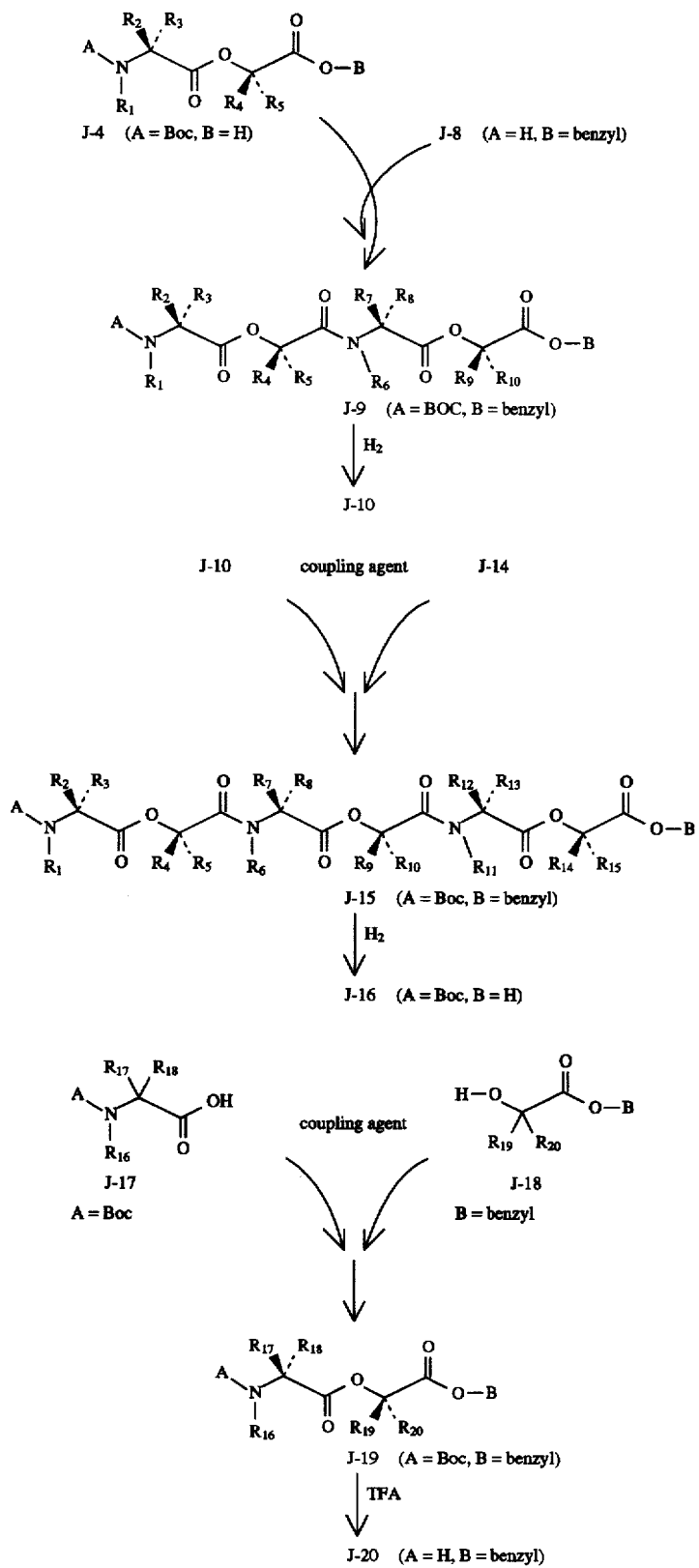

-continued
CHART S-1
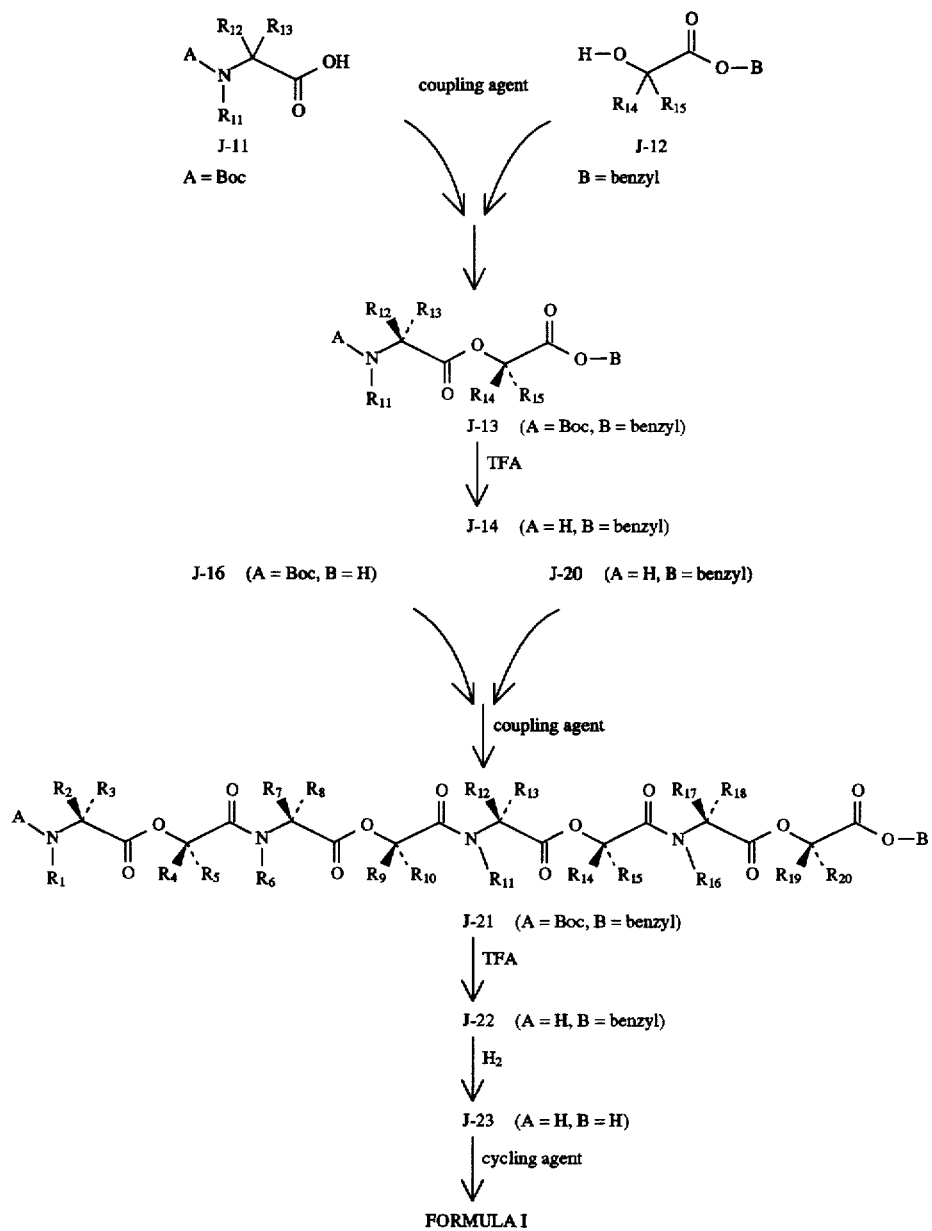
CHART S - 2
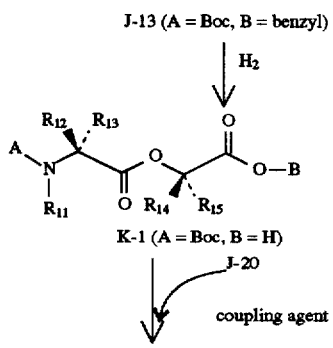

-continued
CHART S - 2
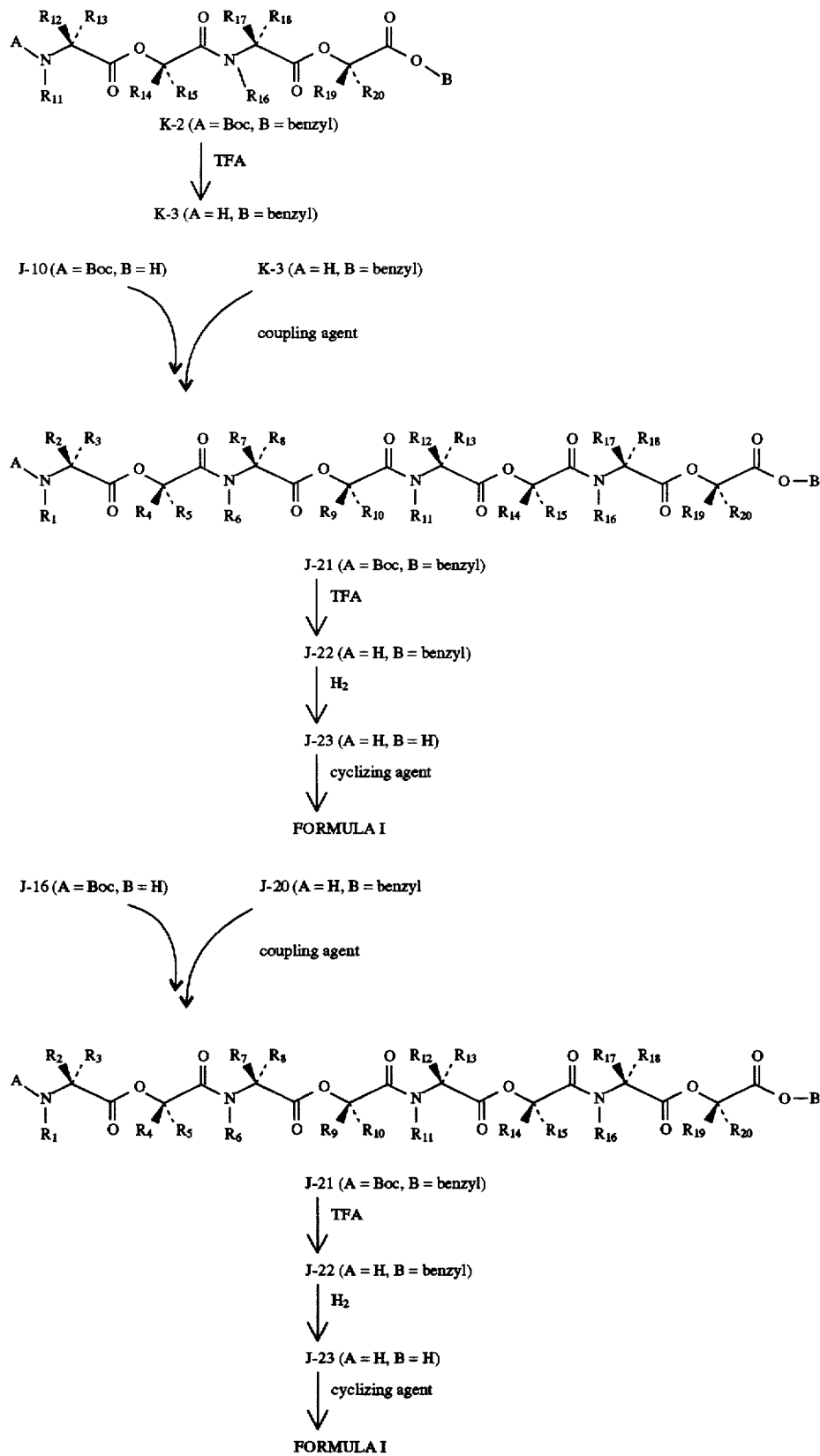

GROUP 1
CHART A
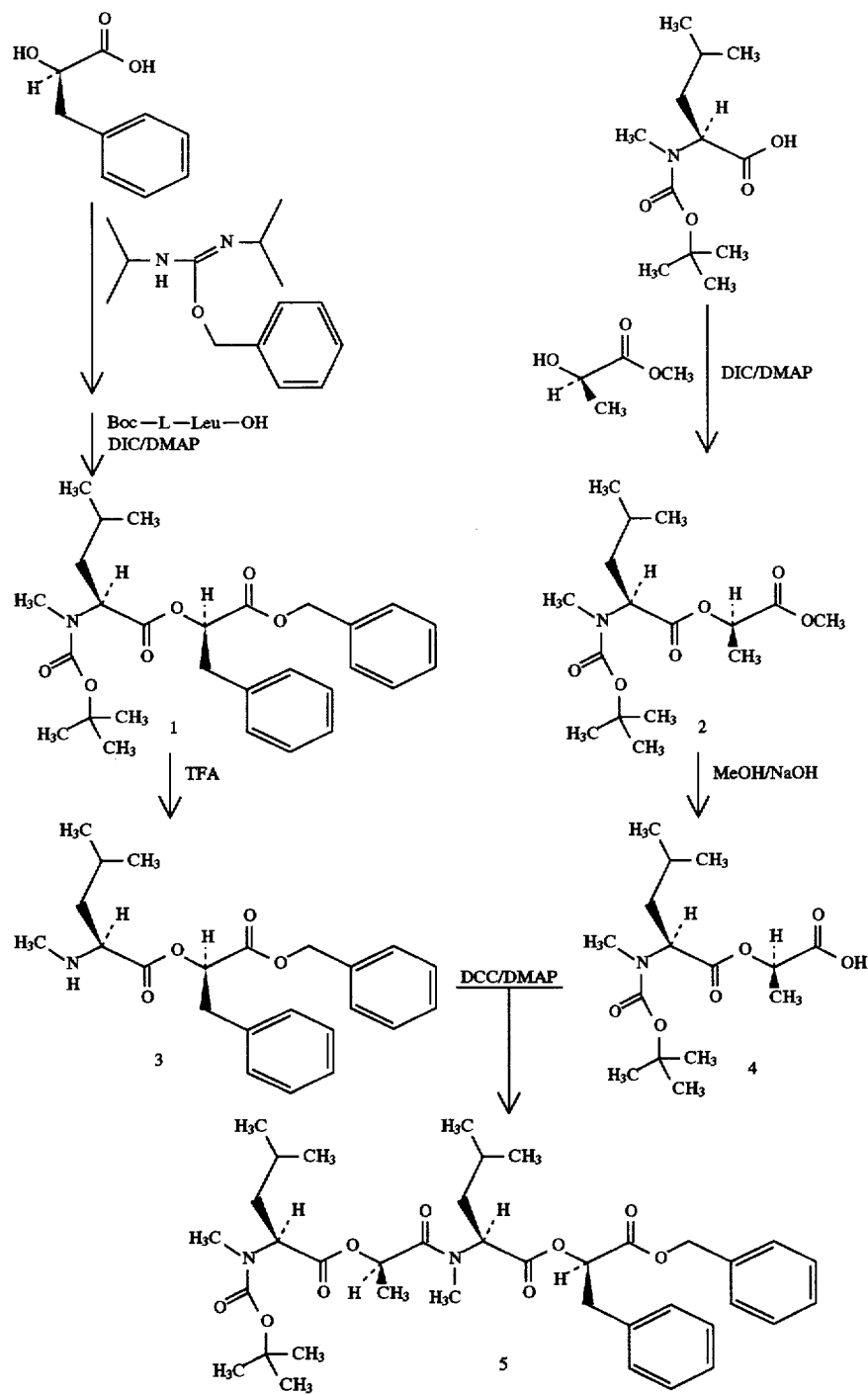

GROUP 1
CHART B
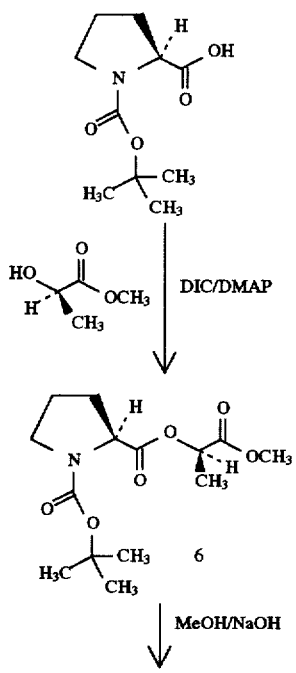
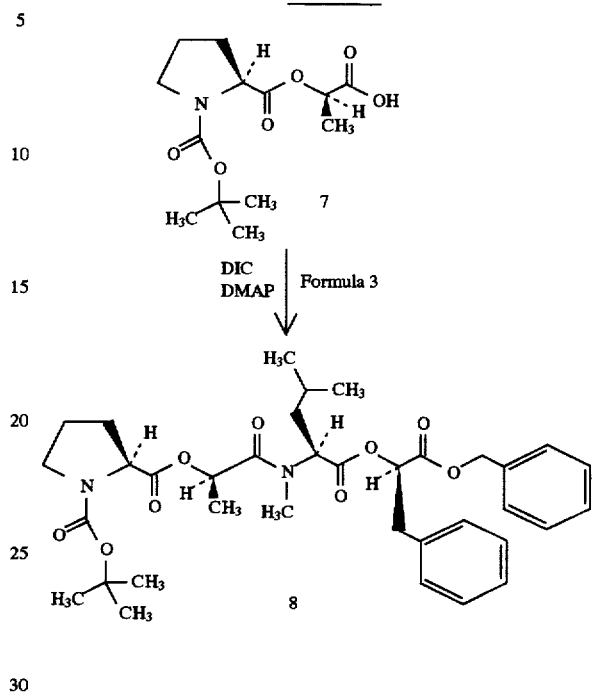
GROUP 1
CHART C
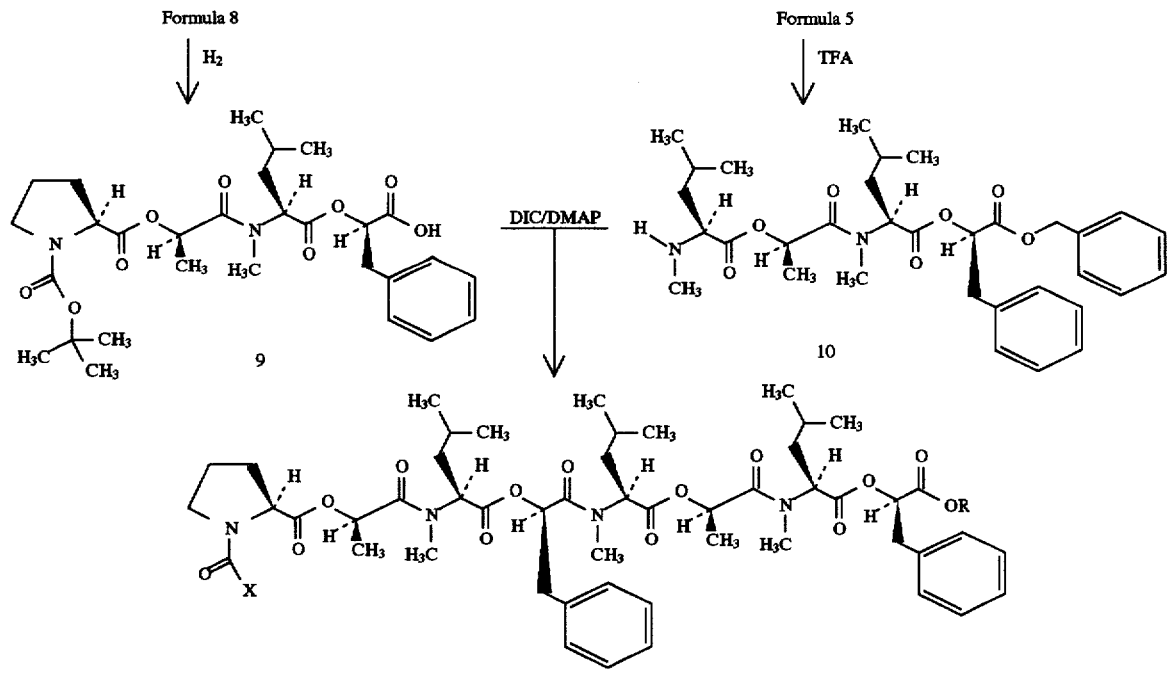

-continued
GROUP 1
CHART C
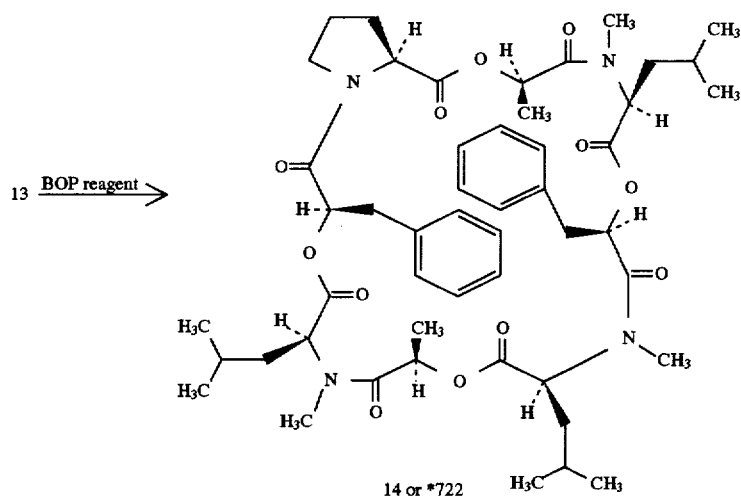
13 →[BOP reagent]→ 14 or *722
GROUP 1
CHART D
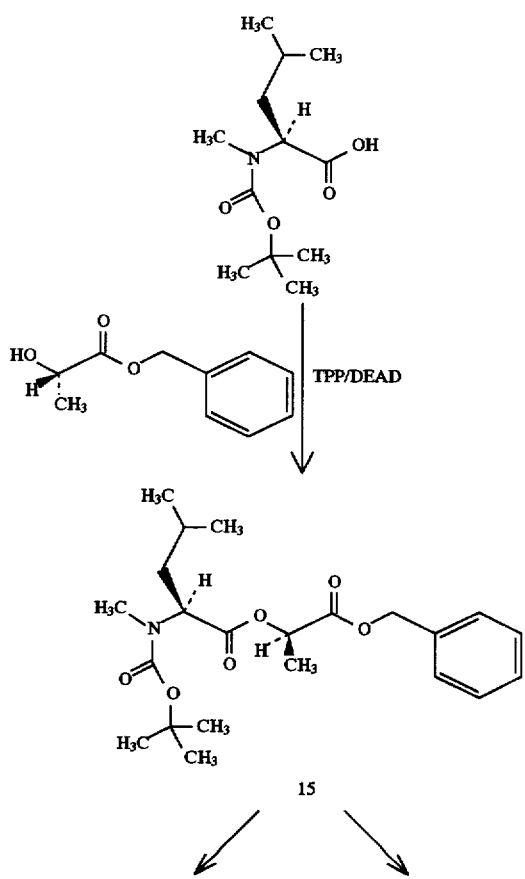
15

-continued
GROUP 1
CHART D
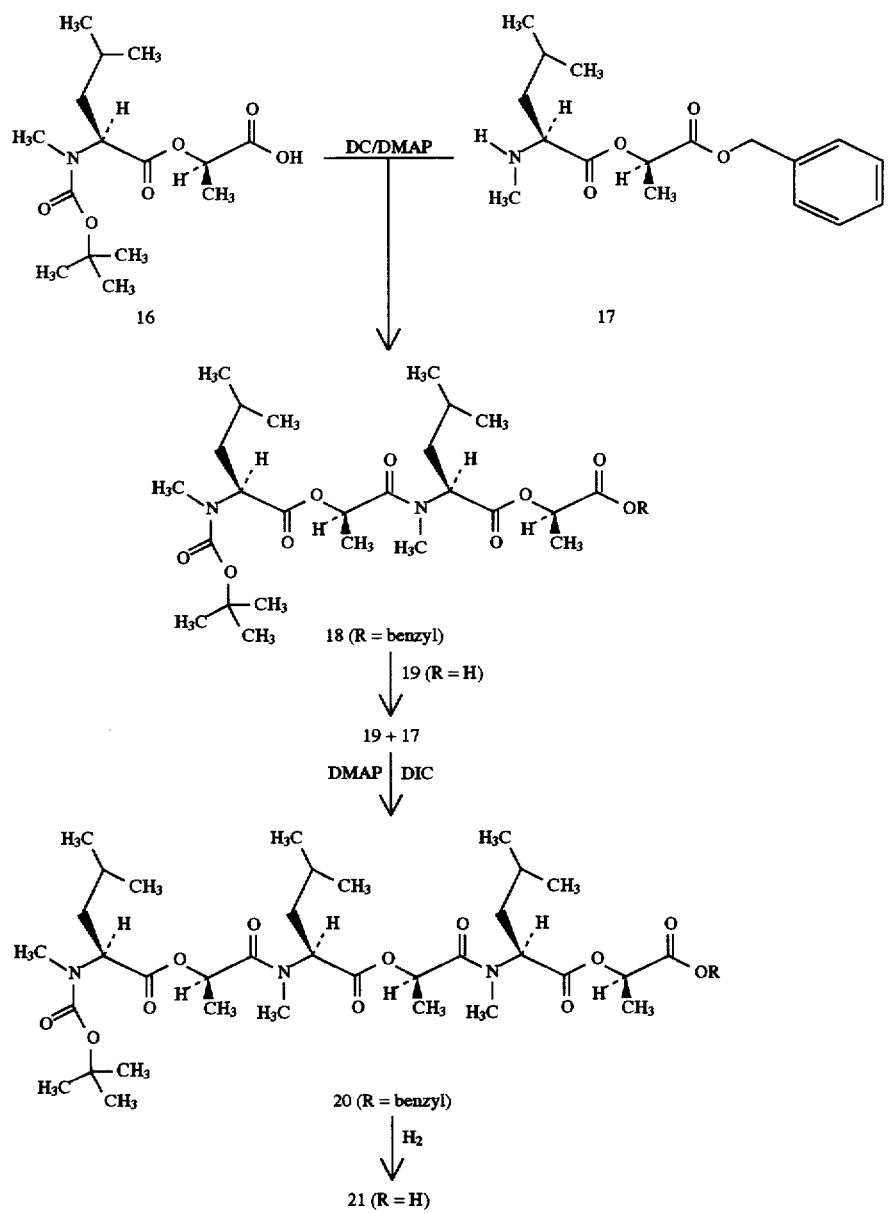

GROUP 1
CHART E
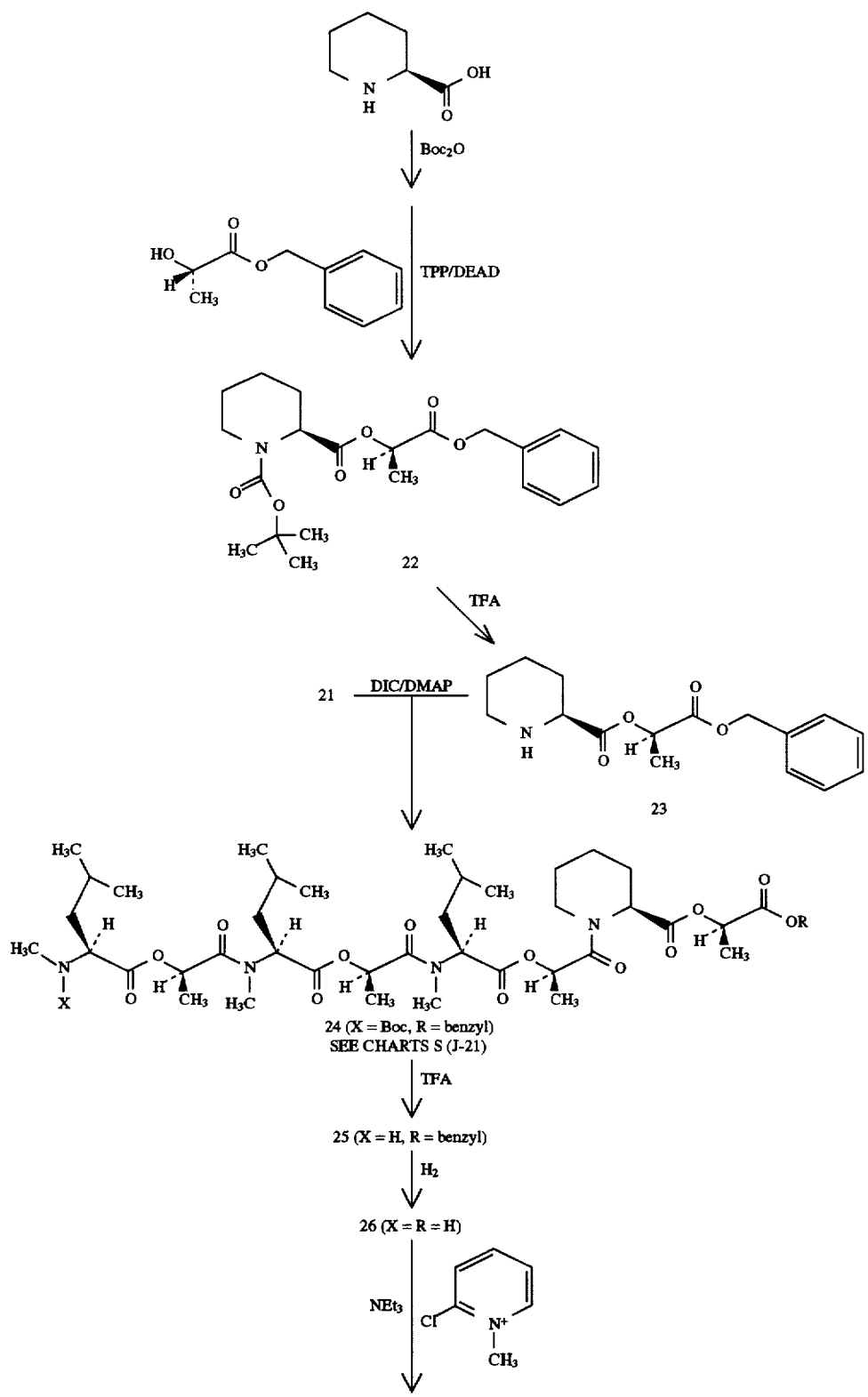

-continued
GROUP 1
CHART E
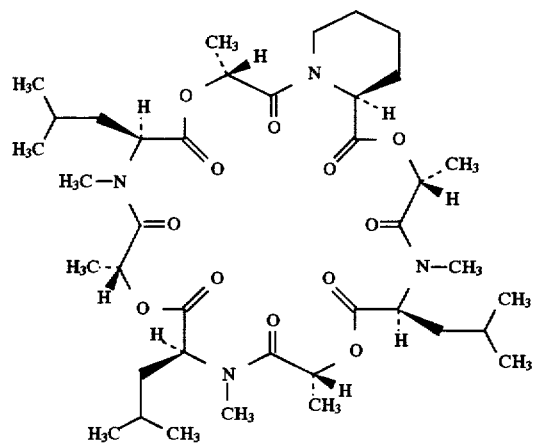
27 or *639
GROUP 1
CHART F
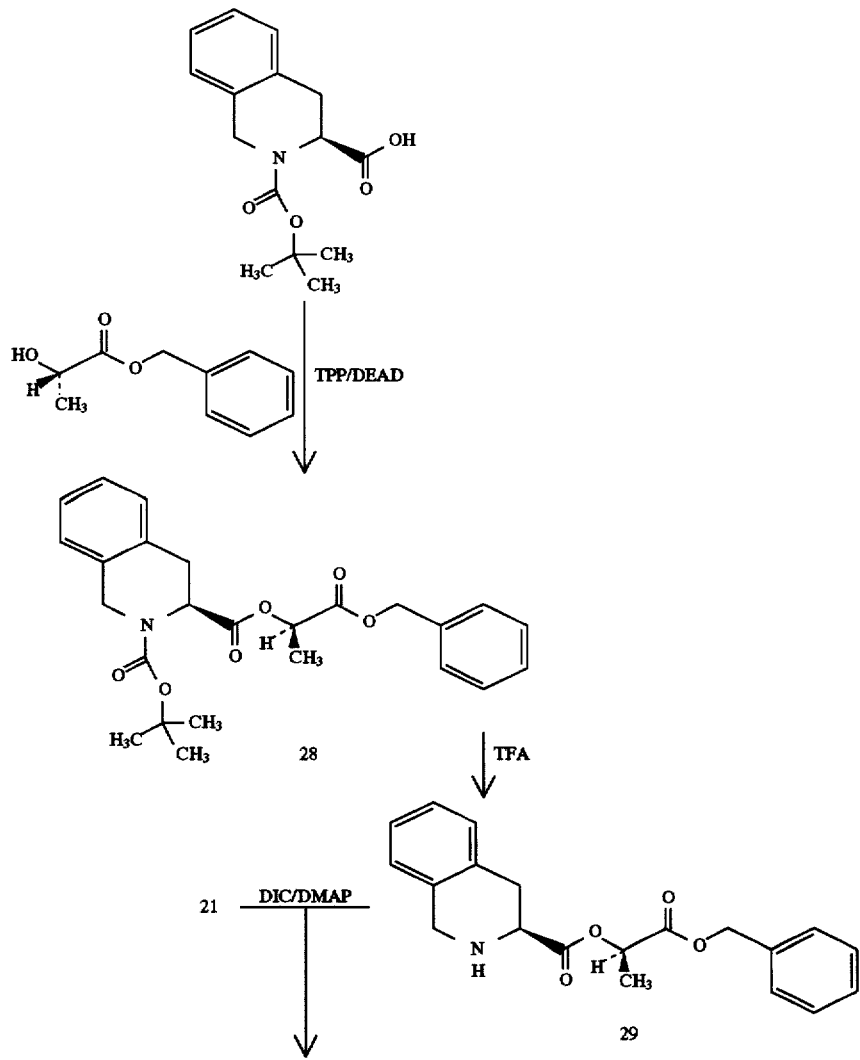

-continued
GROUP 1
CHART F
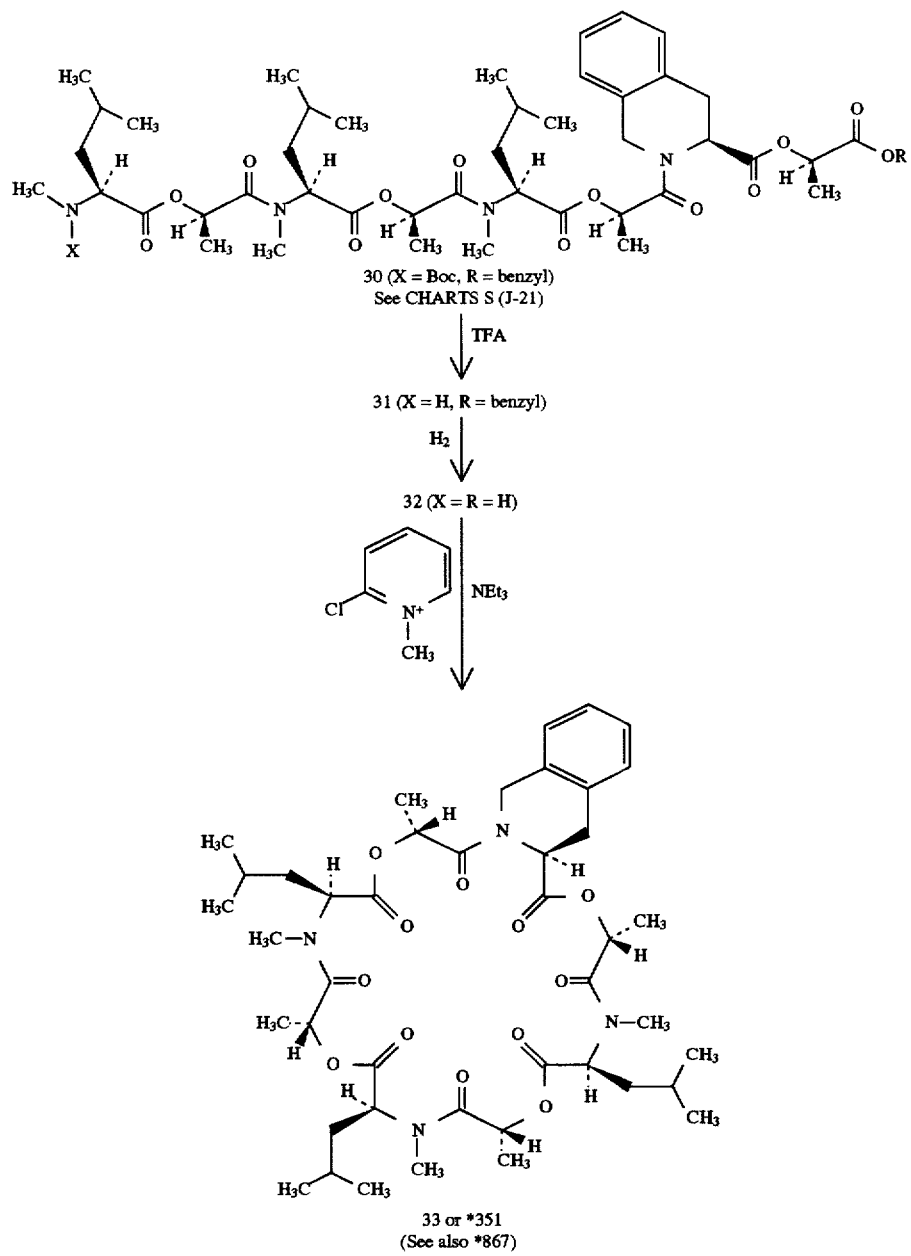

GROUP 1
CHART G
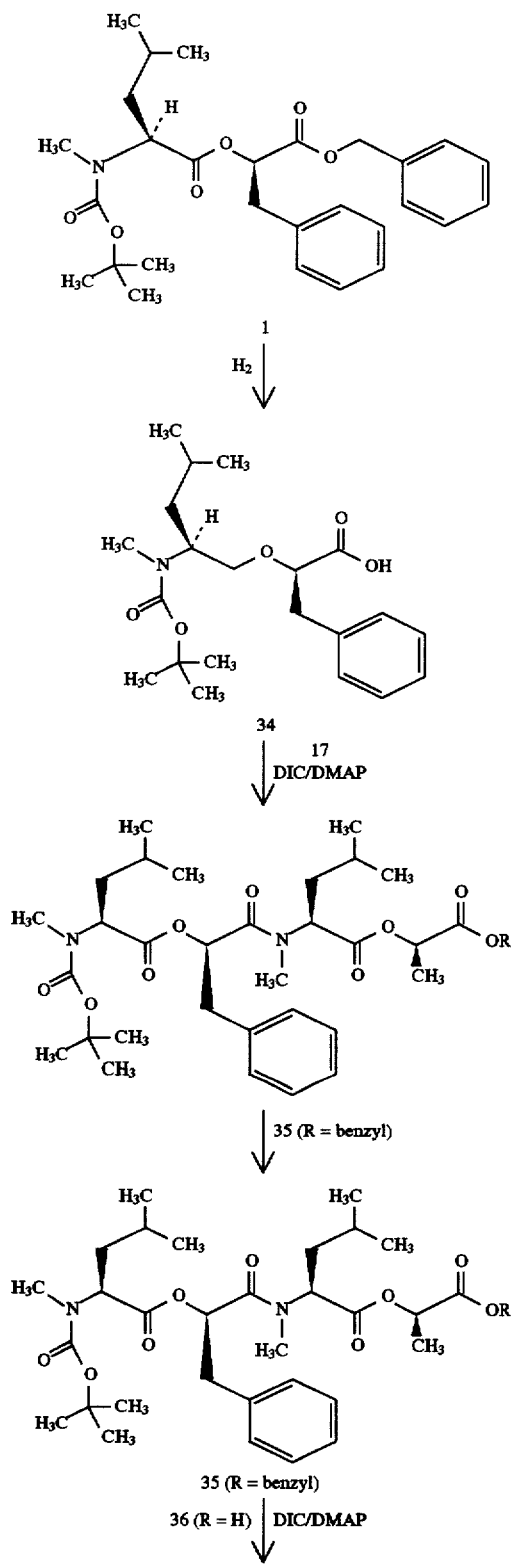

-continued
GROUP 1
CHART G
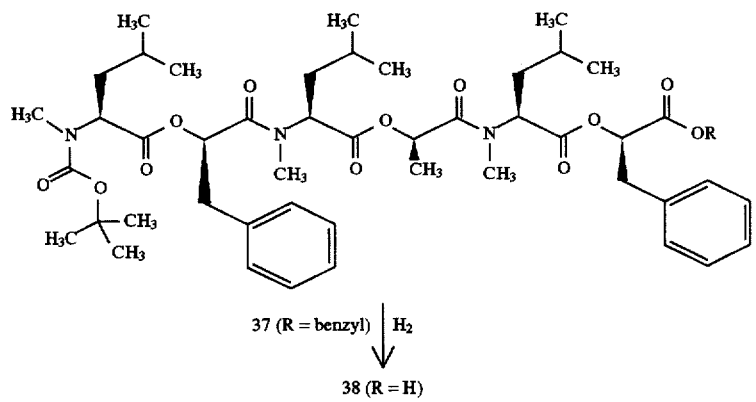
37 (R = benzyl) | H₂
↓
38 (R = H)
GROUP 1
CHART H
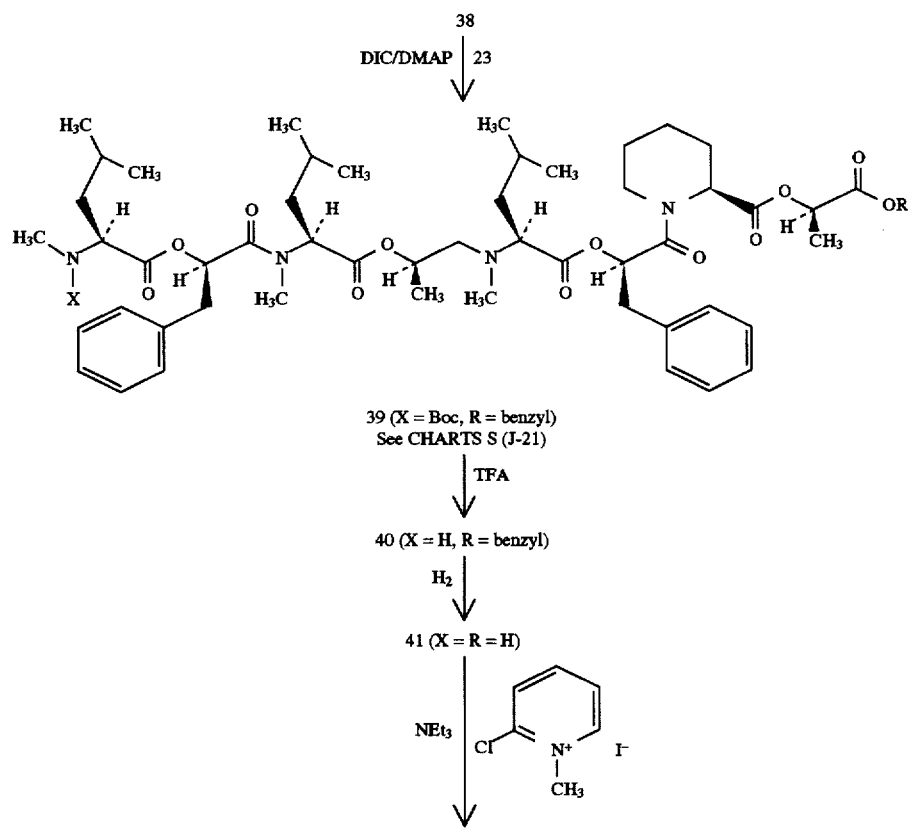

-continued
GROUP 1
CHART H
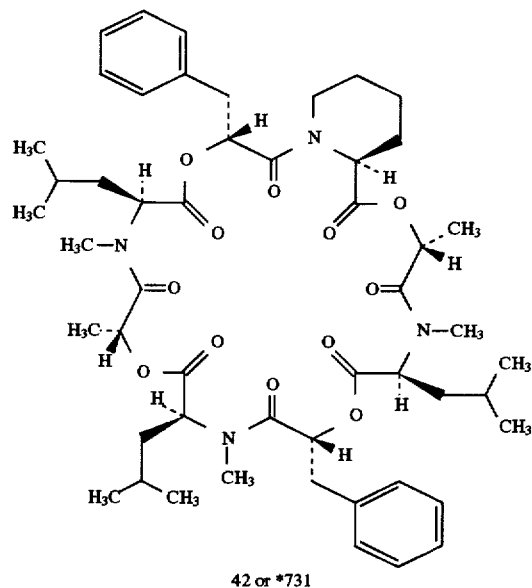
42 or *731
GROUP 1
CHART I
38
DIC/DMAP ↓ 29
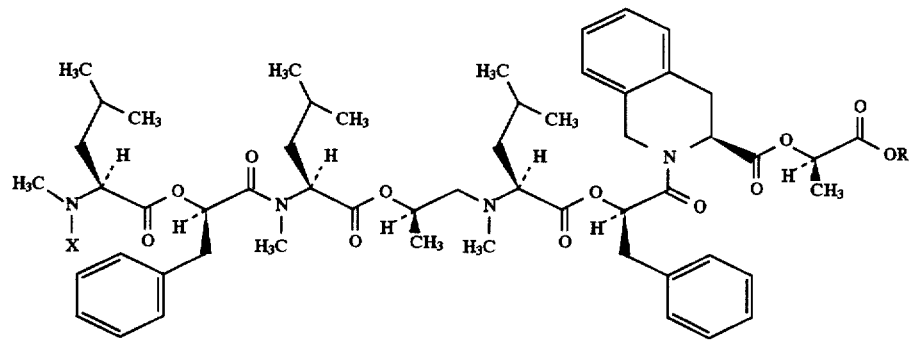
43 (X = Boc, R = benzyl)
See CHARTS S (J-21)
↓ TFA
44 (X = H, R = benzyl)
↓ H₂
45 (X = R = H)
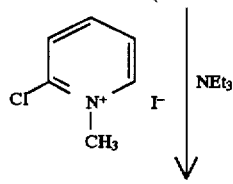
↓ NEt₃

-continued
GROUP 1
CHART I
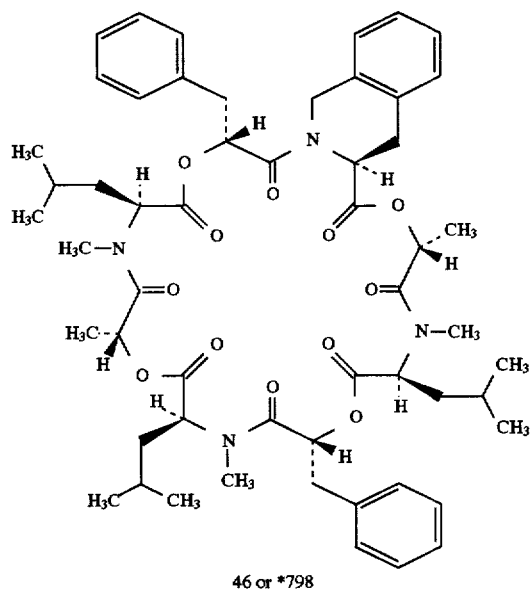
46 or *798
GROUP 2
CHART A
Scheme I
GROUP 2
CHART A
Scheme I
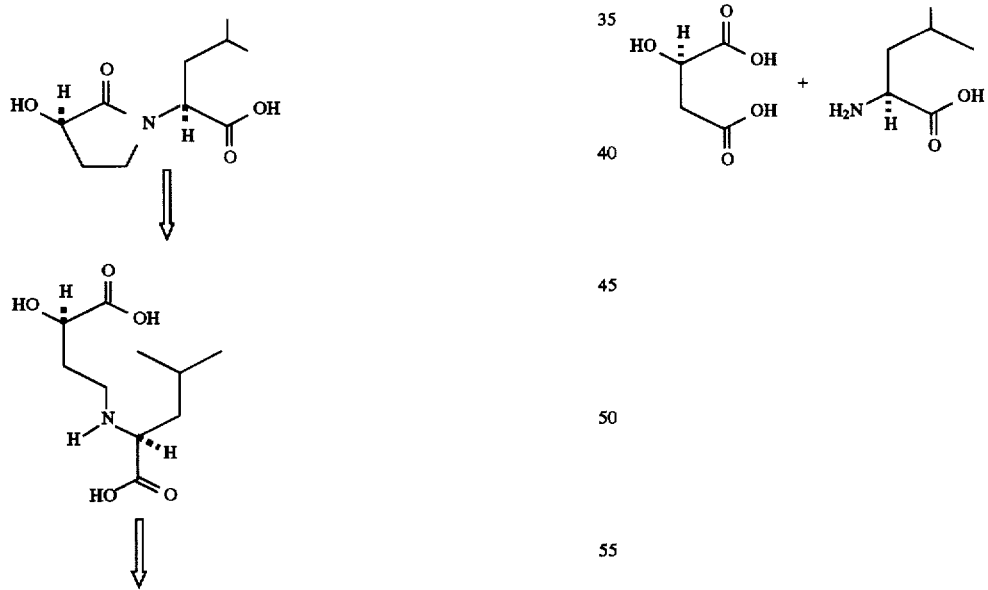

GROUP 2
CHART A, p. 2
Scheme II
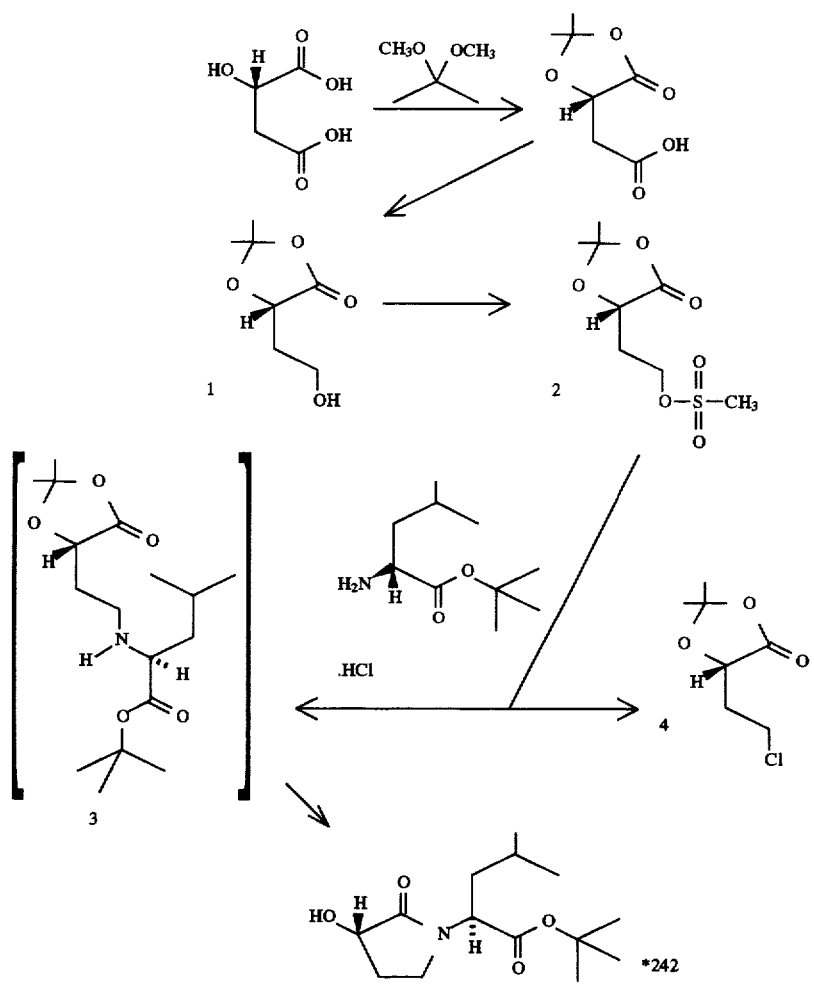
GROUP 2
CHART B
Scheme III
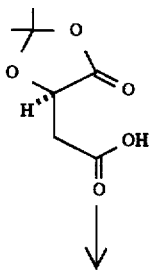

-continued
GROUP 2
CHART B
Scheme III
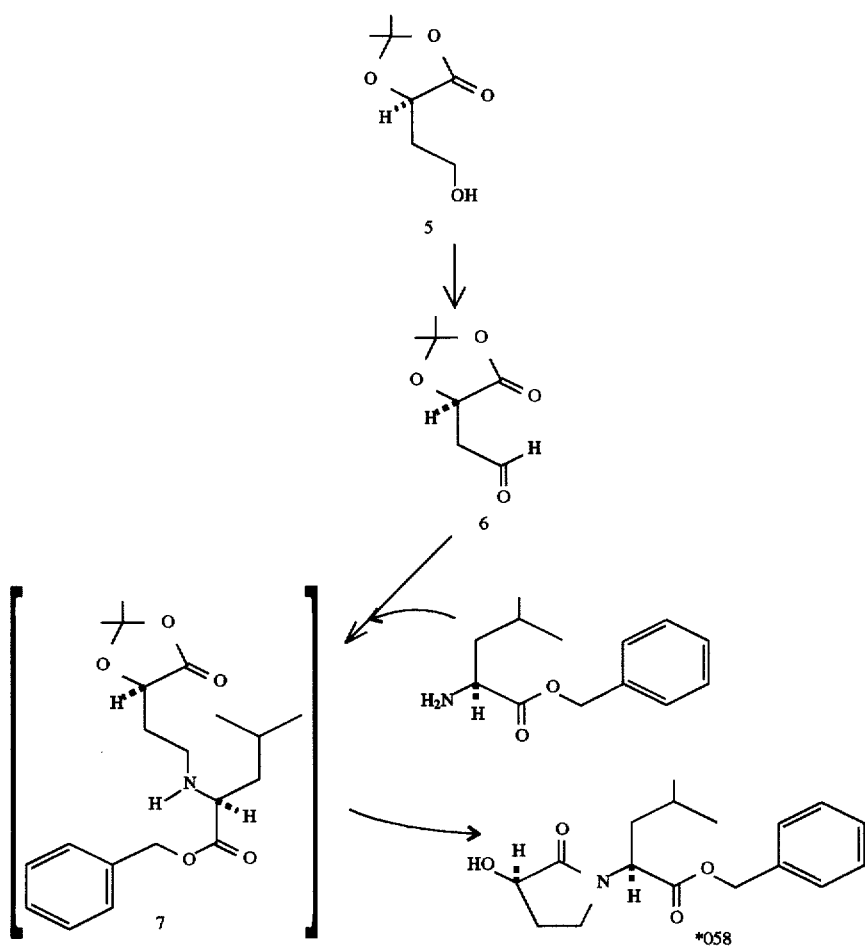
GROUP 2
CHART C
Scheme IV
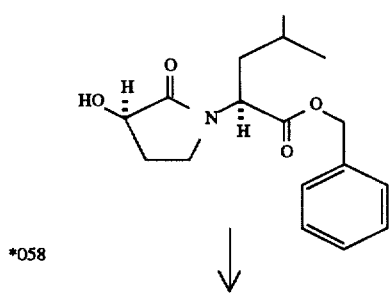

-continued
GROUP 2
CHART C
Scheme IV
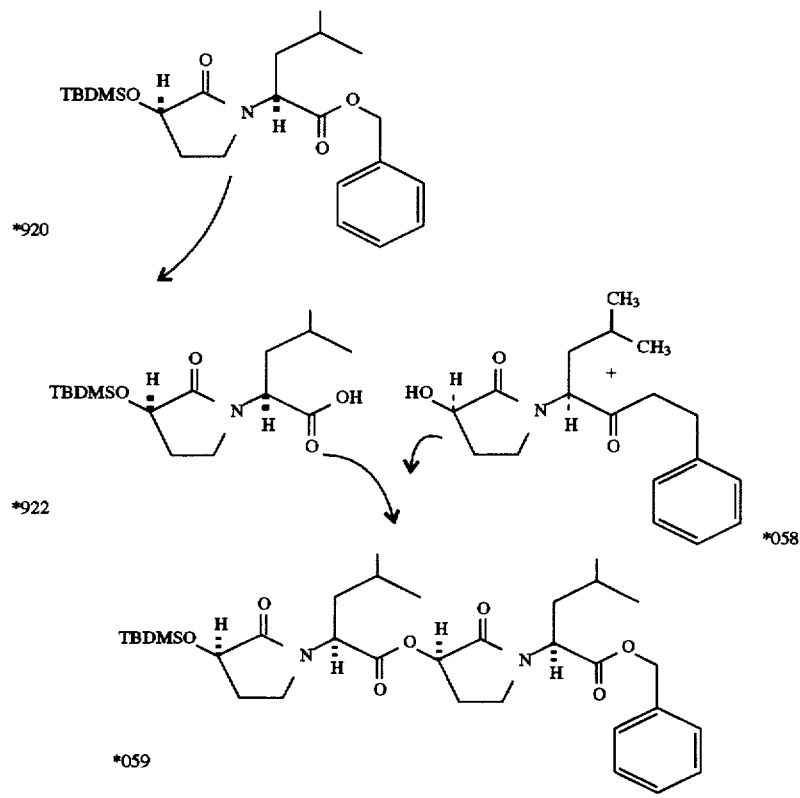
GROUP 2
CHART D
Scheme V
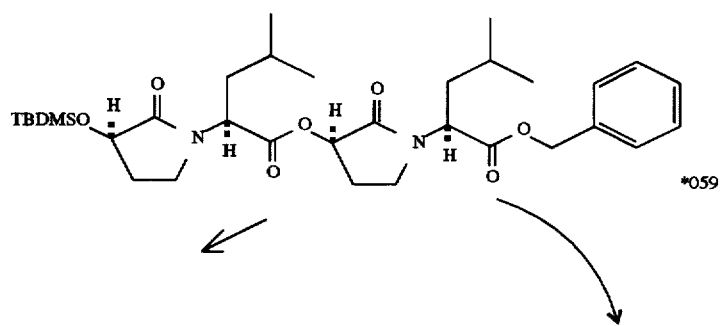

-continued
GROUP 2
CHART D
Scheme V
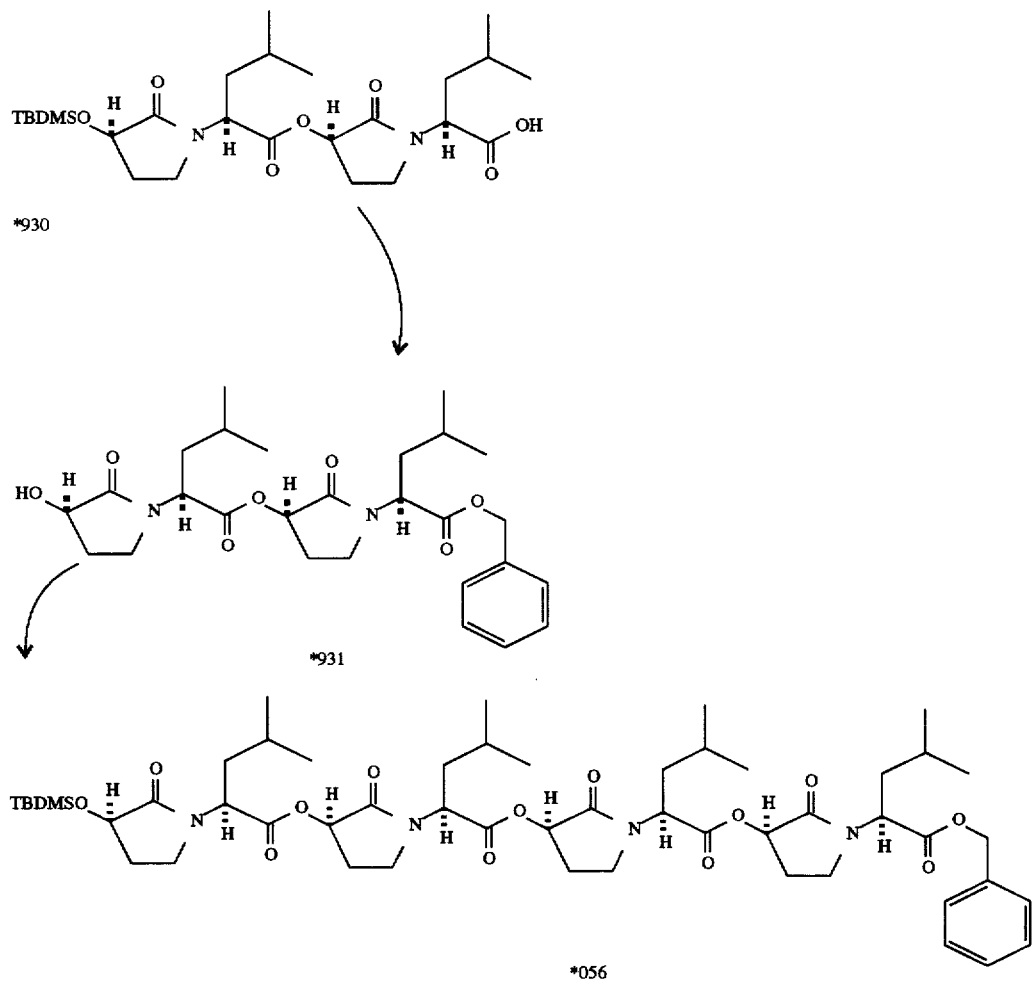
GROUP 2
CHART F
Scheme VI
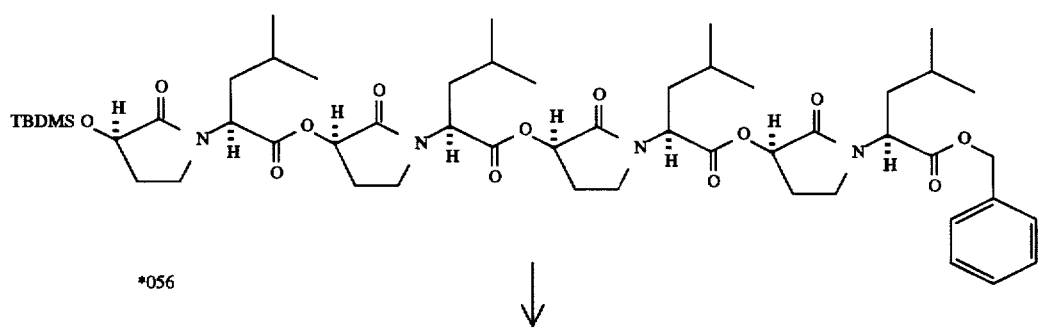

-continued
GROUP 2
CHART F
Scheme VI
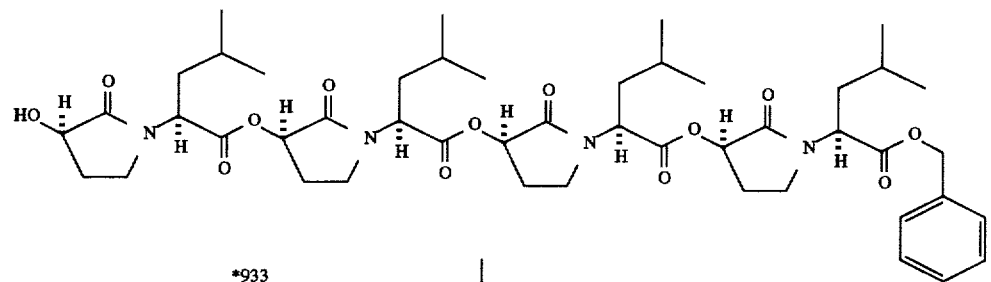
*933
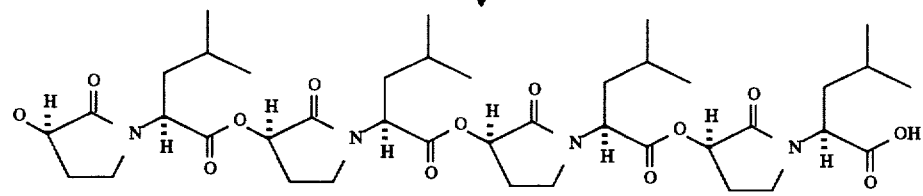
*934
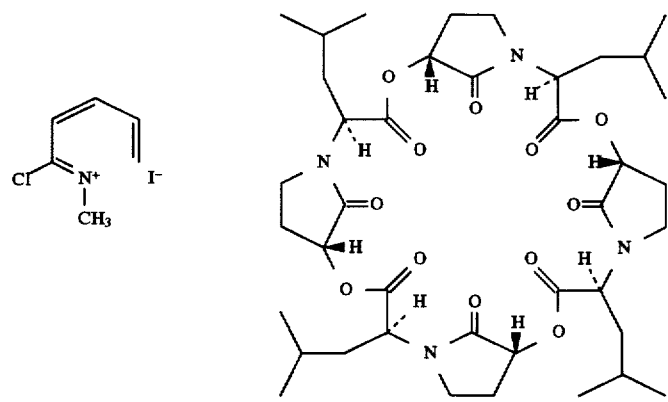
Octadepsipeptide  *101
GROUP 2
CHART G
Scheme VII
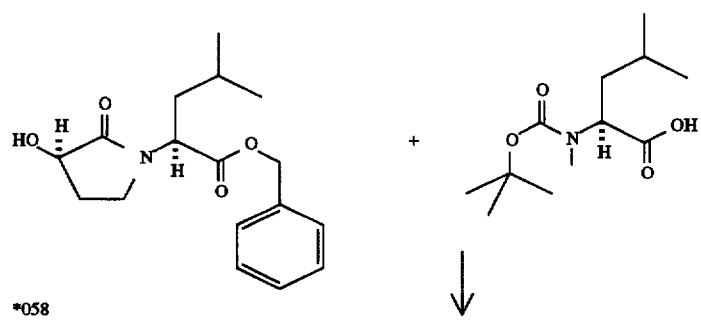
*058

-continued
GROUP 2
CHART G
Scheme VII
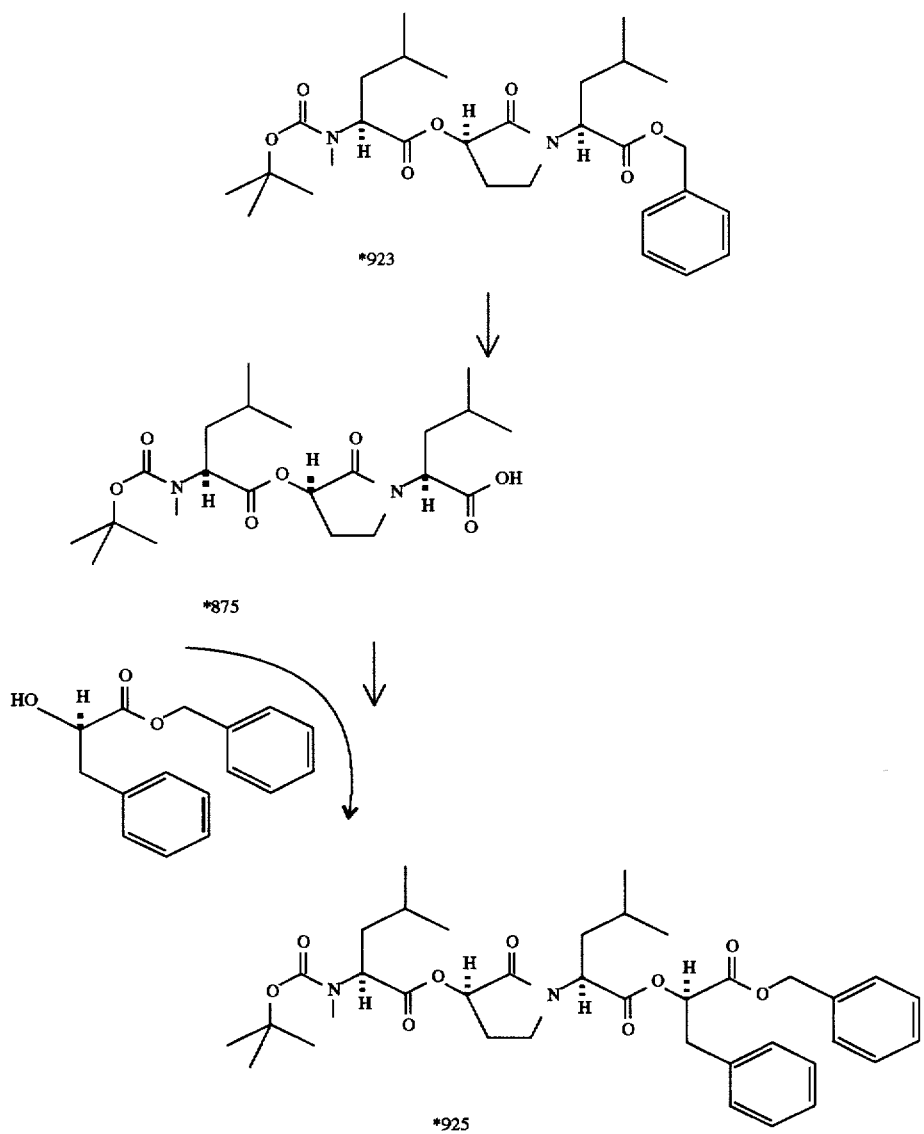

GROUP 2
CHART H
Scheme VIII
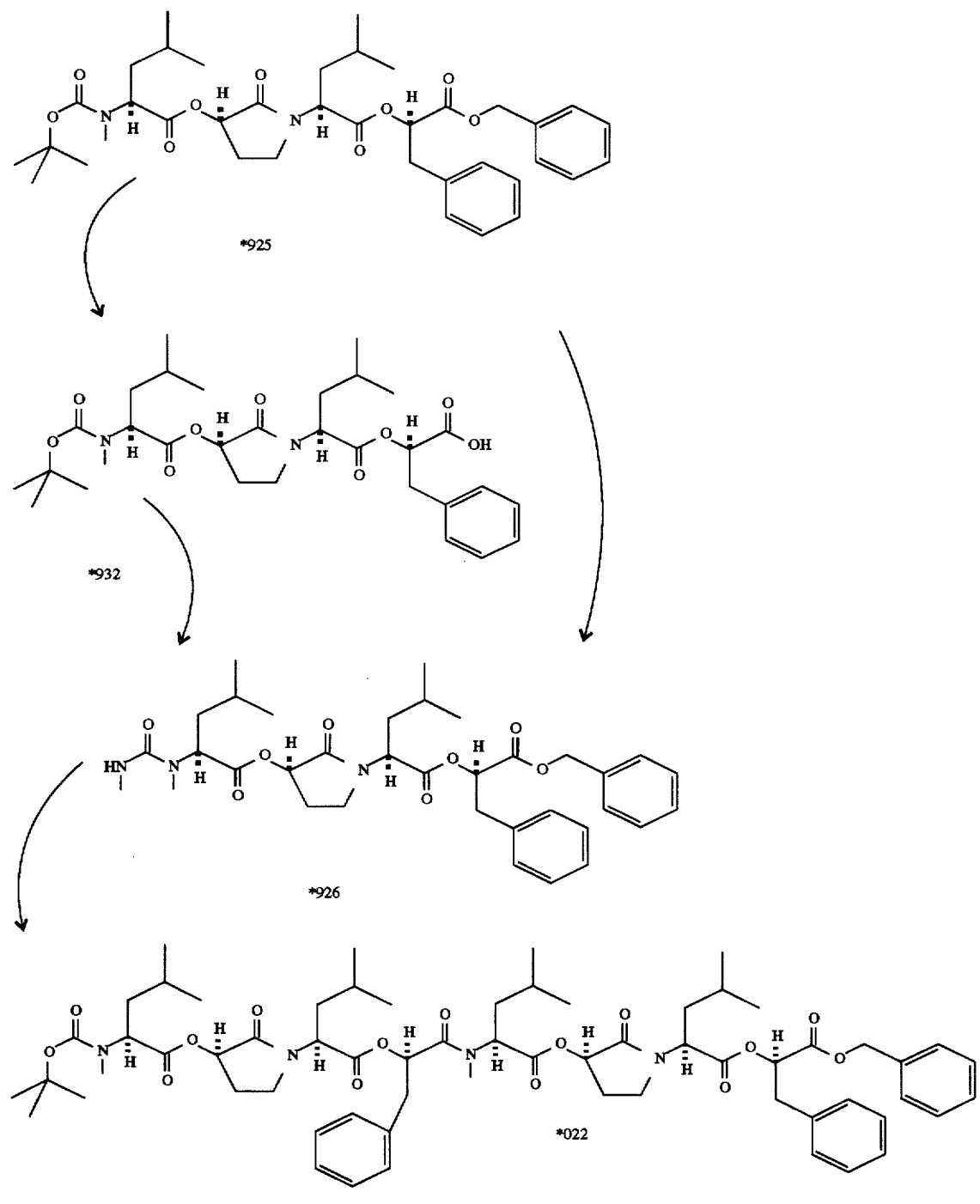
GROUP 2, CHART H, p.2

-continued
GROUP 2
CHART H
Scheme VIII
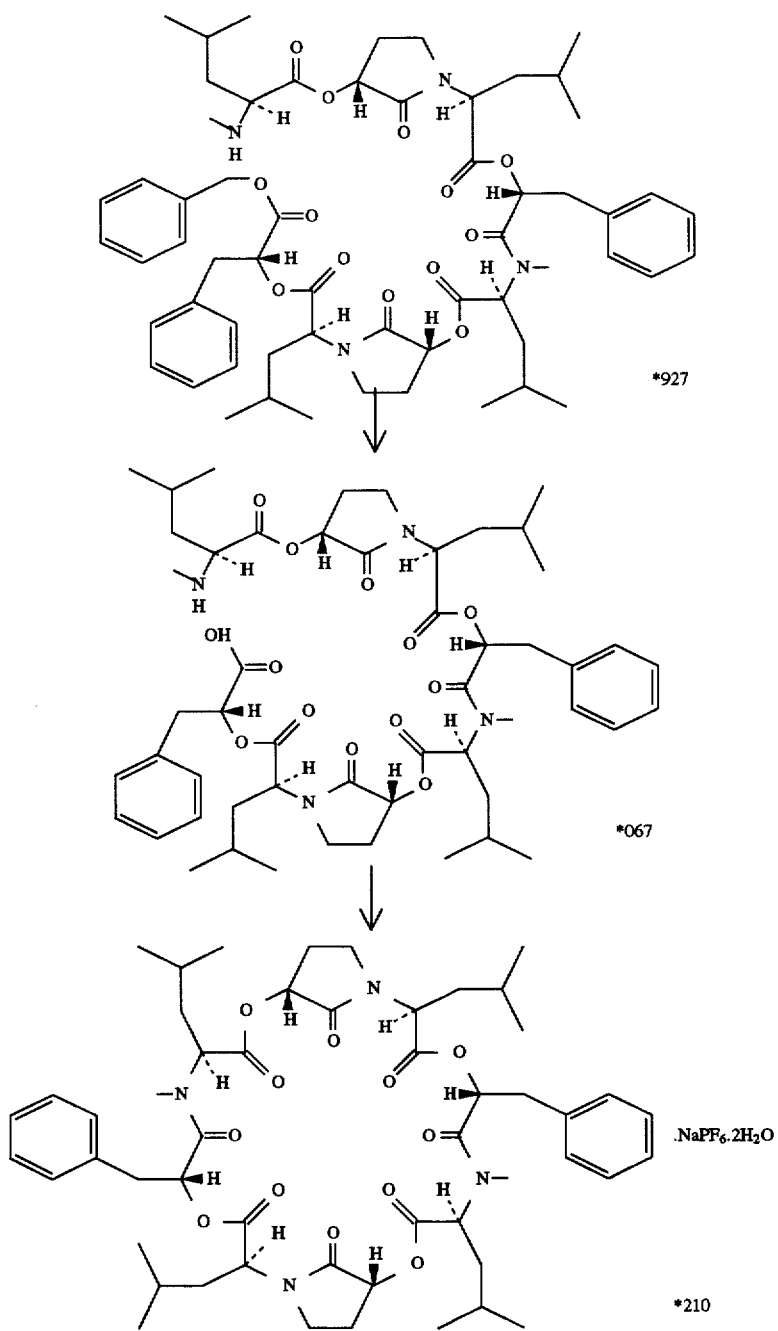

GROUP 2
CHART I
Scheme IX
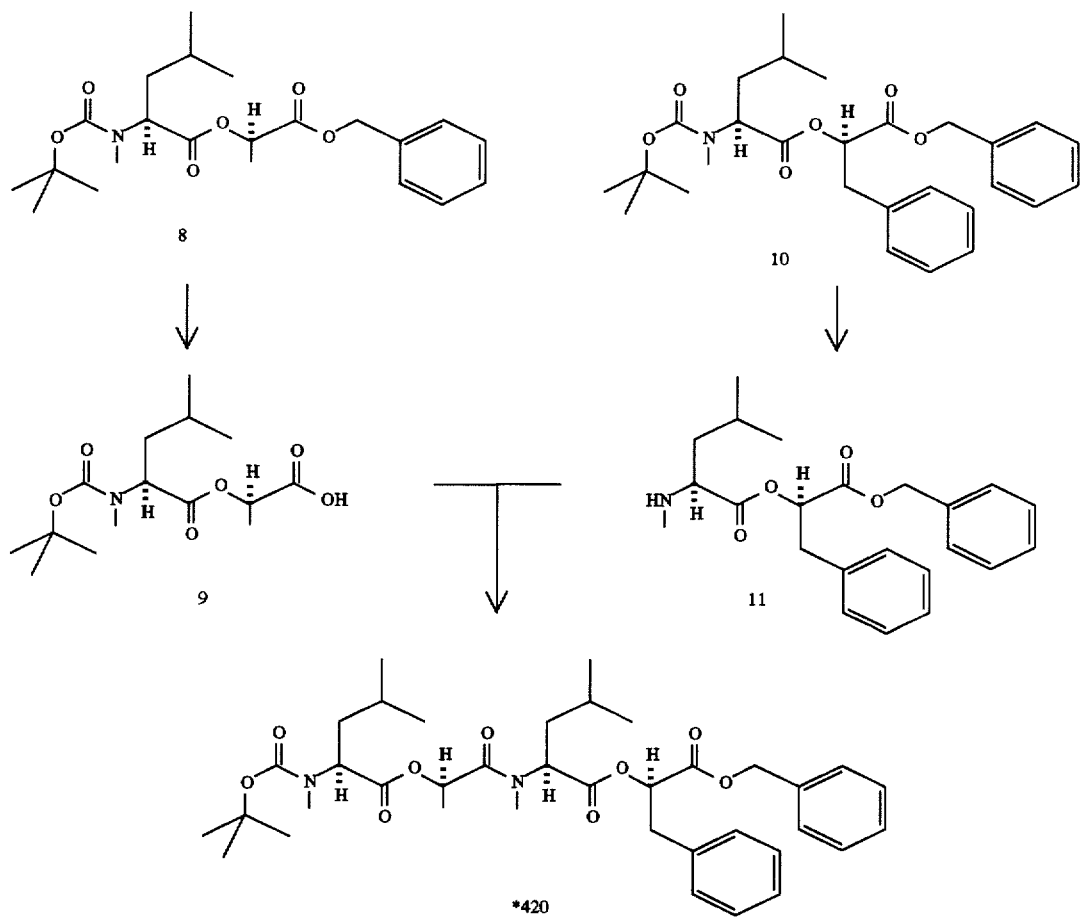
GROUP 2
CHART J
Scheme X
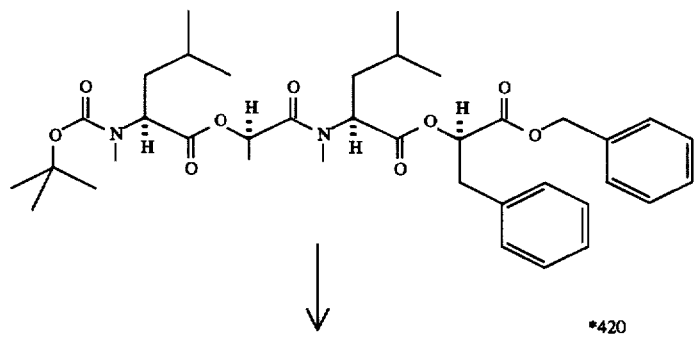

-continued
GROUP 2
CHART J
Scheme X
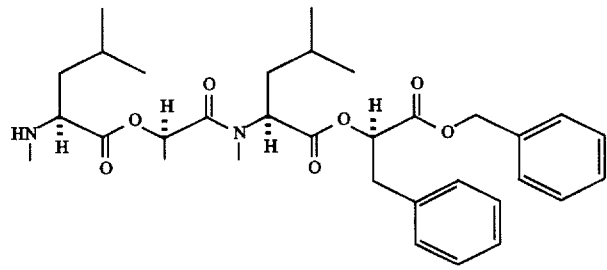
*421
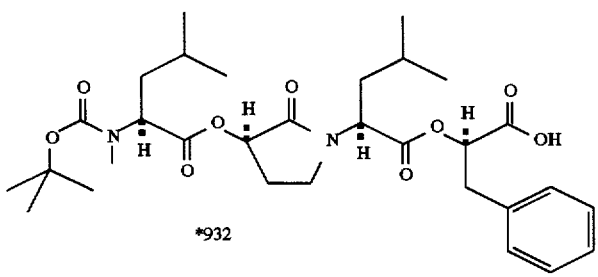
*932
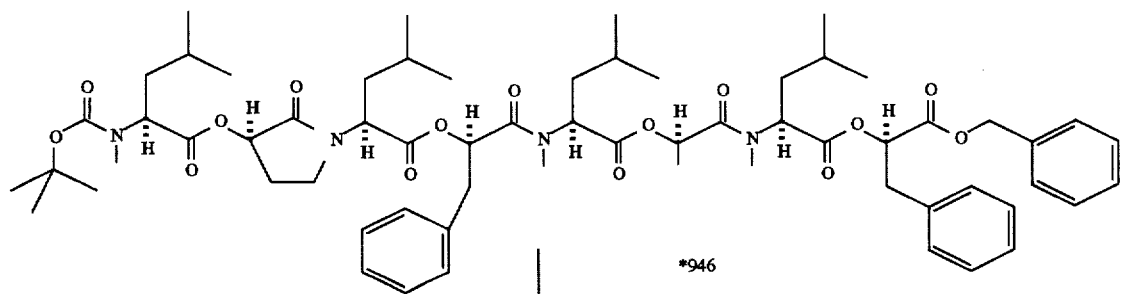
*946
GROUP 2, CHART J, p.2

-continued
GROUP 2
CHART J
Scheme X
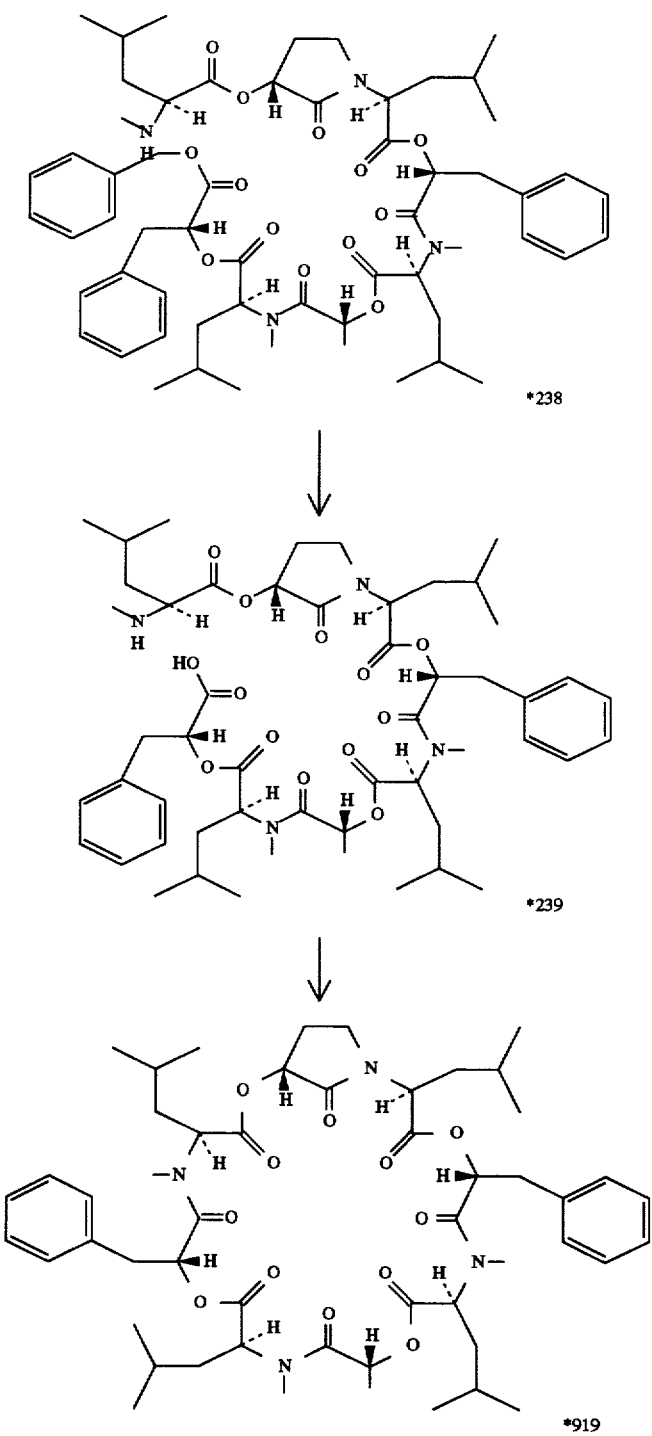

GROUP 3
CHART A
Scheme 1
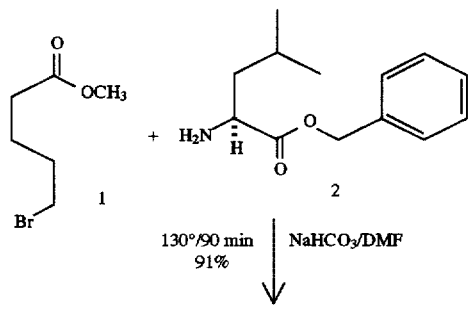
1   +   2
130°/90 min   NaHCO₃/DMF
91%
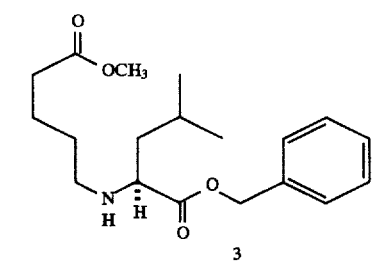
3
Xylene
Reflux
18 hrs
66%
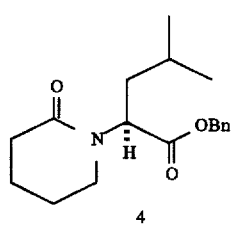
4
TMS—Cl   CH₂Cl₂/–15°
TEA/I₂/Br₂   77%–94%
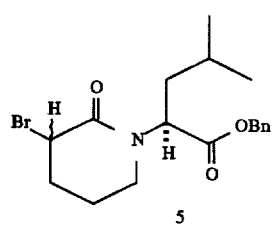
5
H₂O(1 eq.)   Formamide/150°
75%–80%
-continued
GROUP 3
CHART A
Scheme 1
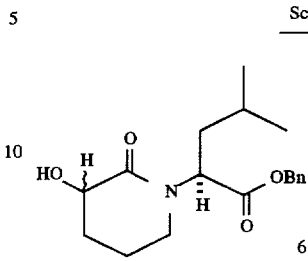
6
1:1 Mixture of
R,S and S,S
70%   Swern oxidation
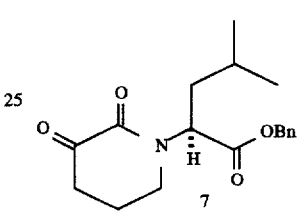
7
D-Glucose   Baker's yeast
59–68%
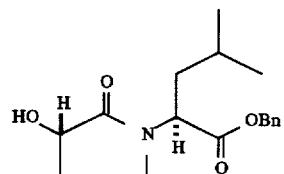
8   70–95% de
DEAD
Ph₃P
76%

115
-continued
GROUP 3
CHART A
Scheme 1
116
-continued
GROUP 3
CHART A
Scheme 1
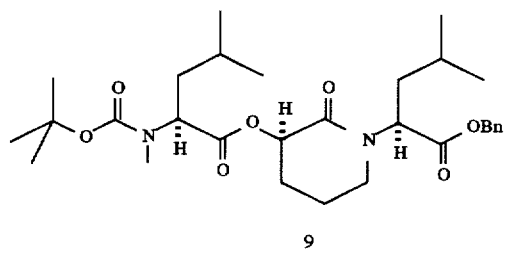
9
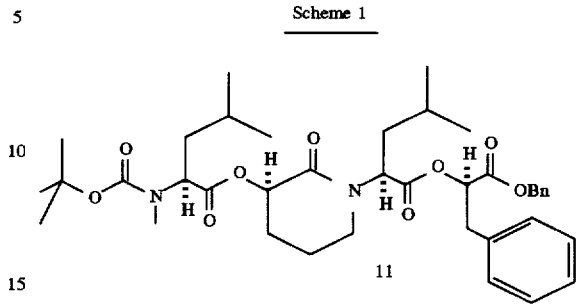
11
H₂/10% Pd/C | 99%
EtOH
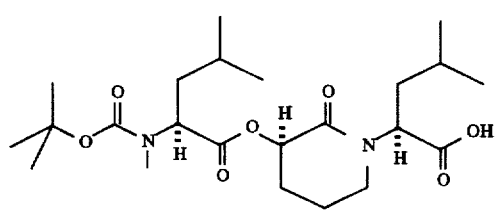
10
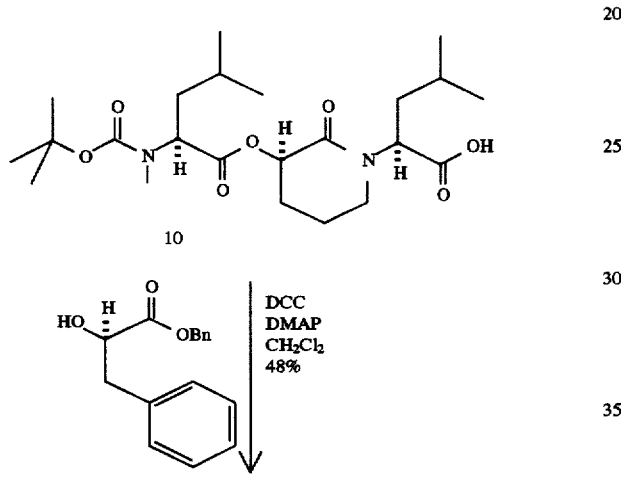
DCC
DMAP
CH₂Cl₂
48%
GROUP 3
CHART A
Scheme 2
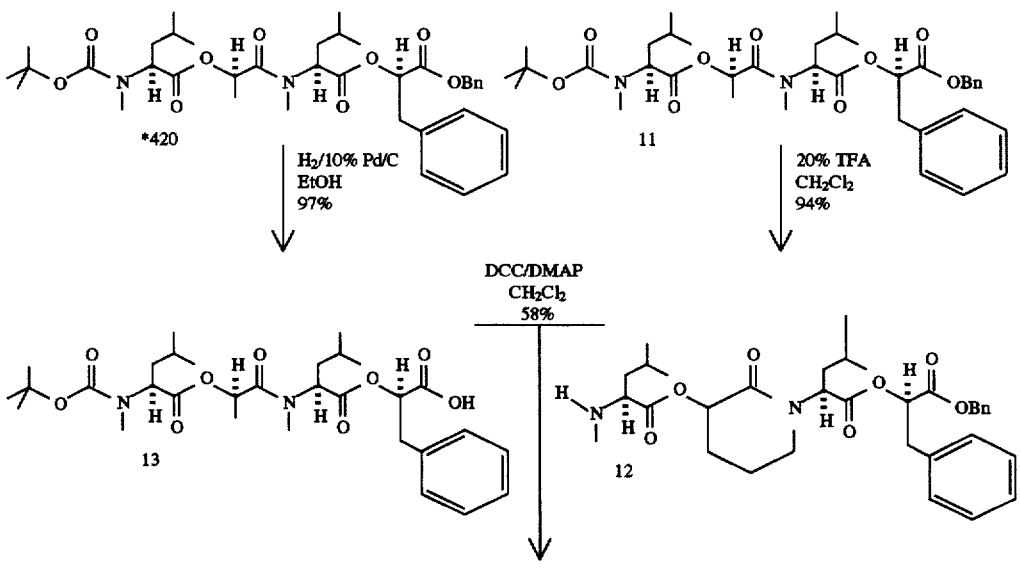

-continued
GROUP 3
CHART A
Scheme 2
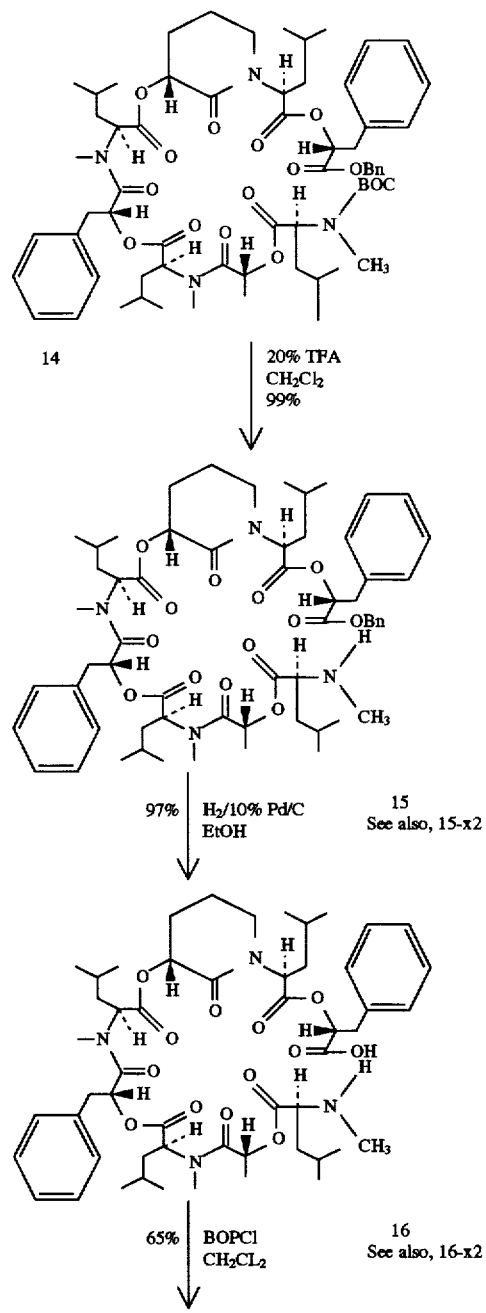

-continued
GROUP 3
CHART A
Scheme 2
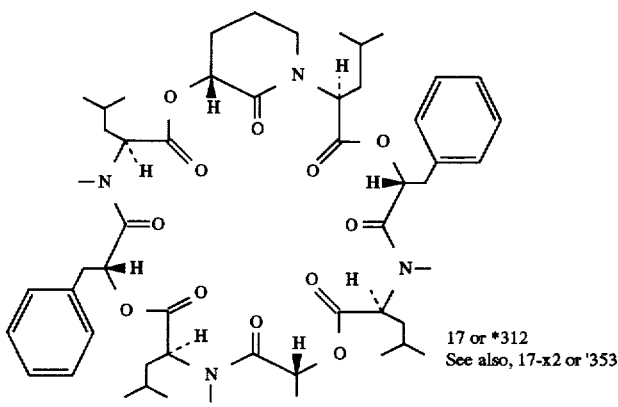
17 or *312
See also, 17-x2 or '353
Table of Compounds
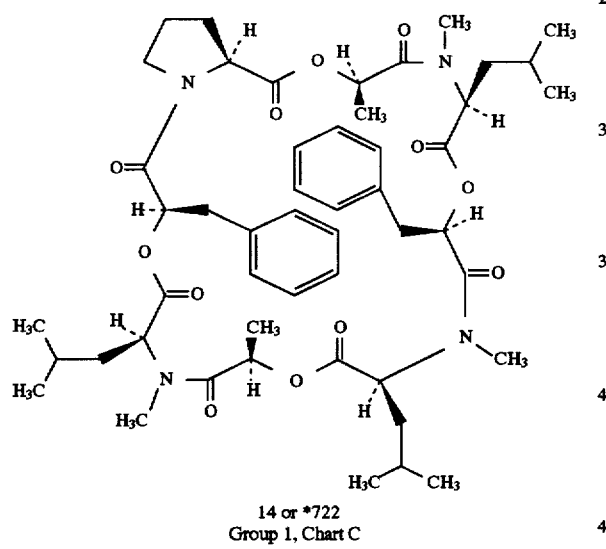
14 or *722
Group 1, Chart C
-continued
Table of Compounds
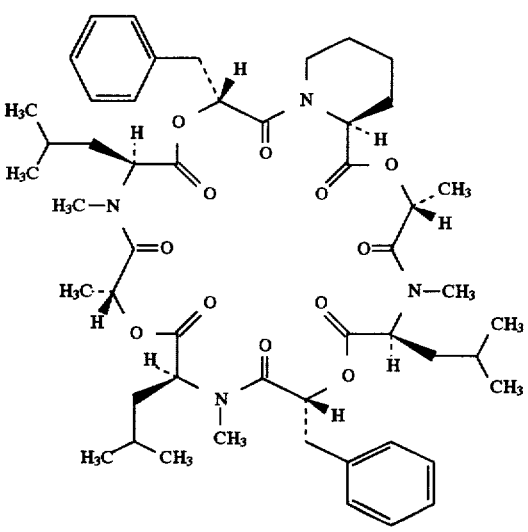
42 or *731
Group 1, Chart H
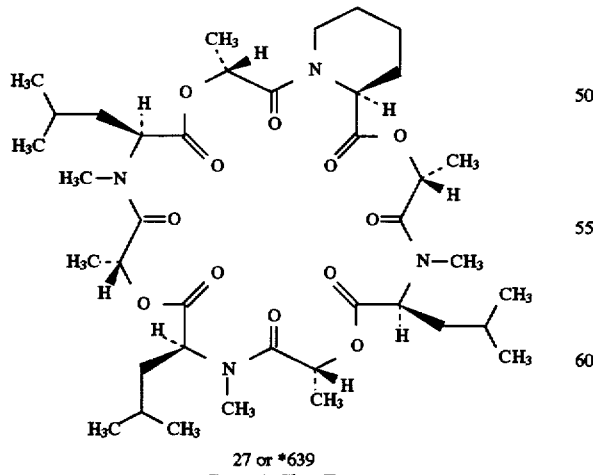
27 or *639
Group 1, Chart E

121
-continued
Table of Compounds
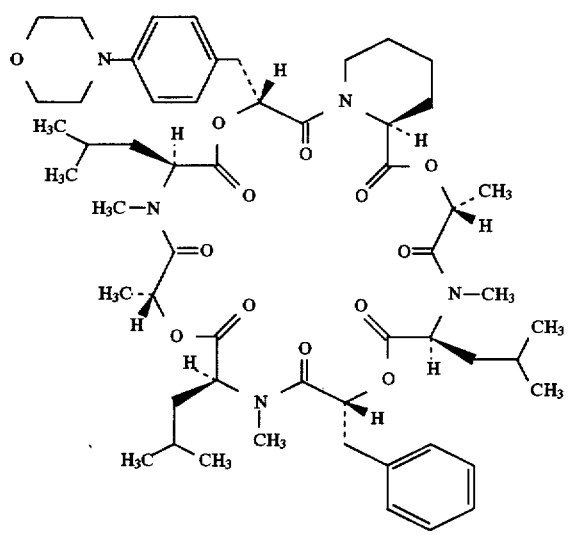
47 or *062
Group 1, Chart H
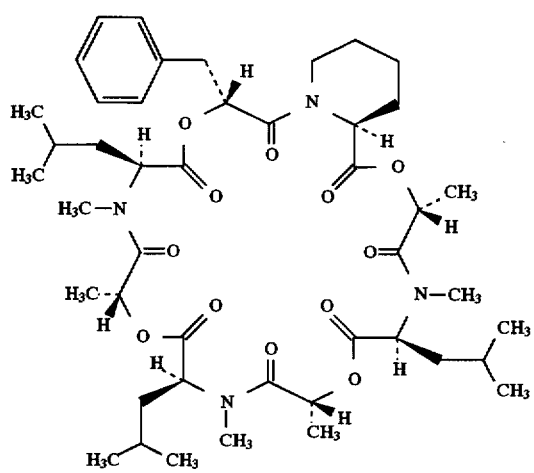
48 or *560
Group 1, Chart H
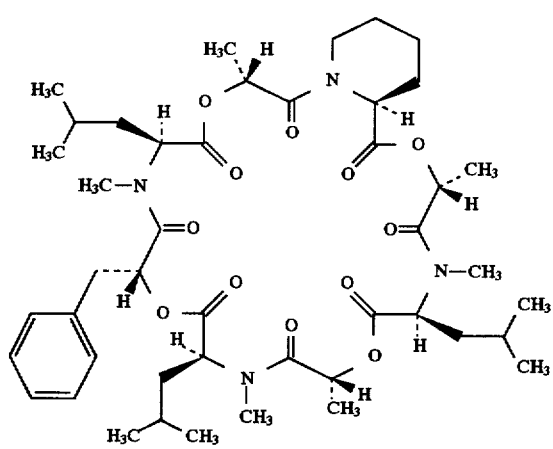
49 or *561
Group 1, Chart H
122
-continued
Table of Compounds
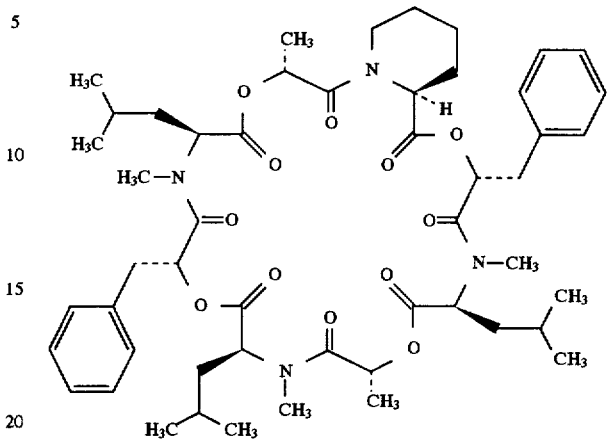
50 or *625
Group 1, Chart H
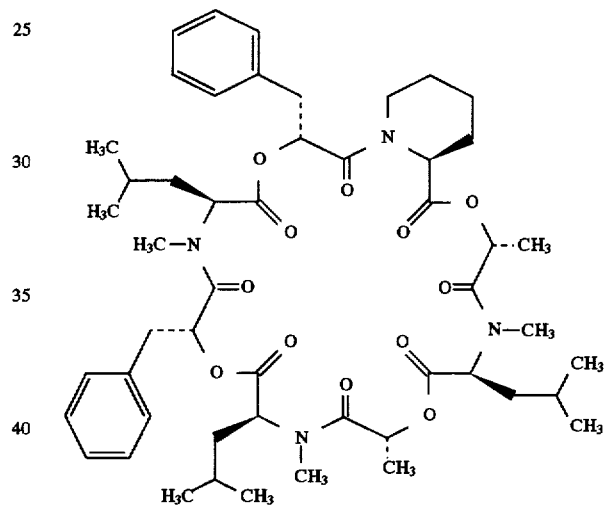
52 or *755
Group 1, Chart H
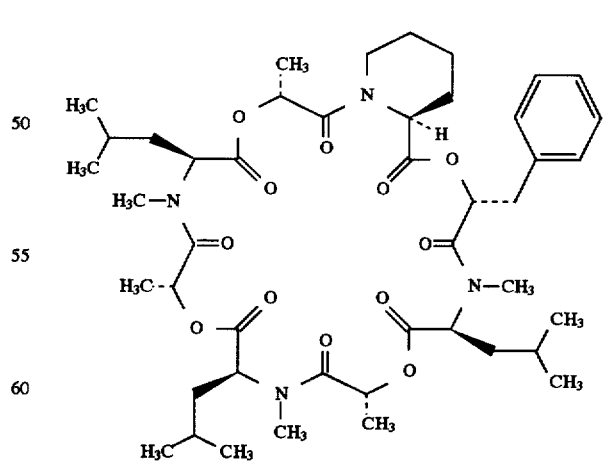
51 or *626
Group 1, Chart H 5,776,950
123
-continued
Table of Compounds
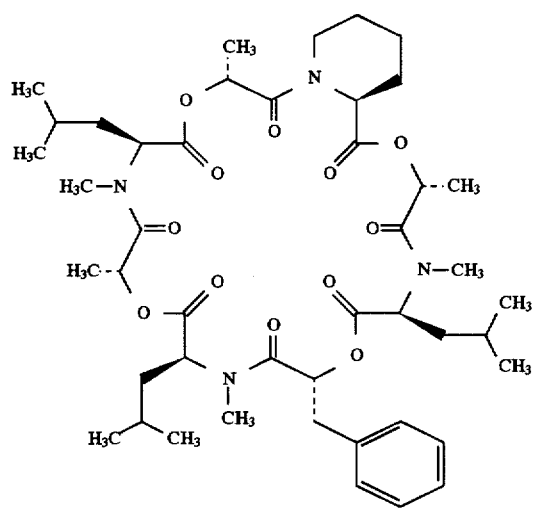
53 or *776
Group 1, Chart H
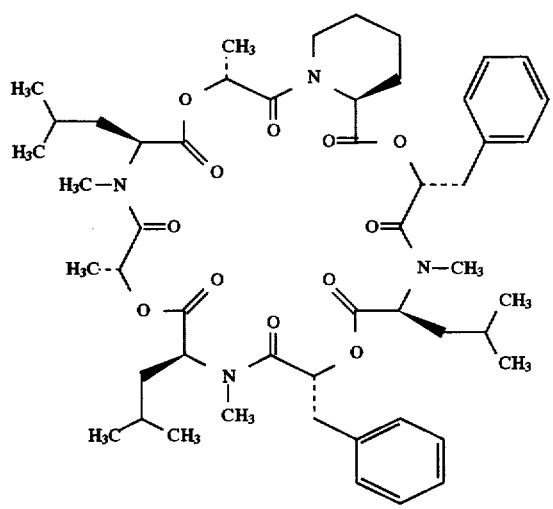
54 or *777
Group 1, Chart H
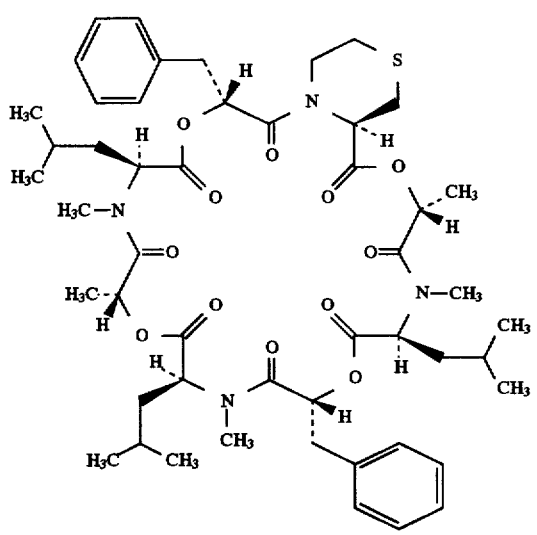
56 or *857
Group 1, Chart H
124
-continued
Table of Compounds
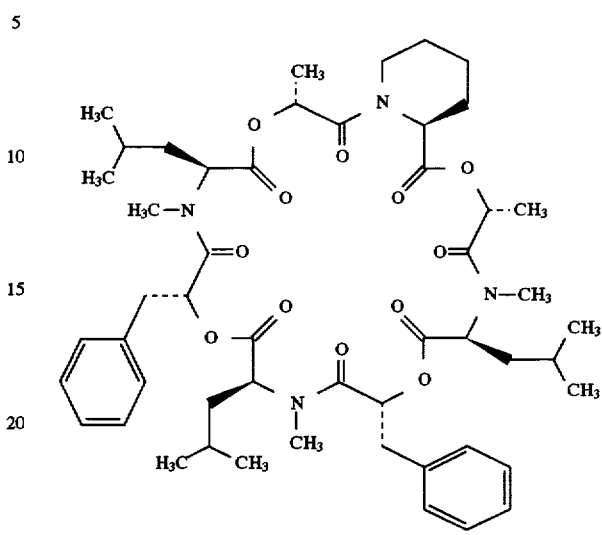
55 or *819
Group 1, Chart H
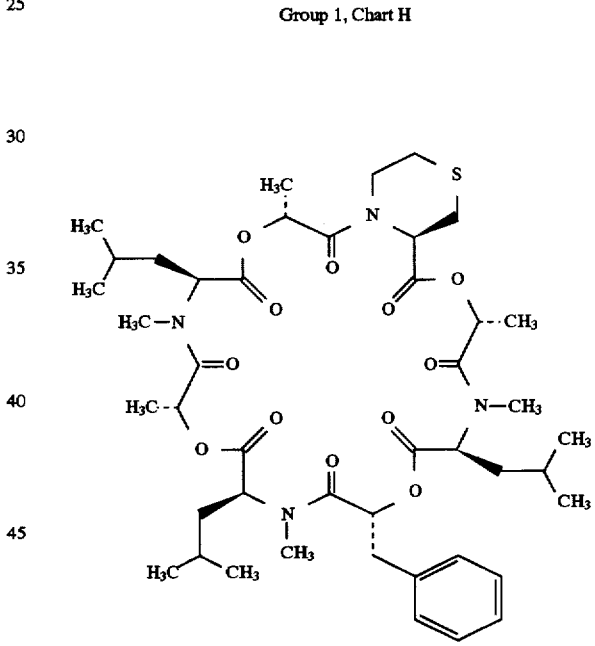
57 or *897
Group 1, Chart H

125
-continued
Table of Compounds
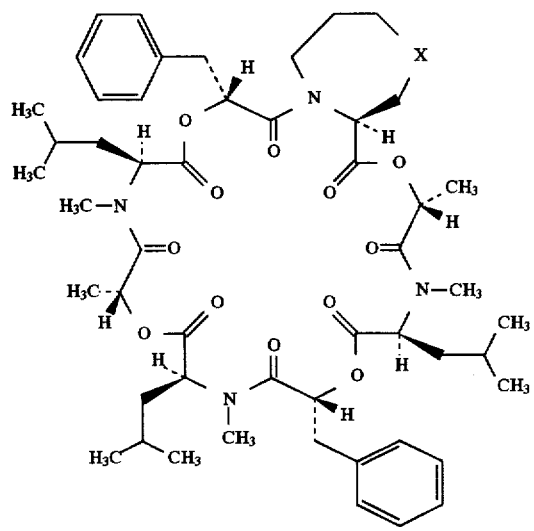
58 or *421 (X = CH₂)
59 (X = S)
Group 1, Chart H
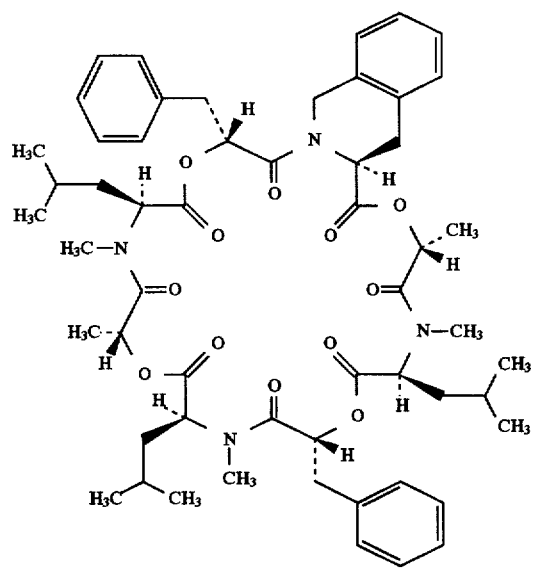
46 or *798
Group 1, Chart I
126
-continued
Table of Compounds
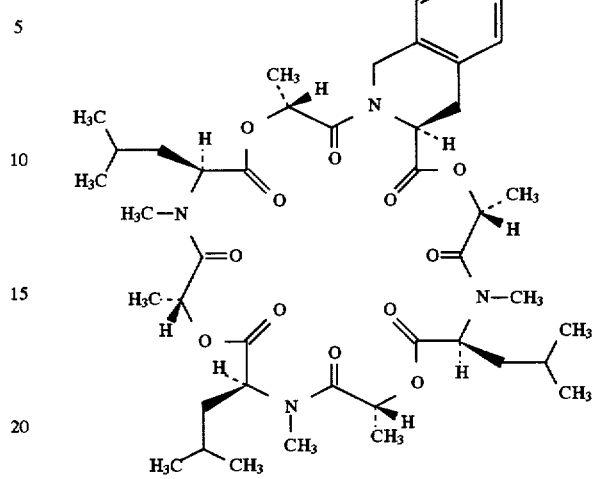
33 or *351
Group 1, Chart F
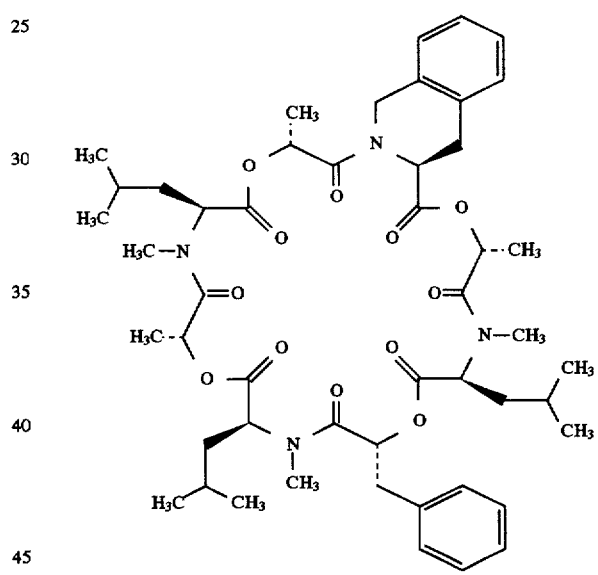
*867
Group 1, Chart F
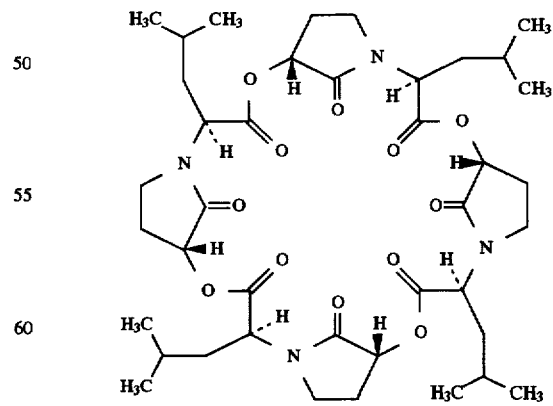
*101
GROUP 2

-continued
Table of Compounds

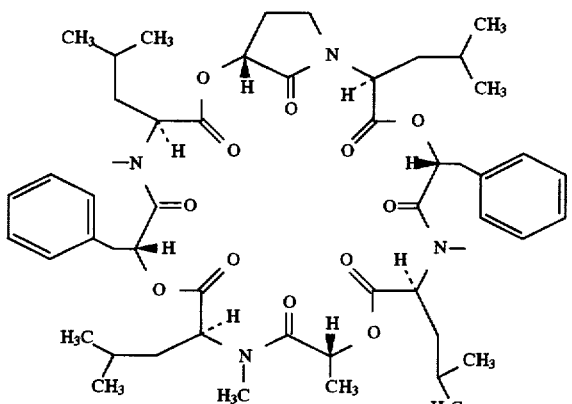

*919
GROUP 2

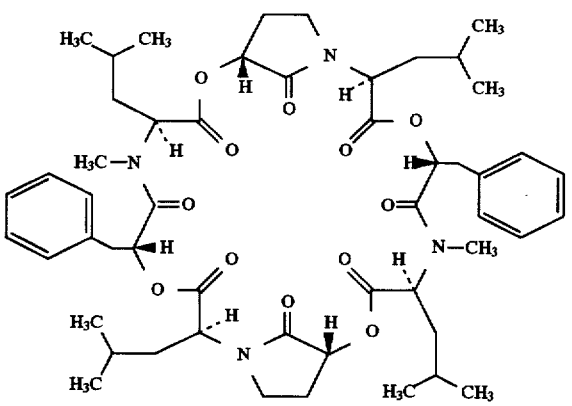

*210
GROUP 2

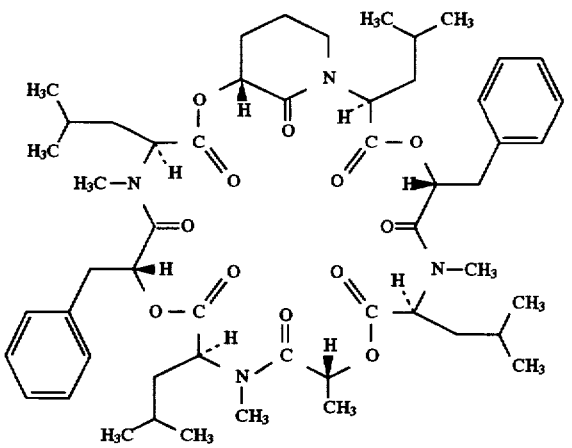

*312
GROUP 3

-continued
Table of Compounds

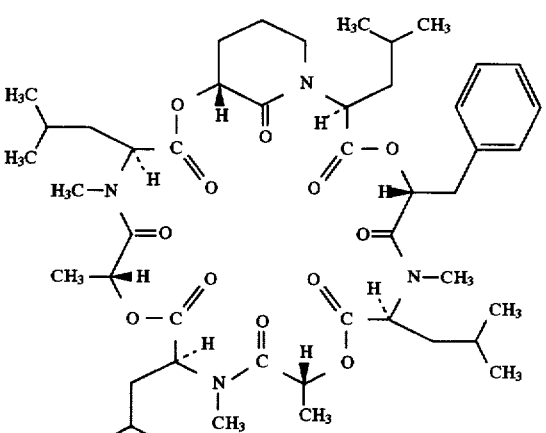

*353
GROUP 3

We claim:
1. A compound comprising the compounds represented by formula I, below,

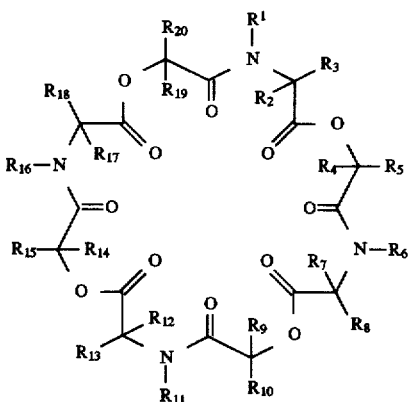

Formula I where, $R_1$, $R_6$, $R_{11}$ and $R_{16}$ are independent and selected from,
a) H,
b) $C_{1-4}$ optionally substituted alkyl, the alkyl optionally terminally substituted with, hydroxy or $C_{1-2}$ alkoxy, where, $R_2$, $R_3$, $R_4$, $R_5$, $R_7$, $R_8$, $R_9$, $R_{10}$, $R_{12}$, $R_{13}$, $R_{14}$, $R_{15}$, $R_{17}$, $R_{18}$, $R_{19}$ and $R_{20}$, are independent and selected from,
a) H
b) $C_{1-11}$ alkyl,
c) $C_{2-11}$ alkenyl
d) $C_{3-6}$ cycloalkyl,
e) $C_{1-11}$ alkoxy,
f) $C_{1-11}$ alkyl-$C_{1-11}$ alkoxy,
g) $C_{1-11}$ alkyl-O-$C_{1-6}$ alkyl,
h) $C_{6-12}$ aryl,
i) $C_{1-11}$ alkyl-$C_{6-12}$ aryl,
j) heterocyclic group
k) $C_{1-11}$ alkyl-heterocyclic group, where, the heterocyclic group is morpholino, piperidino, piperazino, imidazolyl, indolyl or guanidino, where, at least one of the following combinations of two R groups, $R_1$ with $R_3$, $R_6$ with $R_8$, $R_{11}$ with $R_{13}$, and $R_{16}$ with $R_{18}$, are taken together, to form a single or double heterocyclic ring structure, to form, 1) an optionally substituted heterocyclic ring of 5 to 9 members, or
2) a heterocyclic ring having the Nitrogen as shown in Formula I plus the additional optionally substituted ring atoms, where the ring atoms other than the N shown in Formula I may be either entirely C, or at least two carbon atoms plus one to three N, O or S substituted with 0–6 groups selected from,
   i) $C_{1-6}$ alkyl,
   ii) $C_{2-6}$ alkenyl
   iii) $C_{3-6}$ cycloalkyl,
   iv) phenyl,
   v) heterocyclic group,
   where the heterocyclic group is as defined above,
or
3) a double ring system where the two R groups ($R_1$ with $R_3$, $R_6$ with $R_8$, $R_{11}$ with $R_{13}$, or $R_{16}$ with $R_{18}$,) may be taken together to form a double ring system where each ring contains 5, 6 or 7 members (allowing double counting of common members), where
   i) the first ring is attached to the second ring directly with no covalent bonds (spiral type) or through a single covalent bond, (such as biphenyl type) between the two rings,
   ii) the first ring is attached to the second ring with one point of attachment on the first and second ring with either no carbons but one covalent bond (biphenyl type) or one carbon atom and two covalent bonds between the two rings, or
   iii) the first ring shares a covalent bond with the second ring such that common ring members are counted twice, as with an indole type structures,
where either the cyclic carbon ring, the heterocyclic ring or the double ring system may be optionally substituted with,
   1) $C_{1-4}$ alkyl, or
   2) $C_{2-4}$ alkenyl;
and pharmaceutically acceptable salts thereof.

2. A compound of claim 1 where $R_1$ through $R_{20}$, inclusive, are independently;

H, $C_{1-6}$ alkyl, optionally substituted $C_{1-6}$ alkyl-$C_{6-12}$aryl or form part of a single or double heterocyclic ring.

3. A compound of claim 2 where the combination of said two R groups form a heterocyclic ring nucleus containing 5, 6 or 7 members comprising one Nitrogen atom.

4. compound of claim 3 where $R_2$, $R_4$, $R_7$, $R_9$, $R_{12}$, $R_{14}$, and $R_{17}$ are hydrogen.

5. A compound of claim 4 where $R_3$ with $R_1$ form a 5, 6 or 7 member ring and $R_8$, $R_{13}$, and $R_{18}$, are independently, $C_1$–$C_4$ alkyl.

6. A compound of claim 5 where $R_3$ with $R_1$ form a 5 member ring and where $R_2$ is H or $C_{1-4}$ alkyl.

7. A compound of claim 6 where $R_8$, $R_{13}$, and $R_{18}$, are all iso-butyl.

8. A compound of claim 2 represented by formula 14, below.

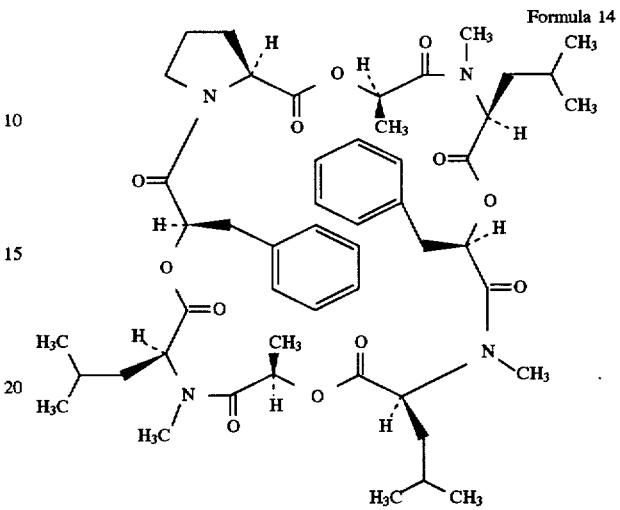

Formula 14

9. A compound of claim 3 where $R_1$ with $R_3$ form a 6 member ring, and where $R_2$ is H or $C_{1-4}$ alkyl and $R_6$, $R_{11}$, or $R_{16}$ is H or $C_{1-4}$ alkyl.

10. A compound of claim 9 where, $R_4$, $R_5$, $R_7$, $R_8$, $R_9$, $R_{10}$, $R_{12}$, $R_{13}$, $R_{14}$, $R_{15}$, $R_{17}$, $R_{18}$, $R_{19}$, $R_{20}$, are H, $C_{1-6}$ alkyl, benzyl or substituted benzyl.

11. A compound of claim 10 where $R_6$, $R_{11}$, or $R_{16}$ are H or methyl.

12. A compound of claim 11 where $R_6$, $R_{11}$, or $R_{16}$ are methyl and where, $R_4$, $R_5$, $R_7$, $R_8$, $R_9$, $R_{10}$, $R_{12}$m, $R_{13}$, $R_{14}$, $R_{15}$, $R_{17}$, $R_{18}$, $R_{19}$, $R_{20}$, are H, methyl, benzyl or iso-butyl.

13. A compound of claim 12 where $R_2$, $R_4$, $R_7$, $R_9$, $R_{12}$, $R_{14}$, $R_{17}$, $R_{19}$, are H.

14. A compound of claim 13, selected from Formula 27, 42, 49, 48, 50, 52, 51, 53, 54, or 55, below,

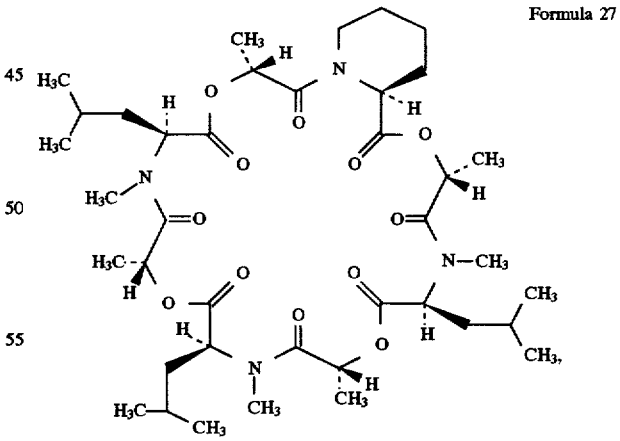

Formula 27

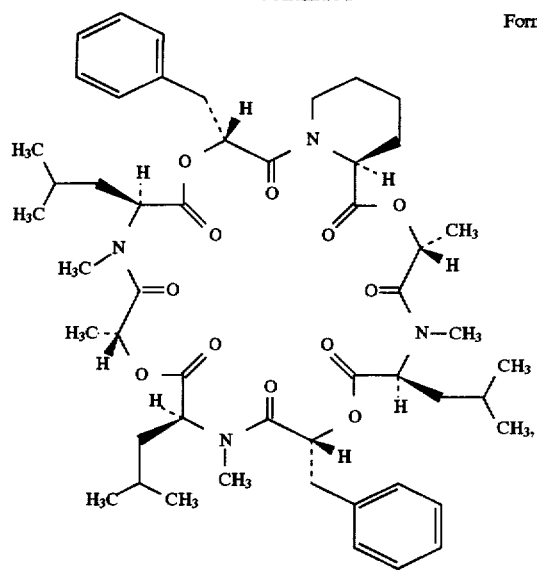
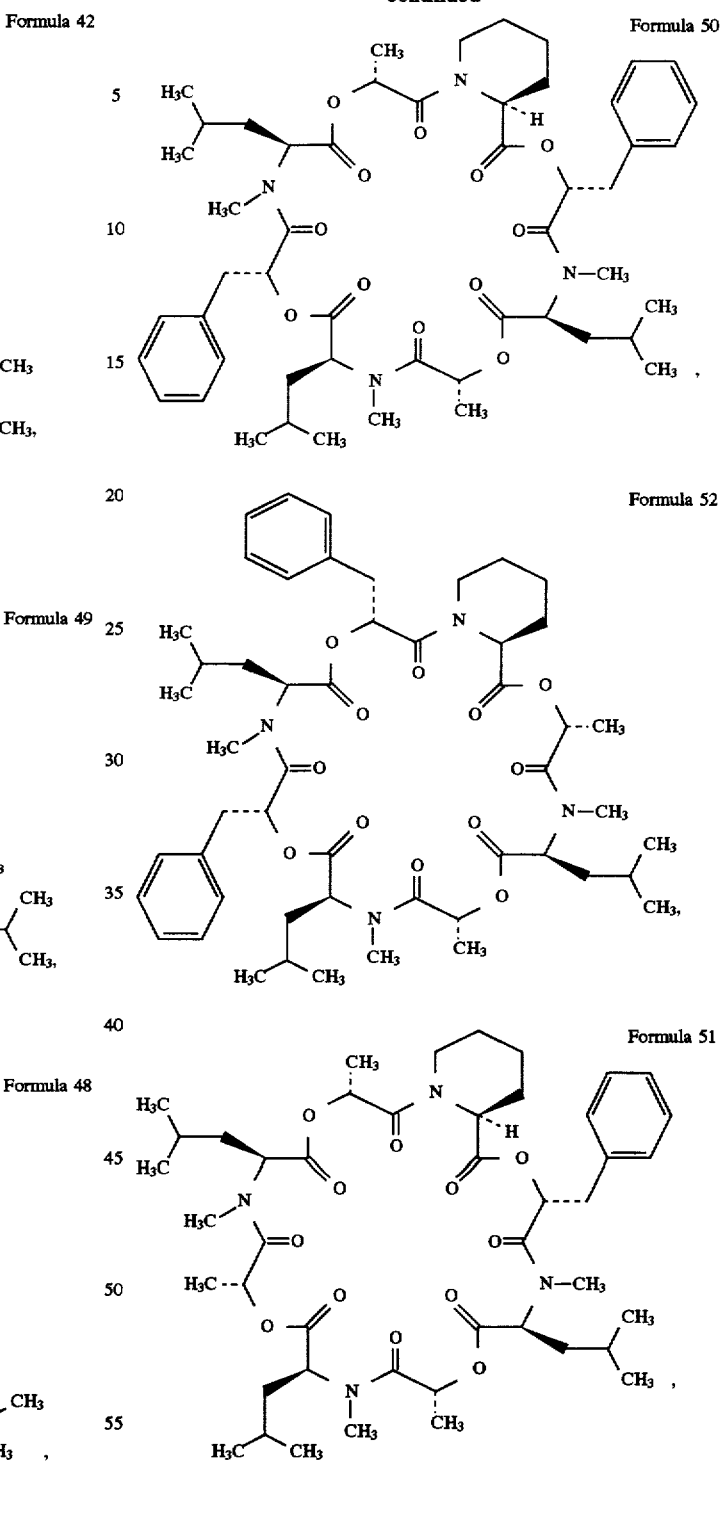

Formula 53
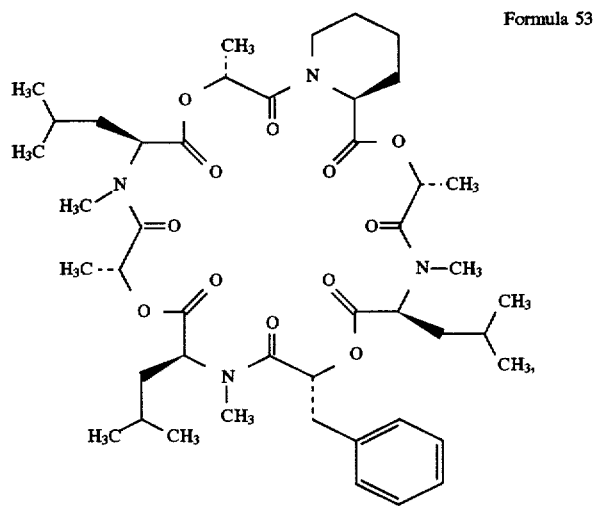
Formula 54
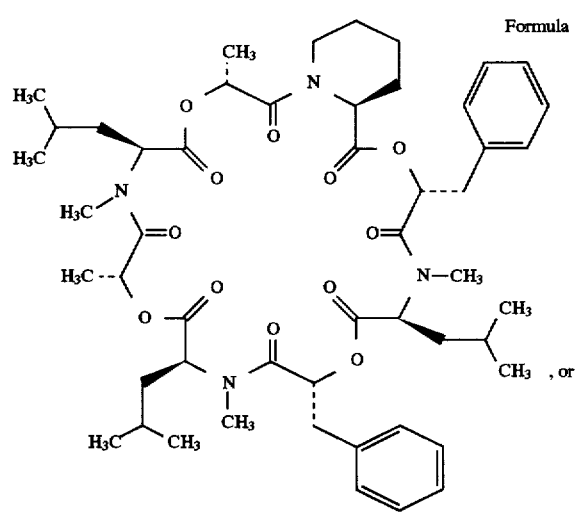, or
Formula 55
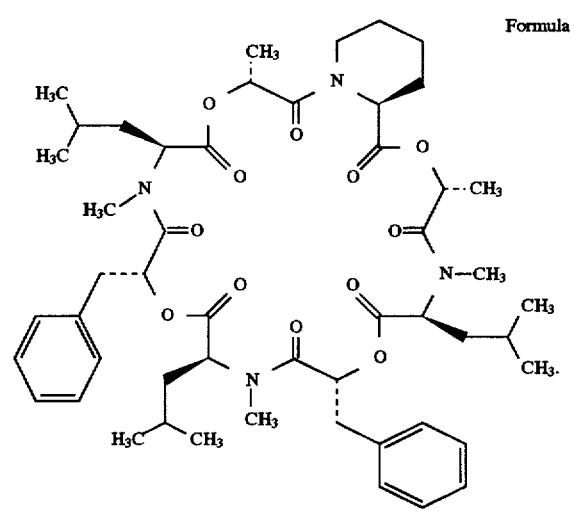
15. A compound of claim 10, where $R_{20}$, $R_{15}$, $R_{10}$, or $R_5$ are selected from morpholino substituted benzyl.
16. A compound of claim 15, of Formula 47,
Formula 47
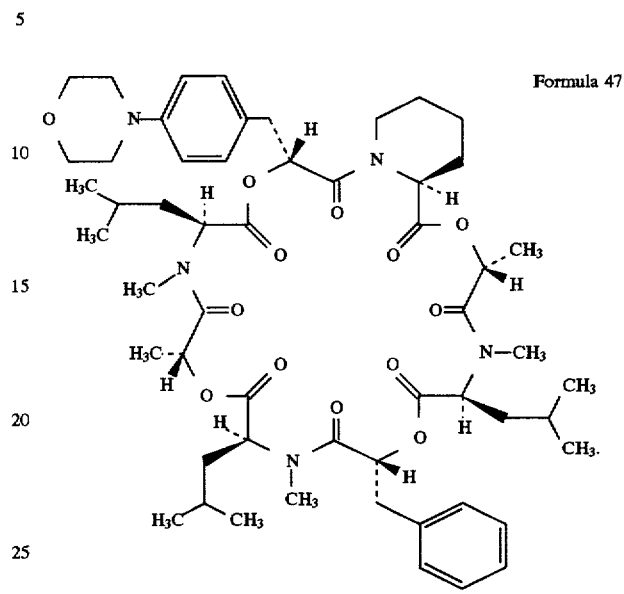
17. A compound of claim 13, where the six member ring formed by $R_1$ with $R_3$ contains a S atom as one member of that ring.
18. A compound of claim 17, selected from formula 56 or 57, below,
Formula 56
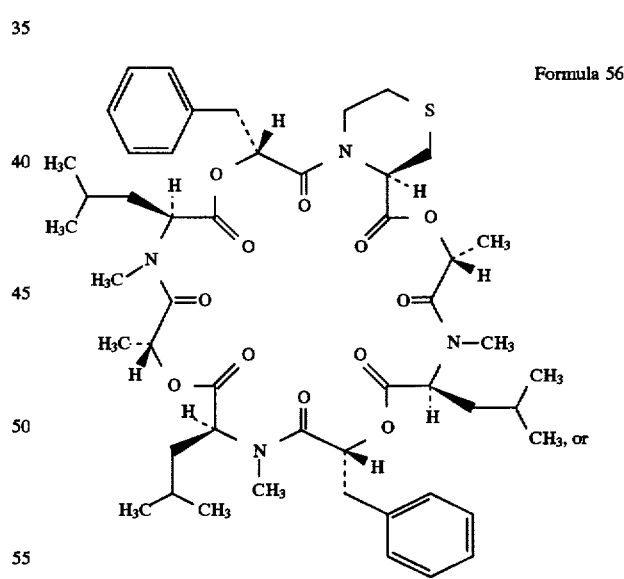, or Formula 57

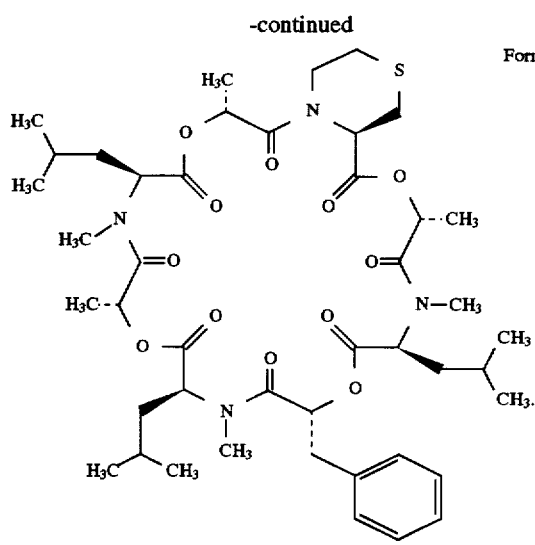

Group 1,
Chart H

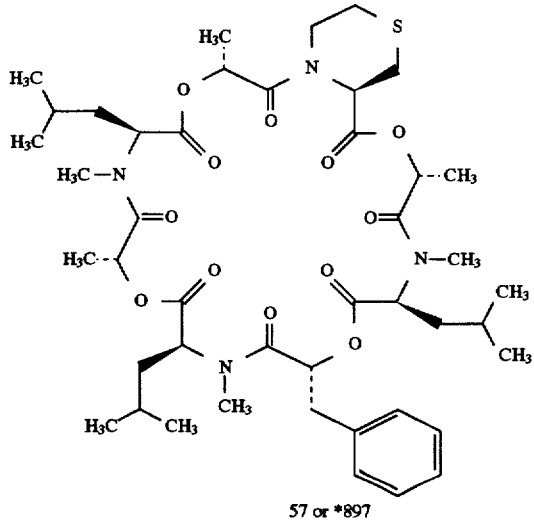

57 or *897

19. A compound of claim 3 where $R_1$ with $R_3$ form a 7 member ring where $R_2$ is H or $C_{1-4}$ alkyl and $R_6$, $R_{11}$, or $R_{16}$ is H or $C_{1-4}$ alkyl.

20. A compound of claim 19 where, $R_4$, $R_5$, $R_7$, $R_8$, $R_9$, $R_{10}$, $R_{12}$, $R_{13}$, $R_{14}$, $R_{15}$, $R_{17}$, $R_{18}$, $R_{19}$, $R_{20}$, are H, $C_{1-6}$ alkyl, benzyl or substituted benzyl.

21. A compound of claim 20 where $R_6$, $R_{11}$, or $R_{16}$ are H or methyl.

22. A compound of claim 21 where $R_6$, $R_{11}$, or $R_{16}$ are methyl and where, $R_4$, $R_5$, $R_7$, $R_8$, $R_9$, $R_{10}$, $R_{12}$, $R_{13}$, $R_{14}$, $R_{15}$, $R_{17}$, $R_{18}$, $R_{19}$, $R_{20}$, are H, methyl, benzyl or iso-butyl.

23. A compound of claim 22 where $R_2$, $R_4$, $R_7$, $R_9$, $R_{12}$, $R_{14}$, $R_{17}$, $R_{19}$, are H.

24. A compound of claim 23 represented by the formula 58, below,

Formula 58

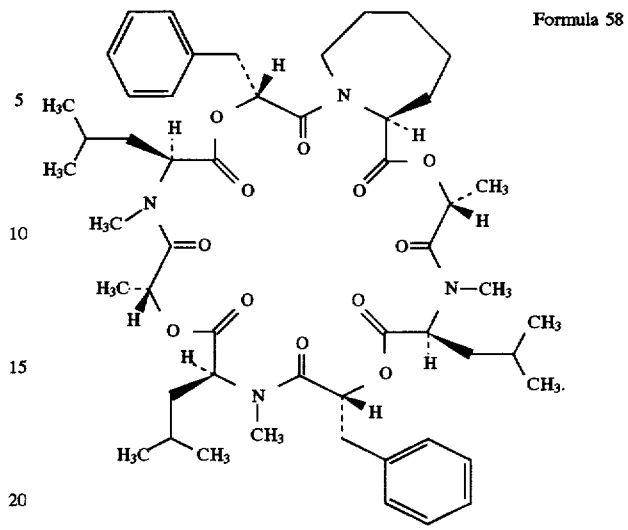

25. A compound of claim 23 where the seven member ring formed from $R_1$ with $R_3$ contains a S atom.

26. A compound of claim 25 where the compound is represented by formula 59, below, Formula 59

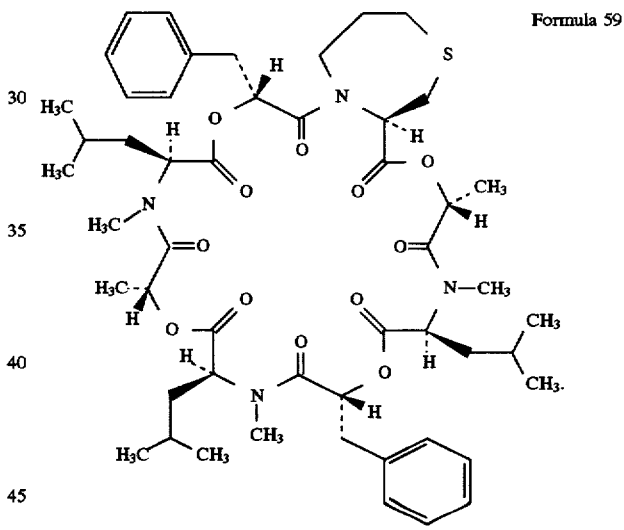

27. A compound of claim 2 where $R_1$ with $R_3$ form a double ring system where each ring contains 6 members.

28. A compound of claim 27 where the first ring shares a covalent bond with the second ring such that common members are counted twice, where the double ring system may be substituted.

29. A compound of claim 28 where the first ring is saturated and the second ring unsaturated.

30. A compound of claim 29 where the second ring is aryl or substituted aryl.

31. A compound of claim 30,
where $R_2$ is H or $C_{1-4}$ alkyl,
where $R_6$, $R_{11}$, or $R_{16}$ is H or $C_{1-4}$ alkyl, and
where, $R_4$, $R_5$, $R_7$, $R_8$, $R_9$, $R_{10}$, $R_{12}$, $R_{13}$, $R_{14}$, $R_{15}$, $R_{17}$, $R_{18}$, $R_{19}$, $R_{20}$, are H, $C_{1-6}$ alkyl, benzyl or substituted benzyl.

32. A compound of claim 31 where,
where $R_6$, $R_{11}$, or $R_{16}$ are H or methyl,
where $R_6$, $R_{11}$, or $R_{16}$ are methyl, where, $R_4$, $R_5$, $R_7$, $R_8$, $R_9$, $R_{10}$, $R_{12}$, $R_{13}$, $R_{14}$, $R_{15}$, $R_{17}$, $R_{18}$, $R_{19}$, $R_{20}$, are H, methyl, benzyl or iso-butyl, where $R_2$, $R_4$, $R_7$, $R_9$, $R_{12}$, $R_{14}$, $R_{17}$, $R_{19}$, are H.

33. A compound of claim 32 selected from formula 46, 33 or *867, below.

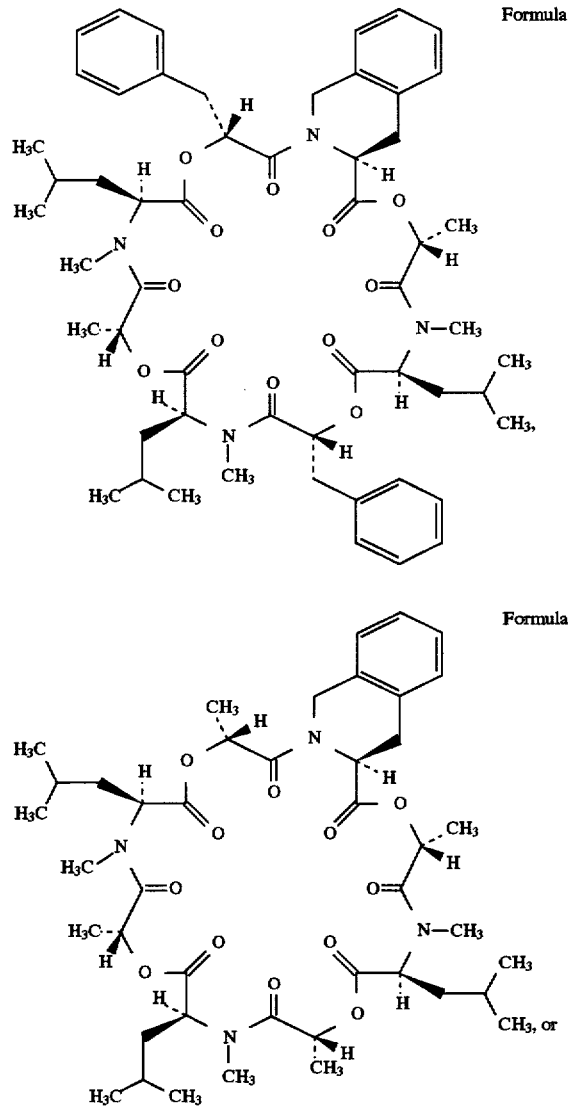

Formula 46

Formula 33

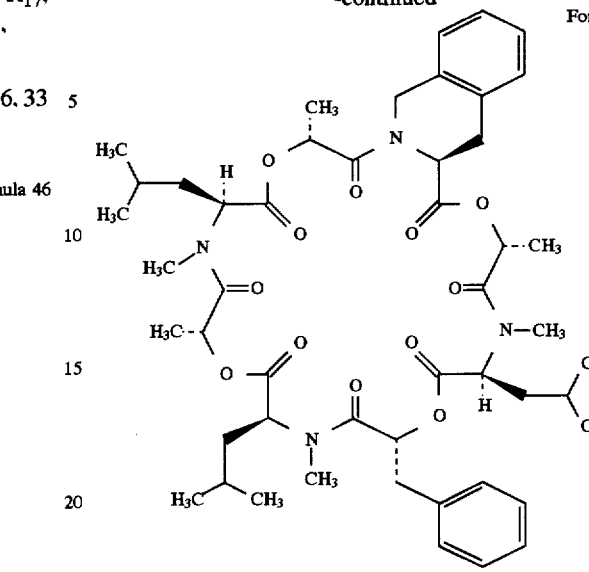

Formula *867

34. A compound comprising the compounds represented by formula I, below,

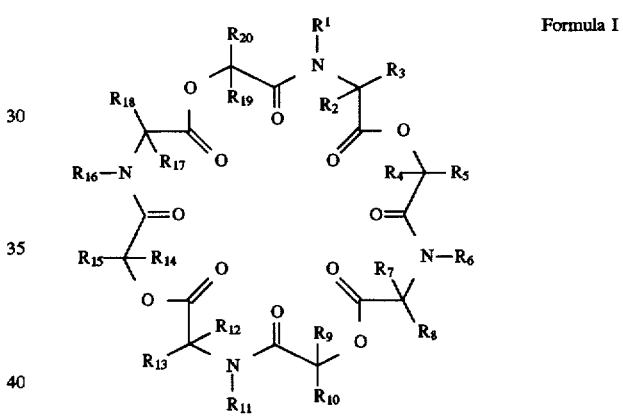

Formula I where, $R_1$, $R_6$, $R_{11}$, and $R_{16}$ are independent and selected from, a) H, b) $C_{1-4}$ optionally substituted alkyl, the alkyl optionally terminally substituted with, hydroxy or $C_{1-2}$alkoxy, where, $R_2$, $R_3$, $R_4$, $R_5$, $R_7$, $R_8$, $R_9$, $R_{10}$, $R_{12}$, $R_{13}$, $R_{14}$, $R_{15}$, $R_{17}$, $R_{18}$, $R_{19}$ and $R_{20}$, are independent and selected from, a) H b) $C_{1-11}$ alkyl, c) $C_{2-11}$ alkenyl d) $C_{3-6}$ cycloalkyl, e) OH f) $C_{1-11}$ alkoxy, g) $C_{1-11}$ alkyl-$C_{1-11}$ alkoxy, h) $C_{1-11}$ alkyl-O-$C_{1-6}$ alkyl, i) $C_{6-12}$ aryl, j) $C_{1-11}$ alkyl-$C_{6-12}$ aryl, k) heterocyclic group l) $C_{1-11}$ alkyl-heterocyclic group, where, the heterocyclic group is morpholino, piperidino, piperazino, imidazolyl, indolyl or guanidino, where, at least one of the following combinations of two R groups, $R_1$ with $R_{20}$, $R_6$ with $R_5$, $R_{11}$ with $R_{10}$, and $R_{16}$ with $R_{15}$, are taken together, to form a heterocyclic ring structure, to form, 1) an optionally substituted heterocyclic ring of 5 to 9 members, or 2) a heterocyclic ring having the Nitrogen as shown in Formula I plus the additional optionally substituted ring atoms, where the ring atoms other than the N shown in Formula I may be either entirely C, or at least two carbon atoms plus one to three N, O or S substituted with 0–6 groups selected from, i) $C_{1-6}$ alkyl, ii) $C_{2-6}$ alkenyl iii) $C_{3-6}$ cycloalkyl, iv) phenyl, v) heterocyclic group, where the heterocyclic group is as defined above, or 3) a double ring system where the two R groups ($R_1$ with $R_{20}$, $R_6$ with $R_5$, $R_{11}$ with $R_{10}$, or $R_{16}$ with $R_{15}$,) may be taken together to form a double ring system where each ring contains 5, 6 or 7 members (allowing double counting of common members), where i) the first ring is attached to the second ring directly with no covalent bonds (spiral type) or through a single covalent bond, (such as biphenyl type) between the two rings, ii) the first ring is attached to the second ring with one point of attachment on the first and second ring with either no carbons but one covalent bond (biphenyl type) or one carbon atom and two covalent bonds between the two rings, or iii) the first ring shares a covalent bond with the second ring such that common ring members are counted twice, as with an indole type structures, where either the cyclic carbon ring, the heterocyclic ring or the double ring system may be optionally substituted with, 1) $C_{1-4}$ alkyl, or 2) $C_{2-4}$ alkenyl;

and pharmaceutically acceptable salts thereof.

35. A compound of claim 34 where at least one of one of the following combinations of two R groups, $R_1$ with $R_{20}$, $R_6$ with $R_5$, $R_{11}$ with $R_{10}$, and $R_{16}$ with $R_{15}$, taken together, form a heterocyclic ring structures where the heterocyclic ring nucleus contains 5, 6 or 7 members comprising one Nitrogen atom.

36. A compound of claim 35 where the heterocyclic ring nucleus is a 5 member ring.

37. A compound of claim 36 where the 5 member heterocyclic ring is a gamma lactam ring.

38. A compound of claim 37 where $R_2$, $R_4$, $R_7$, $R_9$, $R_{12}$, $R_{14}$, $R_{17}$, and $R_{19}$ are hydrogen.

39. A compound of claim 38 where $R_3$, $R_5$, $R_6$, $R_8$, $R_{10}$, $R_{11}$, $R_{13}$, $R_{15}$, $R_{16}$, $R_{18}$, $R_{20}$ are selected from H, $C_{1-4}$ alkyl ,benzyl.

40. A compound of claim 39 where $R_3$, $R_5$, $R_6$, $R_8$, $R_{10}$, $R_{11}$, $R_{13}$, $R_{15}$, $R_{16}$, $R_{18}$, $R_{20}$ are selected from methyl, isobutyl or benzyl.

41. A compound of claim 40 containing 4 lactam rings.

42. A compound of claim 41, represented by formula *101, below,

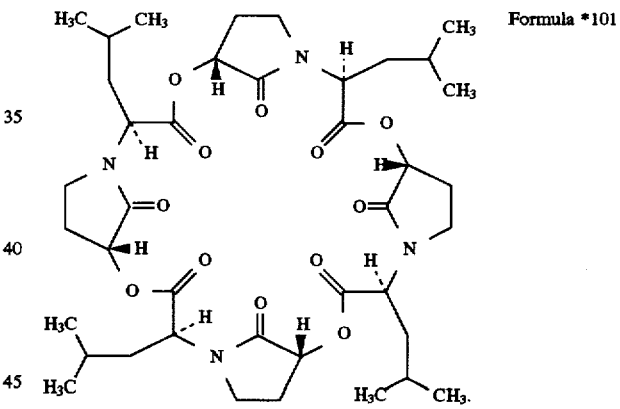

Formula *101

43. A compound of claim 40 containing two lactam rings.

44. A compound of claim 43, represented by the formula *210, below,

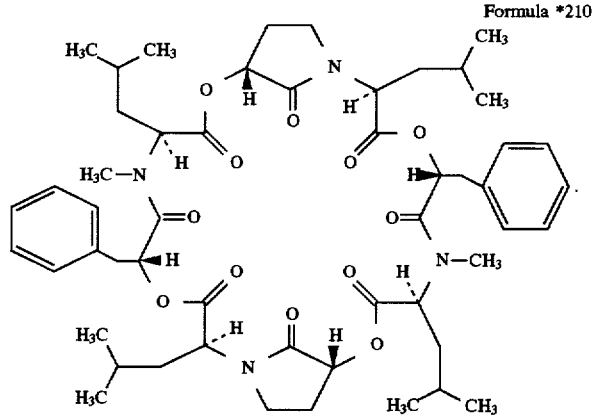

Formula *210

45. A compound of claim 40 containing one lactam ring.
46. A compound of claim 45, represented by the formula *919, below.

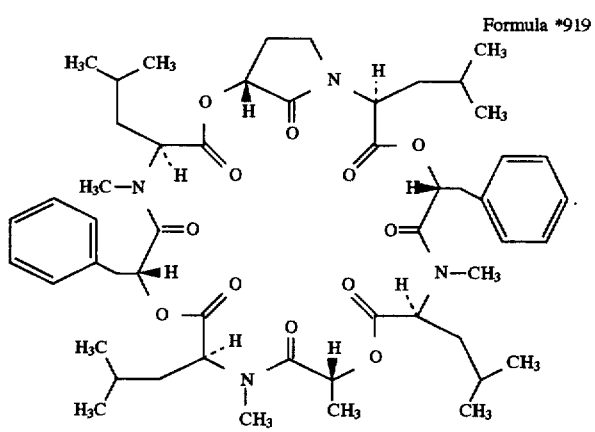

Formula *919

47. A compound of claim 35 where the heterocyclic ring nucleus is a 6 member ring.
48. A compound of claim 47 where the 6 member heterocyclic ring is a delta lactam ring.
49. A compound of claim 48 where $R_2$, $R_4$, $R_7$, $R_9$, $R_{12}$, $R_{17}$, and $R_{19}$ are hydrogen.
50. A compound of claim 49 where $R_3$, $R_5$, $R_6$, $R_8$, $R_{10}$, $R_{11}$, $R_{13}$, $R_{15}$, $R_{16}$, $R_{18}$, $R_{20}$ are selected from H, $C_{1-4}$ aLkyl, benzyl.
51. A compound of claim 50 where $R_3$, $R_5$, $R_6$, $R_8$, $R_{10}$, $R_{11}$, $R_{13}$, $R_{15}$, $R_{16}$, $R_{18}$, $R_{20}$ are selected from methyl, isobutyl or benzyl.
52. A compound of claim 51 containing one delta lactam ring.
53. A compound of claim 52 where $R_3$, $R_8$, $R_{13}$, and $R_{18}$ are all iso-butyl.
54. A compound of claim 52 where $R_6$, $R_{11}$, and $R_{16}$ are methyl.
55. A compound of claim 54, selected from the formulas *312 or *353, below,

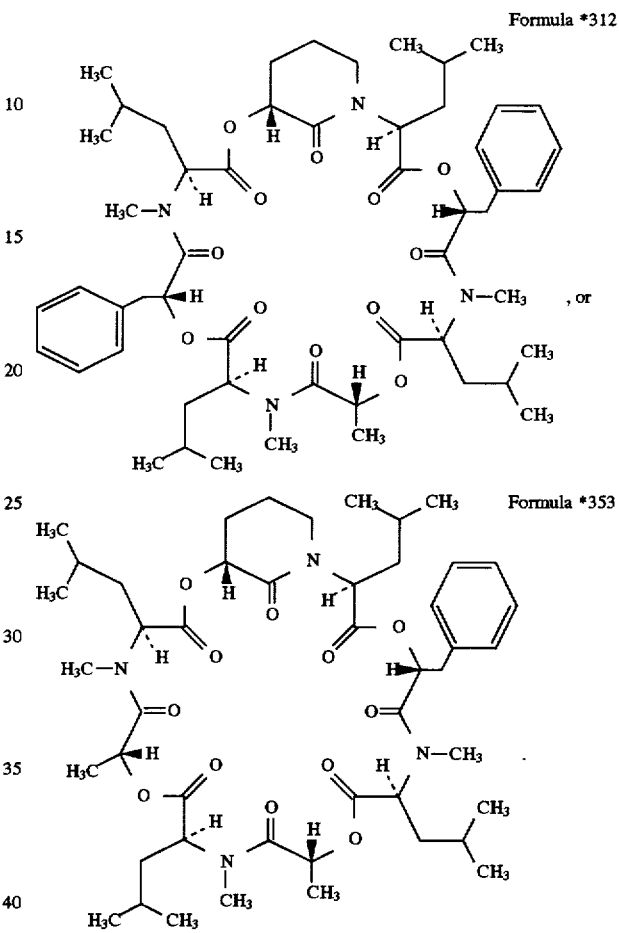

56. A method of using the compounds of claim 1 for the treatment of disease in animals, caused by the growth and replication of anthelmitic organisms.

57. A method of using the compounds of claim 34 for the treatment of disease in animals, caused by the growth and replication of anthelmitic organisms.

* * * * *